United States Patent
Cho et al.

(10) Patent No.: US 8,846,669 B2
(45) Date of Patent: Sep. 30, 2014

(54) OXAZOLIDINONE DERIVATIVE AND MEDICAL COMPOSITION CONTAINING SAME

(75) Inventors: Young Lag Cho, Daejeon (KR); Sung Yoon Baek, Daejeon (KR); Sang Eun Chae, Daejeon (KR); Sun Young Kim, Daejeon (KR); Hong Bum Lee, Daejeon (KR); Hyang Sook Lee, Daejeon (KR); Kyuman Oh, Daejeon (KR); Hye Jin Heo, Daejeon (KR); Tae Kyo Park, Daejeon (KR); Sung Ho Woo, Daejeon (KR); Yong Zu Kim, Daejeon (KR)

(73) Assignee: Legochem Biosciences, Inc., Daegeon (KR)

( * ) Notice: Subject to any disclaimer, the term of this patent is extended or adjusted under 35 U.S.C. 154(b) by 0 days.

(21) Appl. No.: 14/008,702

(22) PCT Filed: Mar. 29, 2012

(86) PCT No.: PCT/KR2012/002314
§ 371 (c)(1),
(2), (4) Date: Dec. 13, 2013

(87) PCT Pub. No.: WO2012/134188
PCT Pub. Date: Oct. 4, 2012

(65) Prior Publication Data
US 2014/0179691 A1 Jun. 26, 2014

(30) Foreign Application Priority Data
Mar. 30, 2011 (KR) .................. 10-2011-0028559

(51) Int. Cl.
*C07D 413/14* (2006.01)
*A61K 31/53* (2006.01)
*A61K 31/5355* (2006.01)

(52) U.S. Cl.
USPC ........... 514/229.2; 514/242; 544/65; 544/182

(58) Field of Classification Search
CPC ... C07D 413/14; A61K 31/53; A61K 31/5355
USPC .................. 544/65, 182; 514/229.2, 242
See application file for complete search history.

(56) References Cited

U.S. PATENT DOCUMENTS 8,242,113 B2 * 8/2012 Cho et al. .................. 514/229.2
8,637,667 B2 * 1/2014 Cho et al. ........................ 544/66

* cited by examiner

*Primary Examiner* — Kahsay Habte
(74) *Attorney, Agent, or Firm* — Birch, Stewart, Kolasch & Birch, LLP

(57) ABSTRACT

Disclosed is a novel oxazolidinone derivative represented by Formula 1 above, in particular, a novel oxazolidinone compound having a cyclic amidoxime or cyclic amidrazone group.
In Formula 1, R and Q are the same as defined in the detailed description.
In addition, disclosed is a pharmaceutical composition for an antibiotic which includes the novel oxazolidinone derivative of Formula 1, a prodrug thereof, a hydrate thereof, a solvate thereof, an isomer thereof, or a pharmaceutically acceptable salt thereof as an active ingredient.
The novel oxazolidinone derivative, the prodrug thereof, the hydrate thereof, the solvate thereof, the isomer thereof, and the pharmaceutically acceptable salt thereof have broad antibacterial spectrum against resistant bacteria, low toxicity and strong antibacterial effects against Gram-positive and Gram-negative bacteria and thus may be effectively used as antibiotics.

12 Claims, No Drawings

OXAZOLIDINONE DERIVATIVE AND MEDICAL COMPOSITION CONTAINING SAME

CROSS-REFERENCE TO RELATED PATENT APPLICATIONS

The present application is a U.S. national stage application under 35 U.S.C. §371 of PCT Application No. PCT/KR2012/002314, filed Mar. 29, 2012, which claims priority to KR10-2011-0028559 filed on Mar. 30, 2011, the entireties of which are incorporated by reference herein.

TECHNICAL FIELD

The present invention relates to a novel oxazolidinone derivative. More specifically, the present invention relates to a novel oxazolidinone derivative having a cyclic amidoxime or cyclic amidrazone group. In addition, the present invention relates to a pharmaceutical composition for an antibiotic which includes the oxazolidinone derivative, a prodrug thereof, a hydrate thereof, a solvate thereof, an isomer thereof, or a pharmaceutically acceptable salt thereof as an active ingredient.

BACKGROUND ART

Since linezolid, which is an oxazolidinone antibiotic, was first reported in 1984 (see European Patent Publication No. 127,902), a variety of oxazolidinone derivatives have been reported by various pharmaceutical firms. However, medicines under development do not have superior properties to linezolid (Product name: Zyvox) in terms of toxicity and efficacy. Due to such problems, linezolid is still drawing attention as the best alternative to vancomycin in treatment against methicillin-resistant *staphylococcus aureus* (MRSA). If linezolid-resistant bacteria, which have recently been reported, continue to spread, however, very serious problems, i.e., no cure for linezolid-resistant bacteria, occur.

For this reason, there is a very urgent need to develop medicines having superior properties to linezolid in terms of effects or toxicity and having efficacy for linezolid-resistant bacteria. Korean Patent Application No.: 10-2008-0093712, which was filed by the present inventors in Sep. 24, 2008, discloses that an oxazolidinone antibiotic having a cyclic amidrazone or cyclic amidoxime group has superior properties to linezolid in terms of efficacy and toxicity and the oxazolidinone antibiotic has various advantages due to introduction of the cyclic amidrazone group.

In particular, the cyclic amidrazone group is weakly basic and thus forms a salt. When the cyclic amidrazone group forms a hydrochloride, the hydrochloride has similar acidity to acetic acid, i.e., a pKa of about 5. Due to such weak acidity, antibacterial effects are not deteriorated and solubility of the hydrochloride with respect to water may be significantly increased.

However, the oxazolidinone antibiotic disclosed in the above-described patent application also has an insignificant effect on linezolid-resistant bacteria and thus cannot be used to effectively treat infections with linezolid-resistant bacteria under circumstances which the bacteria continue to spread.

DISCLOSURE

Technical Problem

As a result of a variety of extensive and intensive studies and experiments to solve the problems as described above, the present inventors discovered that, as described below, novel oxazolidinone derivatives represented by Formula 1 below, in particular, novel oxazolidinone compounds having a cyclic amidoxime or cyclic amidrazone group, have an excellent effect on linezolid-resistant bacteria, has higher antibacterial ability than conventional antibiotics, and has high solubility that enables the oxazolidinone derivatives to be readily developed as oral and injectable drugs, thus completing the present invention based on the discovery.

In particular, the present invention provides a compound represented by Formula 1 below.

The present invention also provides a prodrug of the compound, a solvate of the compound, an isomer of the compound, or a pharmaceutically acceptable salt of the compound.

The present invention also provides a pharmaceutical composition including the compound and an antibiotic treatment method using an effective amount of the compound.

Technical Solution

In accordance with one aspect of the present invention, provided is a novel oxazolidinone derivative represented by Formula 1 below, in particular, a novel oxazolidinone compound having a cyclic amidoxime or cyclic amidrazone group. In addition, the present invention also provides a novel oxazolidinone derivative represented by Formula 1 below, a prodrug thereof, a hydrate thereof, a solvate thereof, an isomer thereof, and a pharmaceutically acceptable salt thereof:

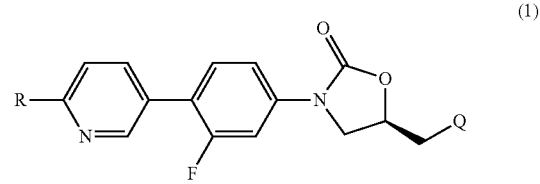

wherein R is a heterocyclic group selected from the following groups:

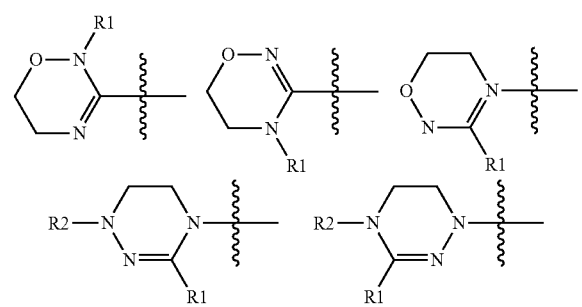

$R_1$ is hydrogen, $C_1$-$C_6$ alkyl, or $C_3$-$C_6$ cycloalkyl;

$R_2$ is hydrogen, $C_1$-$C_6$ alkyl, or $(CH_2)_mC(\!=\!O)R_{21}$, wherein $R_{21}$ is hydrogen, $(CH_2)_n NHR_{211}$, wherein $R_{211}$ is hydrogen or $C_1$-$C_6$ alkyl, $CH_2OH$, or $CH(OH)CH_2OH$, and m and n are each independently an integer of 0 to 3; and Q is $OR_3$, $NHR_3$ or

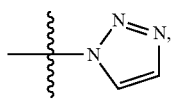

wherein $R_3$ is hydrogen, $C_1$-$C_6$ alkyl, —C(=O)$R_{31}$, wherein $R_{31}$ is hydrogen, $C_1$-$C_6$ alkyl, $C_3$-$C_6$ cycloalkyl, or O—($C_1$-$C_6$) alkyl, or a hetero aromatic ring group selected from the following groups;

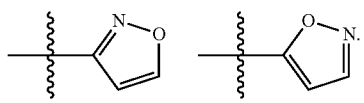 [SMILES: *c1ccon1 ; *c1ccno1]

The compound is a novel compound, a chemical structure of which has rarely been researched. Thus, by introducing a cyclic amidoxime or cyclic amidrazone group to an oxazolidinone antibiotic, absorptivity may be significantly improved, and solubility of the compound with respect to water may be significantly increased because the cyclic amidoxime or cyclic amidrazone group has appropriate basicity and thus forms a salt. Due to increase in solubility with respect to water, the compound may be prepared in the form of an injection without taking the form of a prodrug, and the compound has little toxicity.

The oxazolidinone derivative exhibits antibacterial ability against Gram-positive bacteria such as *Staphylococcus aureus, Enterococcus faecalis*, and the like and Gram-negative bacteria such as *Haemophilus influenza, Moraxella catarrhalis*, and the like, which are resistant to existing antibiotics, at a much lower concentration than commercially available linezolid. In particular, the oxazolidinone derivative exhibits excellent antibacterial ability against linezolid-resistant *Enterococcus faecium*.

The term "alkyl" as used herein includes linear and branched structures. For example, $C_1$-$C_6$ alkyl includes all possible position and geometrical isomers such as methyl, ethyl, propyl, isopropyl, butyl, isobutyl, tert-butyl, pentyl, hexyl, and the like.

The term "$C_3$-$C_6$ cycloalyl" includes all ring-type position and geometrical isomers such as cyclopropyl, cyclobutyl, cyclopentyl, cyclohexyl, cyclopropylmethyl, and the like.

Preferably, the oxazolidinone derivative of Formula 1 may be a compound represented by one selected from Formulas 2 to 4:

(2)

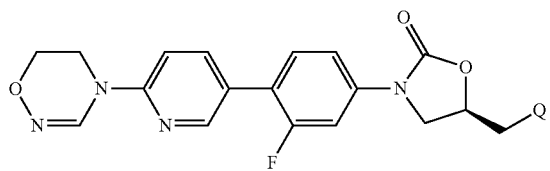

(3)

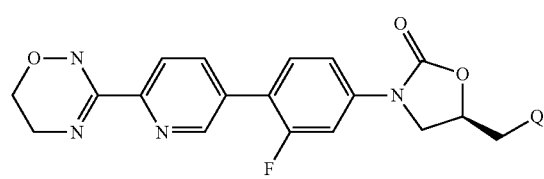

(4)

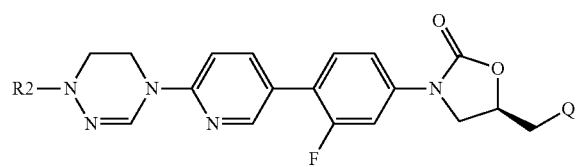

wherein $R_2$ and Q are the same as defined above with regards to Formula 1.

More preferably, the oxazolidinone derivative of Formula 1 may be a compound of Formula 2, 3 or 4 above, wherein Q is NHC(=O)CH$_3$, NHC(=O)OCH$_3$,

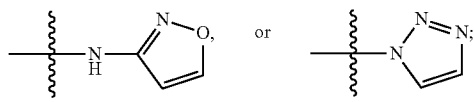 [SMILES: *Nc1ccon1 ; *n1ccnn1]

and $R_2$ is methyl, C(=O)CH$_2$OH, C(=O)CH$_2$NH$_2$, or C(=O)CH(OH)CH$_2$OH.

The oxazolidinone derivative according to the present invention may be one of the following compounds, but is not limited thereto.

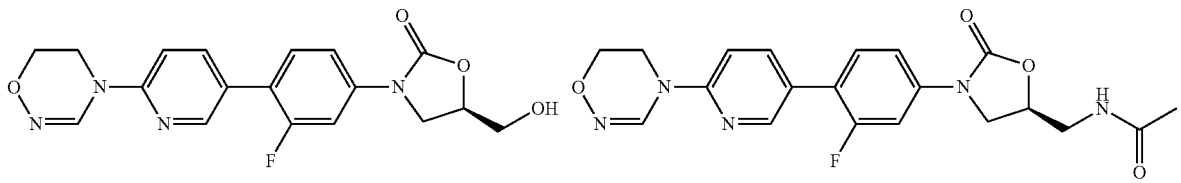

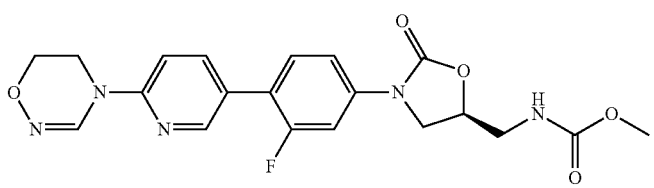

-continued
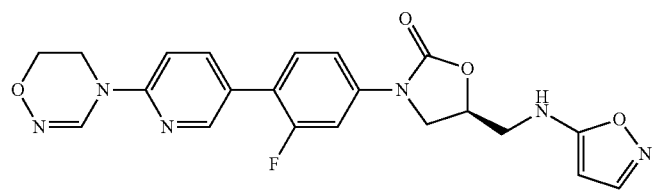
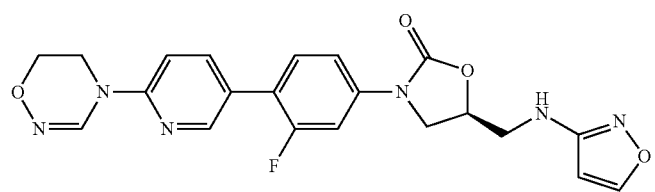
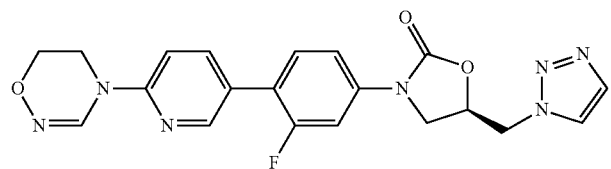
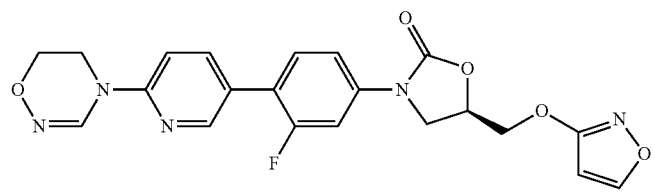
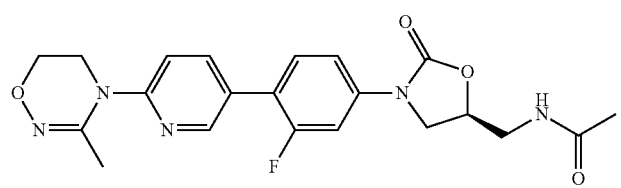
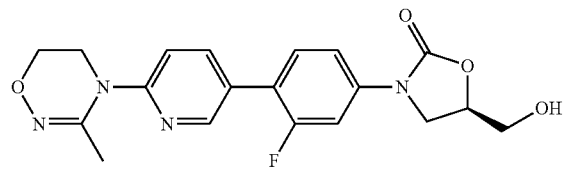
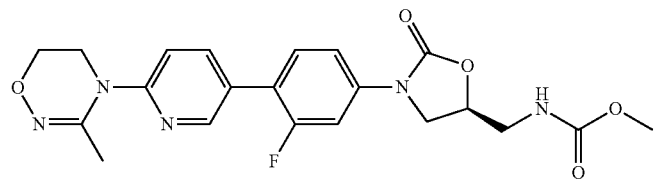
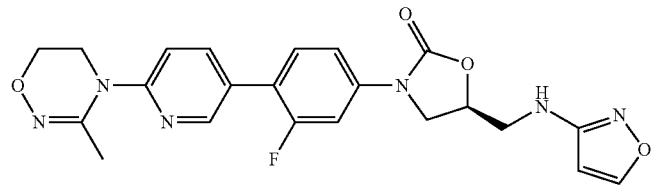
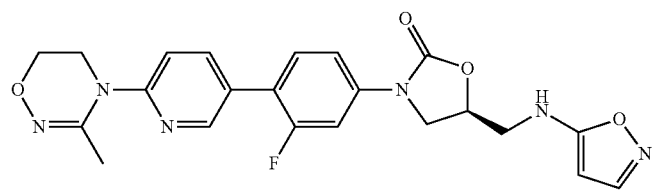

-continued
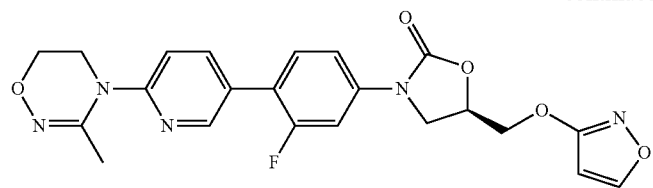
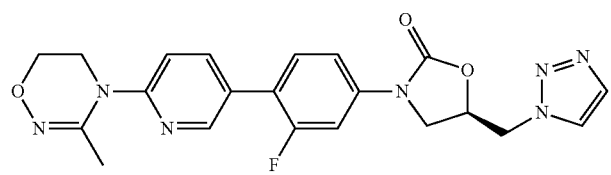
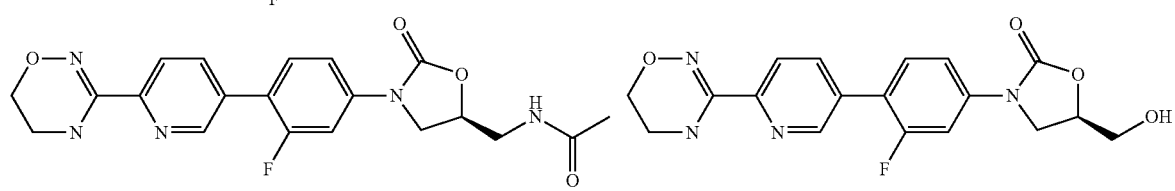
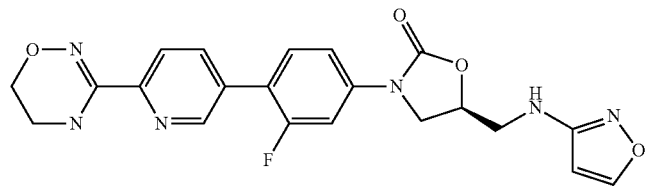
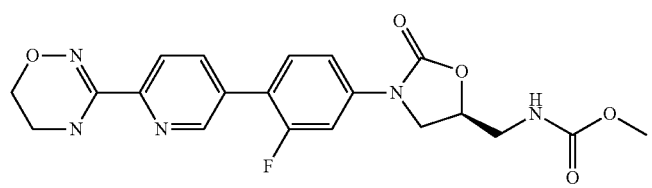
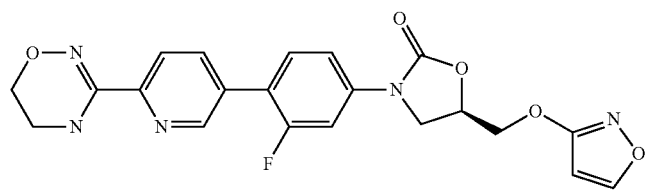
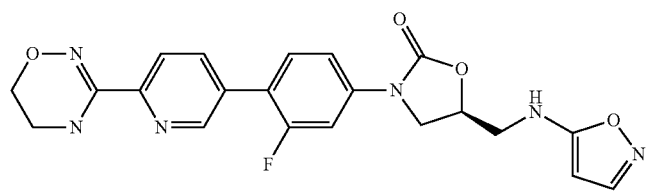
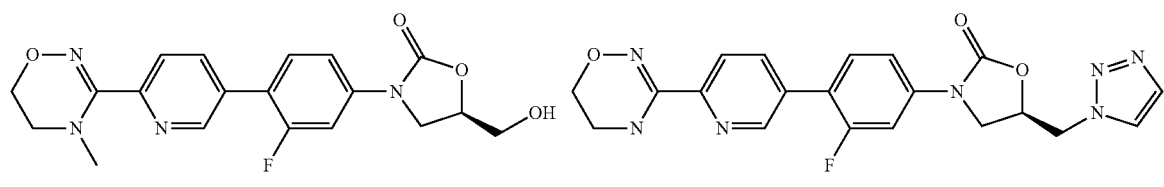
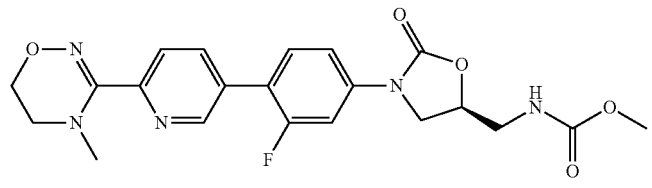

-continued
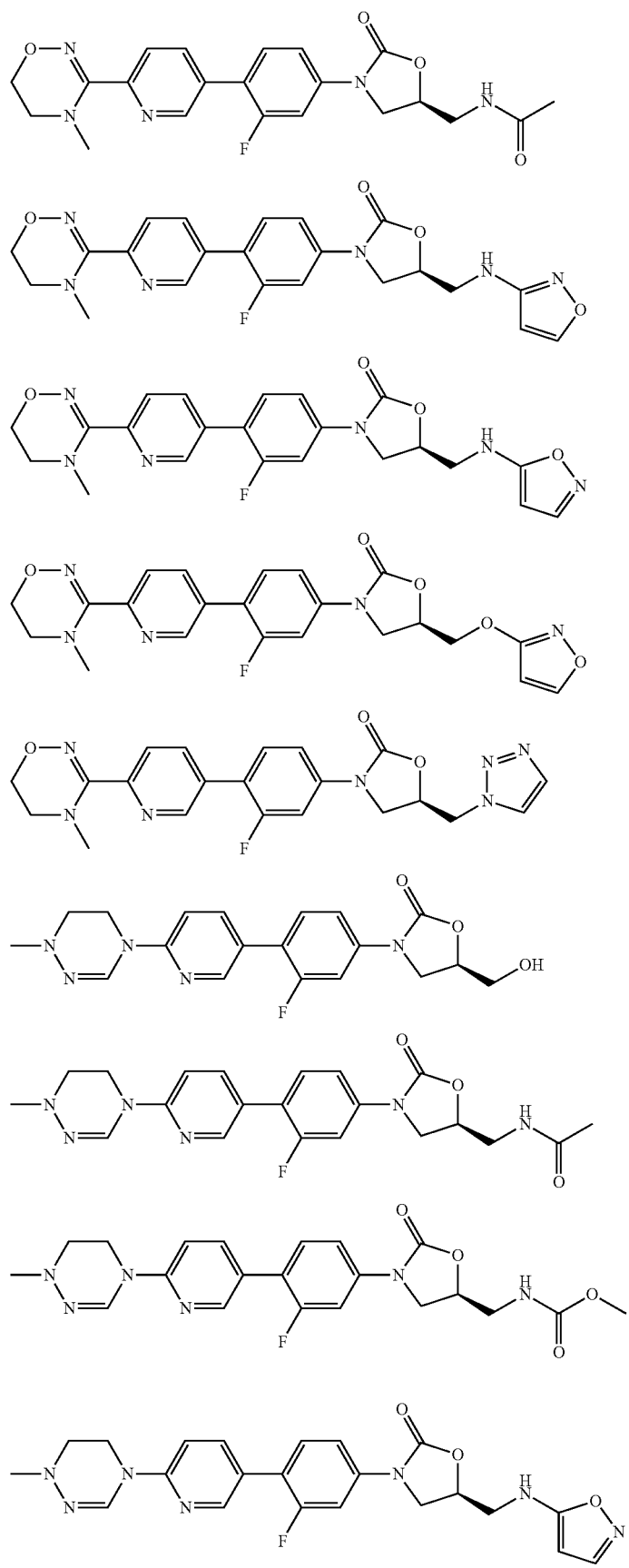

-continued
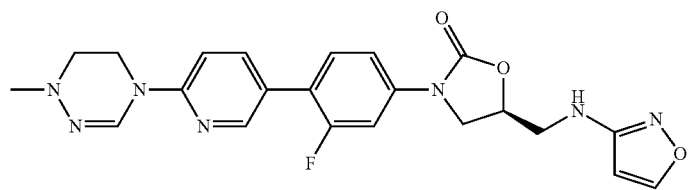
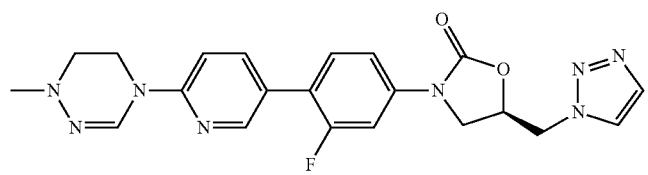
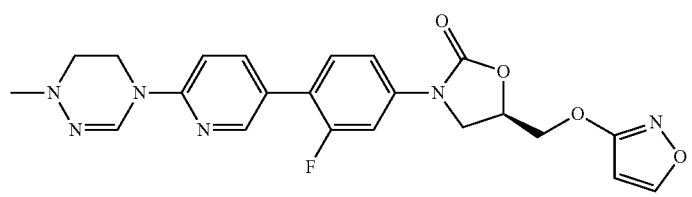
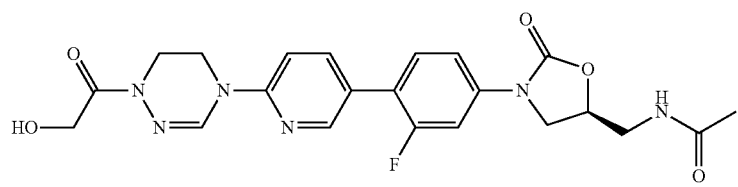
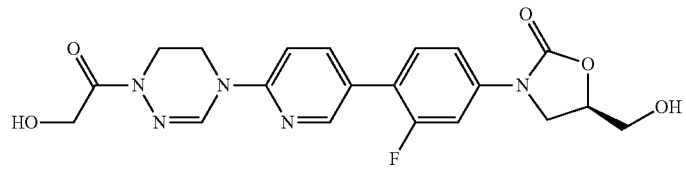
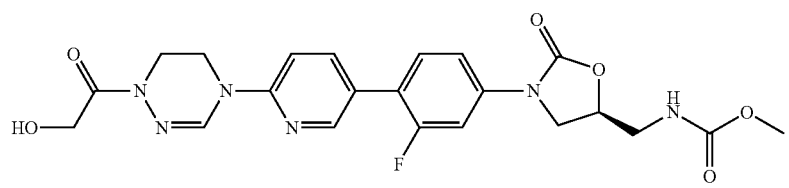
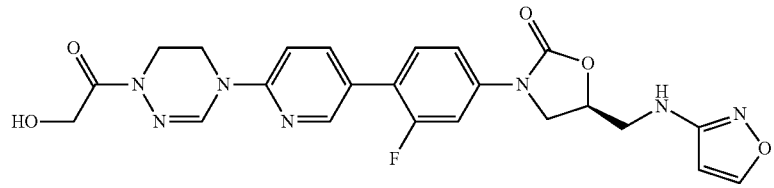
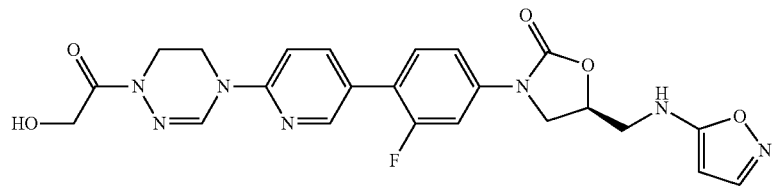
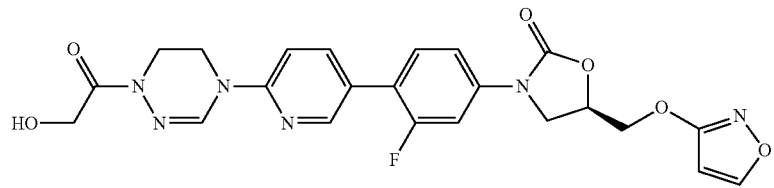

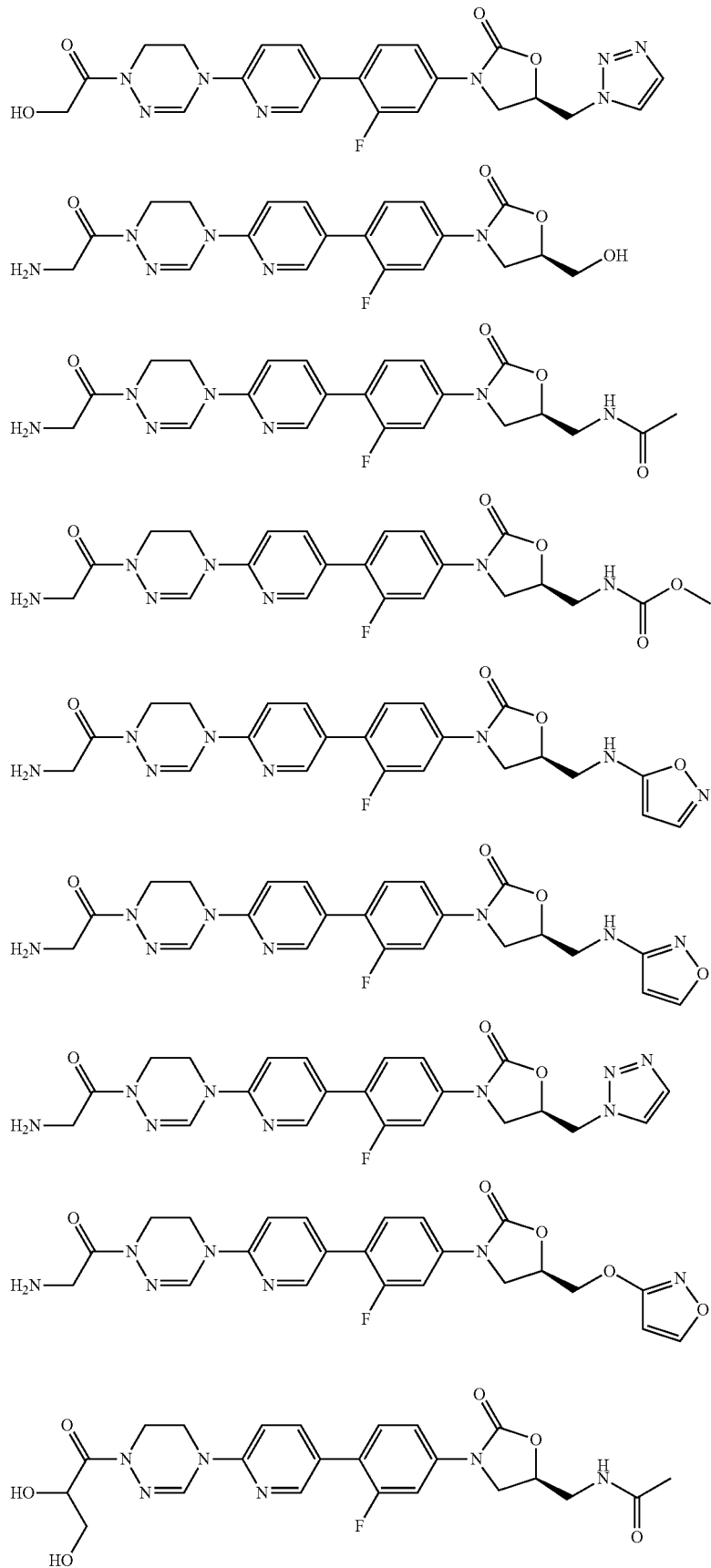

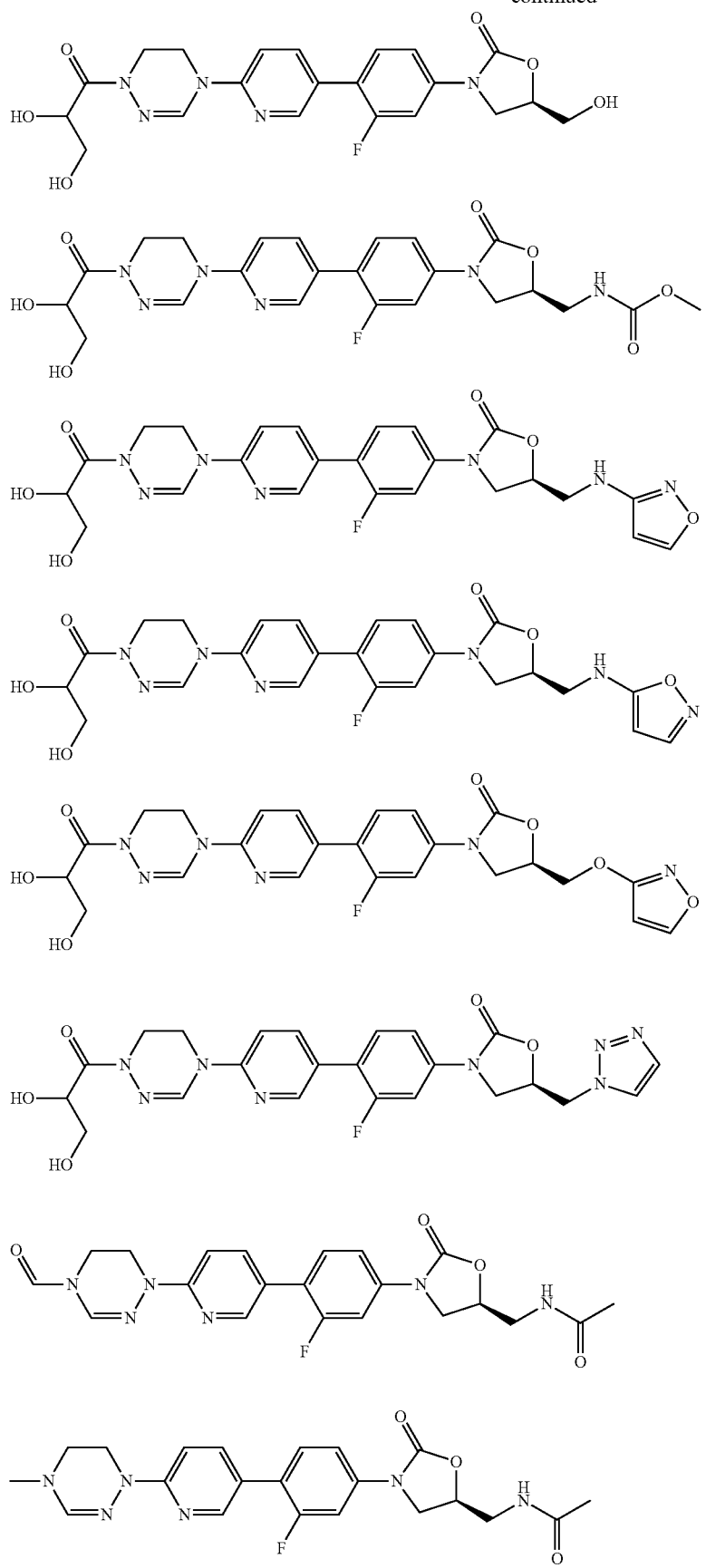

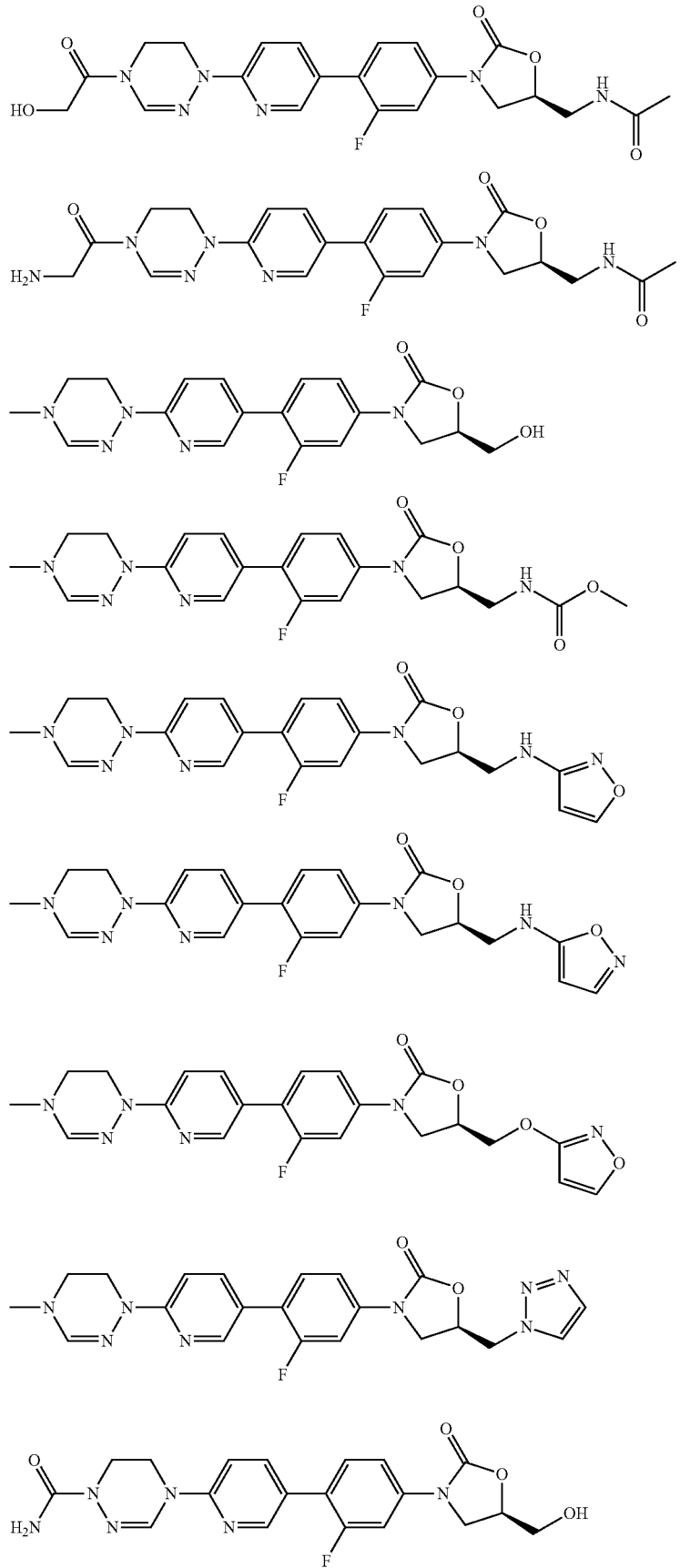

-continued
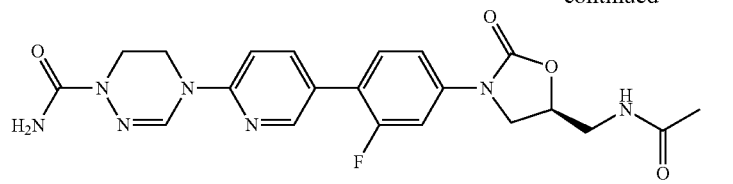
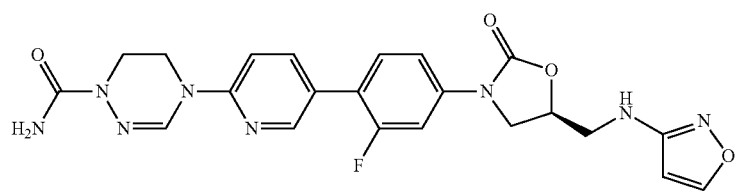
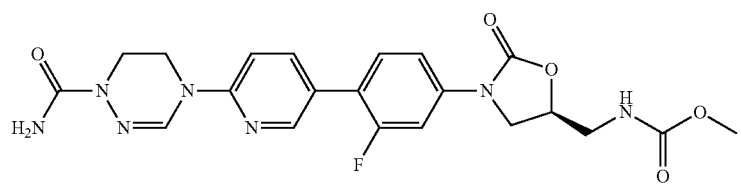
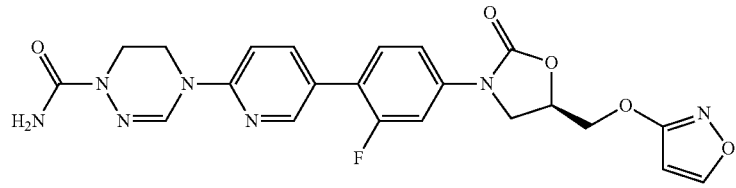
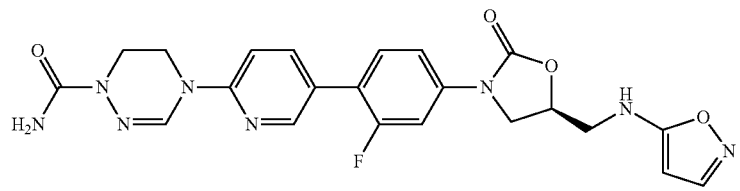
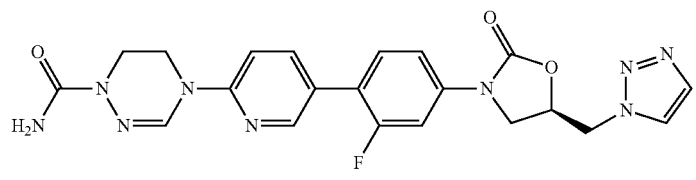
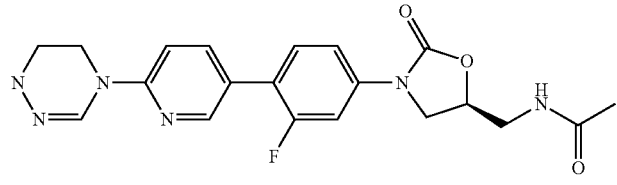
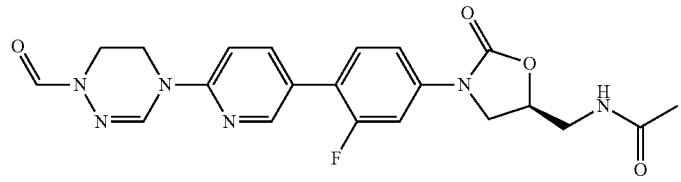
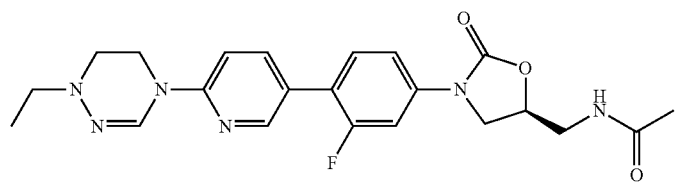

-continued

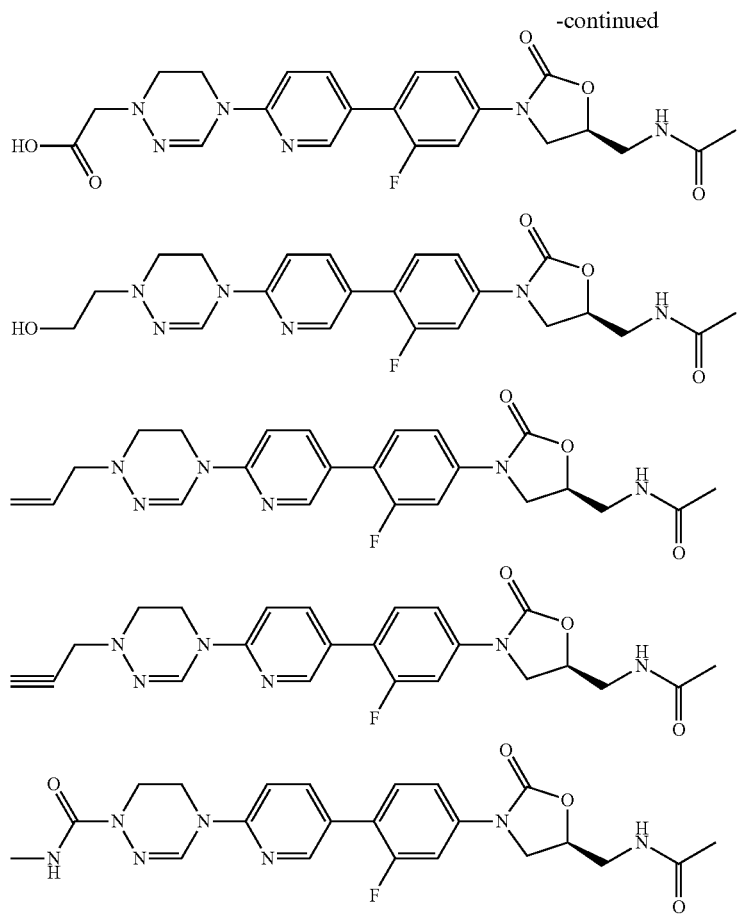

The oxazolidinone derivative according to the present invention may be prepared into a prodrug, a hydrate, a solvate, an isomer, or a pharmaceutically acceptable salt to enhance bioavailability or solubility. Thus, the prodrug, hydrate, solvate, isomer and pharmaceutically acceptable salt of the oxazolidinone derivative are also within the scope of the present invention.

Hereinafter, the terms as used herein will be briefly described.

The term "pharmaceutically acceptable salt" refers to formulations of a compound that do not cause severe irritation to an organism into which the compound is administered and do not deteriorate biological activity and physical properties of the compound. The terms "hydrate," "solvate," "isomer," and "prodrug" also mean the same as defined above. Pharmaceutically acceptable salts include pharmaceutically acceptable, anion-containing, non-toxic acid addition salts formed by acids, for example, inorganic acids such as hydrochloric acid, sulfuric acid, nitric acid, phosphoric acid, hydrobromic acid, hydriodic acid, and the like, organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, and the like, and sulfonic acids such as methane sulfonic acid, ethane sulfonic acid, benzene sulfonic acid, p-toluene sulfonic acid, and the like. Examples of pharmaceutically acceptable carboxylic acid salts include metallic salts or alkaline earth metal salts of lithium, sodium, potassium, calcium, magnesium, and the like, amino acid salts such as lysine, arginine, guanidine, and the like, and organic salts such as dicyclohexylamine, N-methyl-D-glucamine, tris(hydroxymethyl)methylamine, diethanolamine, choline, triethylamine, and the like. The compound of Formula 1 may be converted into a salt using a conventional method.

The term "hydrate" refers to the compound or salt thereof according to the present invention that contains stoichiometric or non-stoichiometric amounts of water bound thereto by non-covalent intermolecular force.

The term "solvate" refers to the compound or salt thereof according to the present invention that contains stoichiometric or non-stoichiometric amounts of water bound thereto by non-covalent intermolecular force. In this regard, preferable solvents may be volatile solvents, nontoxic solvents, and/or solvents suitable for administration to humans.

The term "isomers" refers to compounds or salts thereof according to the present invention that have the same chemical or molecular formula but different structural formulas. Such isomers include structural isomers such as tautomers and the like, R or S isomers having an asymmetric carbon center, and stereoisomers such as geometric isomers (trans-, cis-) and the like. All the isomers and mixtures thereof are also within the scope of the present invention.

The term "prodrug" refers to an agent that is converted into a parent drug in vivo. In some cases, prodrugs are often used because of easier administration than parent drugs. For example, prodrugs have bioavailability when orally administered, whereas parent drugs may not. In addition, a prodrug may have improved solubility in a pharmaceutical composition when compared to a parent drug. For example, the prodrug may be an in vivo hydrolysable ester of the compound according to the present invention or a pharmaceutically acceptable salt thereof. In addition, the prodrug may be a short peptide (polyamino acid) with an acid radical linked thereto that is metabolized such that the peptide exposes an active site.

Other terms as used herein may be interpreted as commonly understood in the art to which the present invention pertains.

Various types of prodrugs are known in the art, and non-limiting examples of cited references include:
a) [Design of Prodrugs, edited by H. Bundgaard, (Elsevier, 1985) and Methods in Enzymology, Vol. 42, p. 309-396, edited by K. Widder, et al. (Academic press, 1985)];
b) [A Textbook of Drug Design and Development, edited by Krogsgaard-Larsen and H. Bundgaard, Chapter 5 "Design and Application of Prodrugs", by H. Bundgaard p. 113-191 (1991)];
c) [H. Bundgaard, Advanced Drug Delivery Reviews, 8, 1-38 (1992)];
d) [H. Bundgaard, et al., Journal of Pharmaceutical Sciences, 77, 285 (1988)]; and
e) [N. Kakeya, et al., Chem Pharm Bull, 32, 692 (1984)].

For example, the prodrug according to the present invention may be one of the following compounds.

relatively low or absorptivity is low. The use of prodrugs may lead to improvement of absorption, distribution, metabolism and excretion (ADME) and PK profile, in addition to increase in solubility and absorptivity.

The compound of the present invention has a chiral center at the C-5 position of an oxazolidinone ring. A preferable diastereoisomer of the oxazolidinone derivative according to the present invention is represented by Formula 1 above and, compared to an epimer represented by Formula 1b below, the diastereoisomer exhibits superior efficacy.

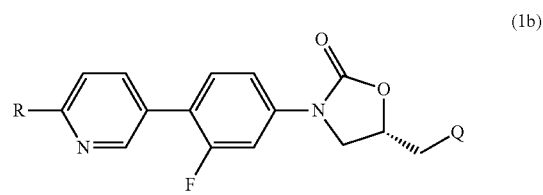

(1b)

When a mixture of epimers of an oxazolidinone chiral center form is used, the amount of mixture used may be adjusted considering the proportion of diastereoisomers in order to attain the same pharmaceutical effect as when a mirror-image isomer is used alone.

The compound of Formula 1 or salt thereof may be tautomerized and thus, although chemical formulae or reaction schemes as used herein represent only one possible tautomer, the present invention is not limited to the one tautomer rep-

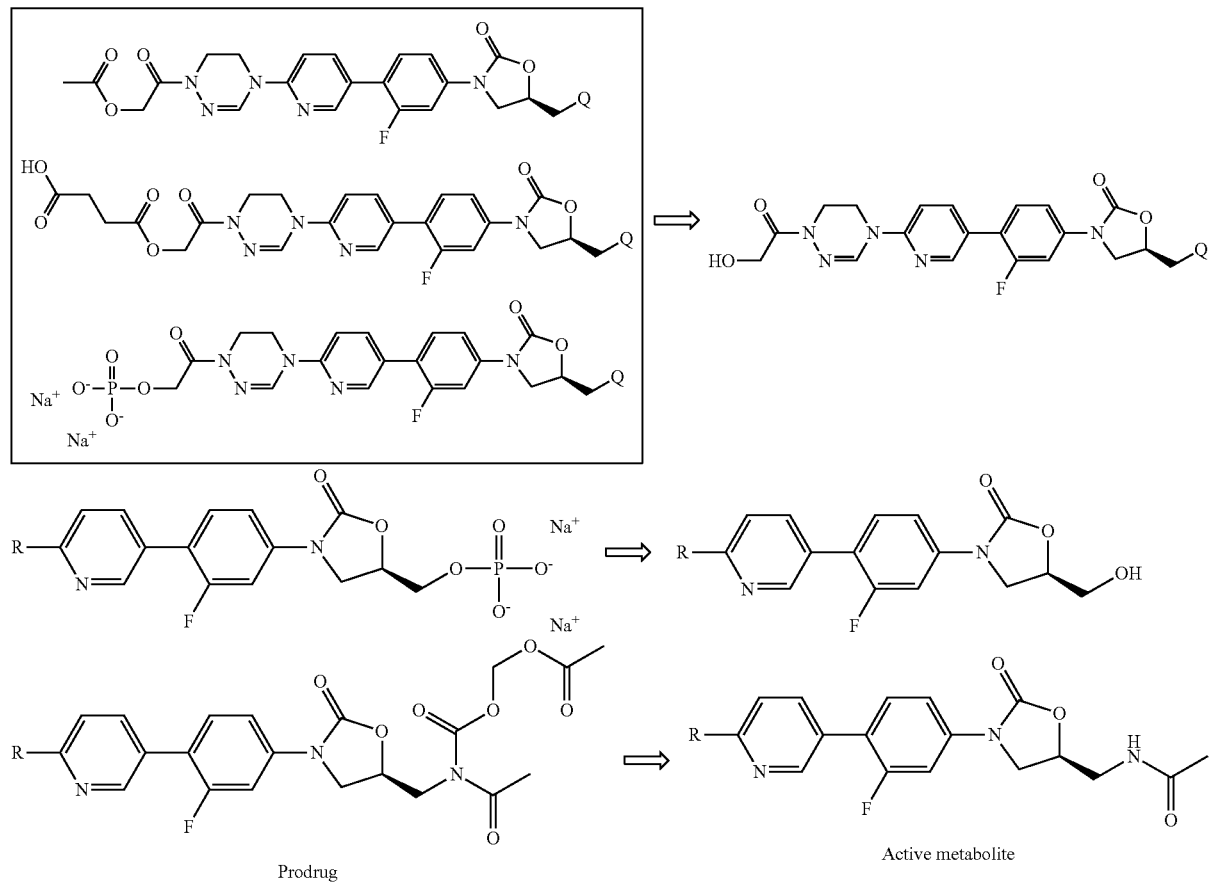

As illustrated in the foregoing examples, a phosphonate or acetyl group may be attached to the hydroxyl group such that the prodrug is transformed into an active metabolite after administration. In another embodiment, an amino acid may be attached or a method of preparing into a carbonate form may be used. Such prodrug is mainly used when solubility is resented by chemical formulas or reaction schemes and arbitrary tautomeric forms having antibacterial activity are also within the scope of the present invention.

In addition, the compound of the present invention may exhibit polymorphism and thus all polymorphic compounds having antibacterial activity are also within the scope of the present invention.

The novel oxazolidinone derivative according to the present invention may be prepared using various known methods depending upon substituents thereof. For example, the oxazolidinone derivative may be prepared using one of the methods illustrated in reaction schemes below. The preparation methods presented in reaction schemes below are provided for illustrative purposes only, and it is obvious that the preparation methods may be easily changed by one of ordinary skill in the art according to particular substituents. Thus, a method of preparing the oxazolidinone compound according to the present invention is not limited to the preparation methods illustrated in reaction schemes below. In addition, unless otherwise specified, definition of substituents in reaction schemes below is the same as defined in Formula 1 above.

Reaction of the oxazolidinone derivatives of Formula 1 is represented by Reaction Scheme 1 below:

As illustrated in Reaction Scheme 1 above, the compound of formula 1 is synthesized through coupling reaction between a bromopyridine part having a cyclic amidoxime or cyclic amidrazone group, i.e., an A part, and a B part having an oxazolidinone group. After the coupling reaction, various derivatives are added to the R' site to convert the R' group into an R group and the Y group is converted into a Q group through reaction of the Y site with various derivatives, thereby completing synthesis of the compound of Formula 1. In addition, the same group as Q defined in Formula 1 above may be introduced into the Y site, and Y may be selected from various reaction intermediate groups including Q. Similarly, R' may also be selected from various reaction intermediate groups including R defined in Formula 1 above.

First, bromopyridine compounds each having a cyclic amidrazone group of the A part of Reaction Scheme 1 may be synthesized according to Reaction Scheme 2 below.

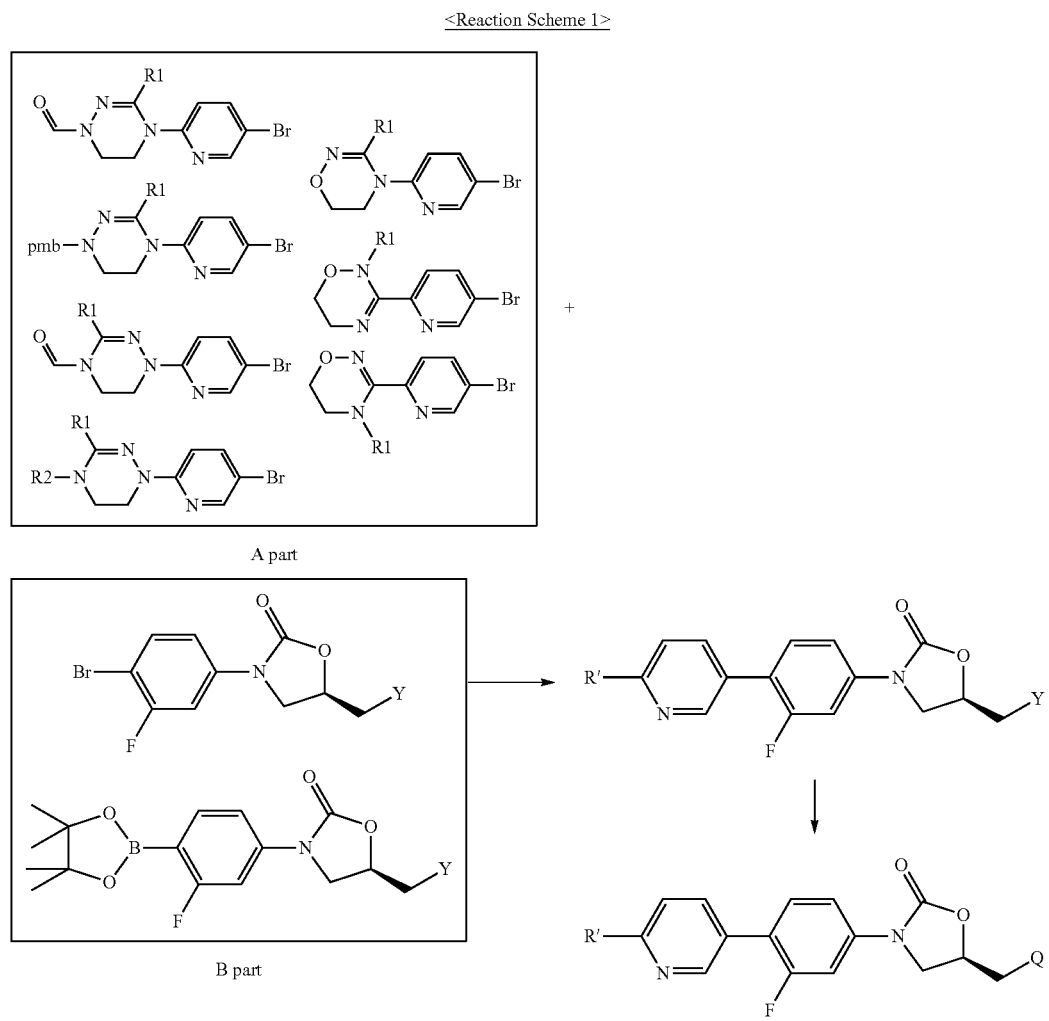

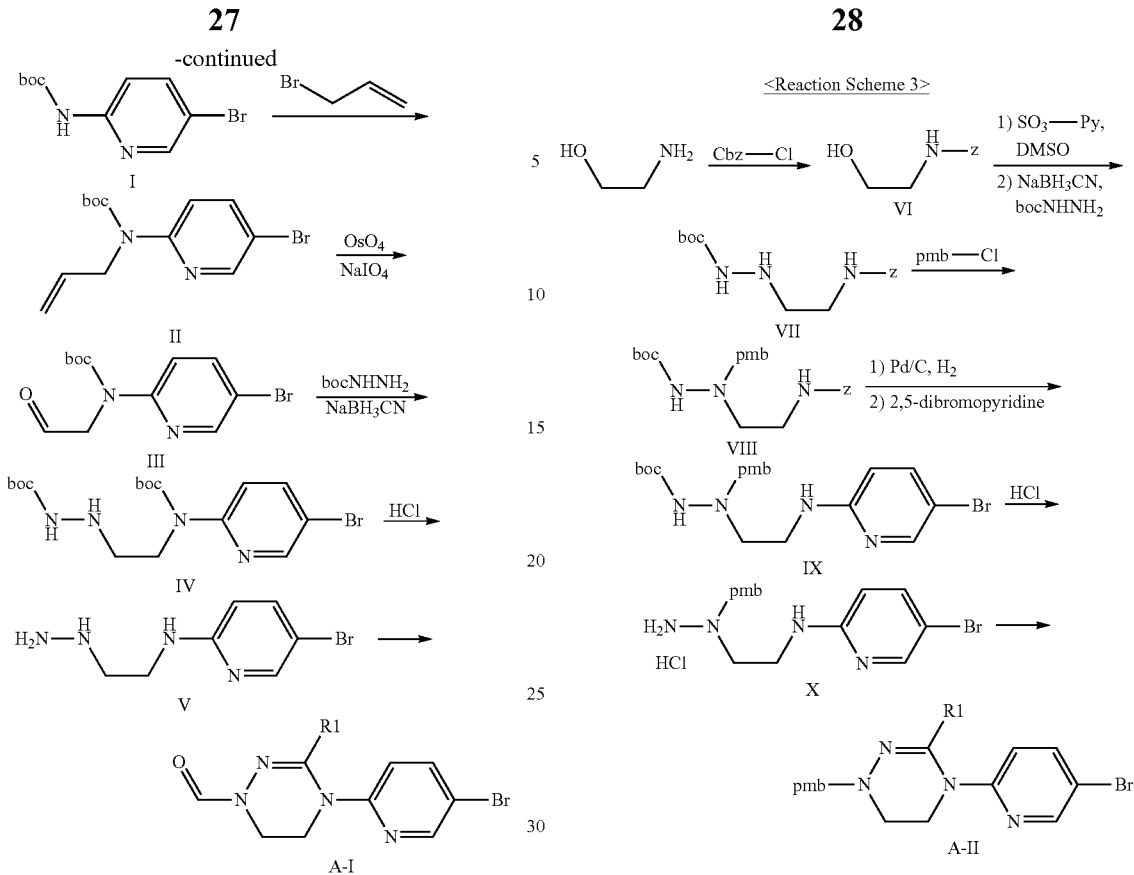

As described in Reaction Scheme 2, Compound I is synthesized by reacting 2-amino-5-bromopyridine with (Boc)$_2$O, and Compound II is synthesized by reacting Compound I with allylbromide. Compound II is made into aldehyde compound III using OsO$_4$ and NaIO$_4$ and then is subjected to reaction with BocNHNH$_2$ to synthesize Compound IV. The synthesized Compound W is treated with acid to obtain Compound V and then is subjected to reaction with orthoester to obtain Compound A-I.

However, the method according to Reaction Scheme 2 involves use of OsO$_4$ that is relatively expensive and has strong toxicity, and thus, another method that does not use OsO$_4$ may be devised and performed according to Reaction Scheme 3 below.

As described in Reaction Scheme 3, ethanolamine is subjected to reaction with Cbz-Cl and then is oxidized with SO$_3$-Py to form an aldehyde, and the aldehyde is subjected to reaction with BocNHNH$_2$ to synthesize Compound VII. Subsequently, Compound VII is subjected to reaction with pmb-Cl to synthesize Compound VIII, and a Cbz group is removed therefrom with Pd/C in the presence of hydrogen and is subjected to reaction with dibromopyridine to obtain Compound IX. Thereafter, Compound IX is treated with hydrochloric acid to obtain Compound X and is subjected to reaction with orthoester to synthesize Compound A-II.

A compound, an amine location of which is different from that of cyclic amidrazone, is synthesized according to Reaction Scheme 4 below.

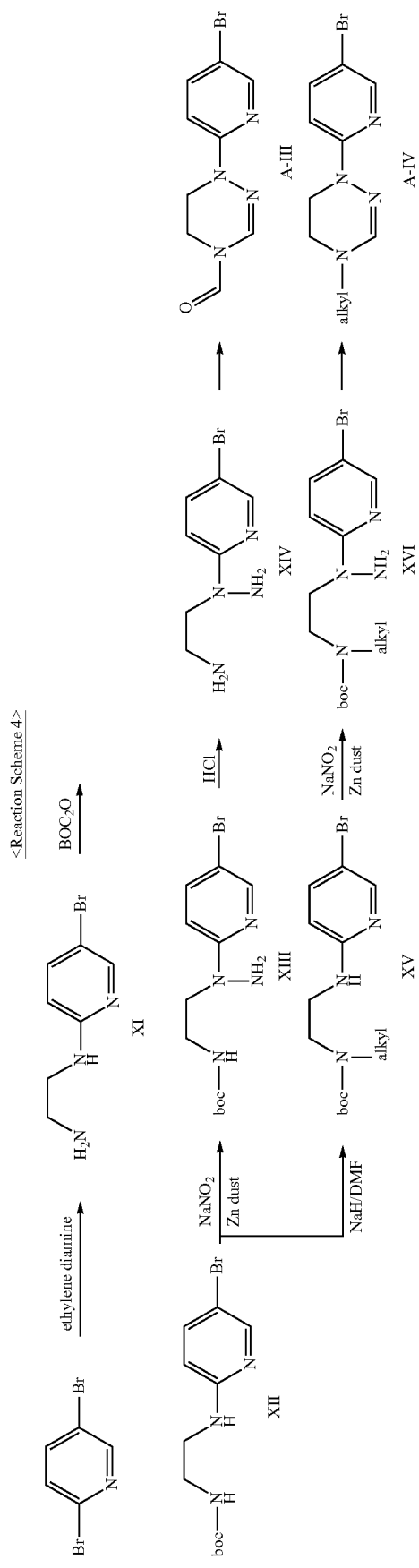

A Boc group is attached to Compound IX obtained by reacting dibromopyridine with ethylenediamine to form Compound XII. Compound XII is subjected to amination with NaNO₂ and Zn, treated with acid, and then subjected to reaction with orthoester to synthesize Compound A-III. As another method, synthesis of a derivative having an alkyl group introduced thereinto is performed such that Compound XII is subjected to alkylation to obtain Compound XV having an alkyl group introduced thereinto and then is subjected to amination and cyclization with orthoester to synthesize Compound A-IV having an alkyl group introduced thereinto.

Synthesis methods of bromopyridine compounds each having a cyclic amidoxime group are represented by Reaction Scheme 5 below.

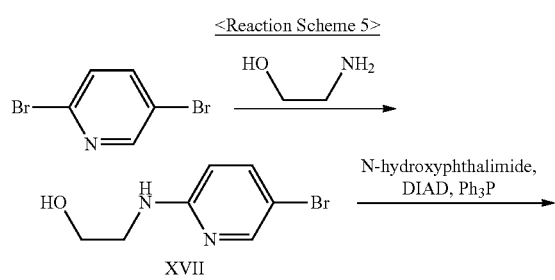

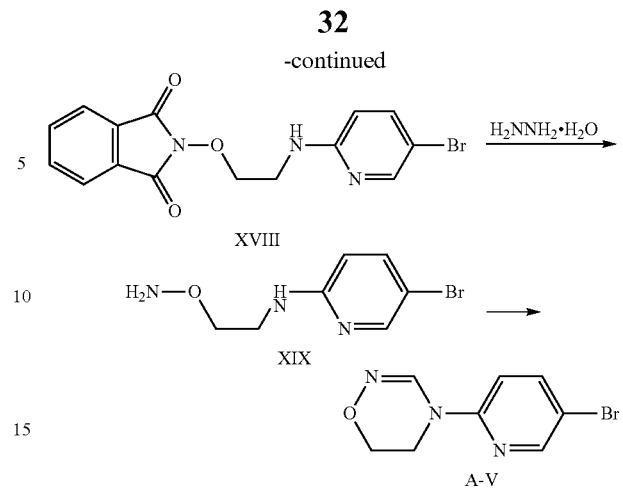

First, Compound XVII is synthesized by reacting dibromopyridine with ethanolamine and then performing Mitsunobu reaction with hydroxyphthalimide to obtain Compound XVIII, the phthalimide group is removed therefrom with hydrazine, and then the resulting compound is subjected to cyclization with orthoester to synthesize Compound A-V.

A synthesis method of a bromopyridine compound having a different type of a cyclic amidoxime group is represented by Reaction Scheme 6.

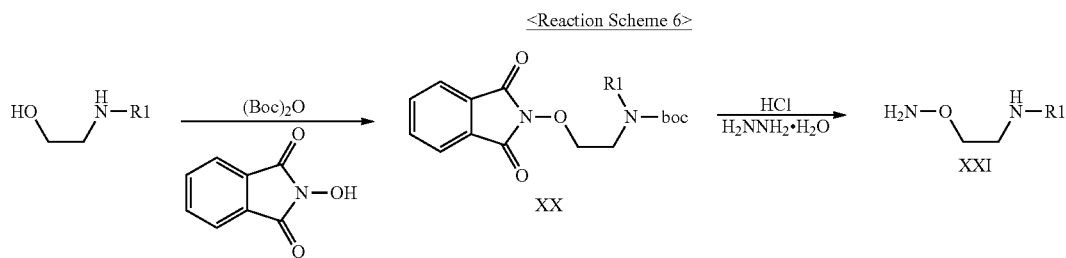

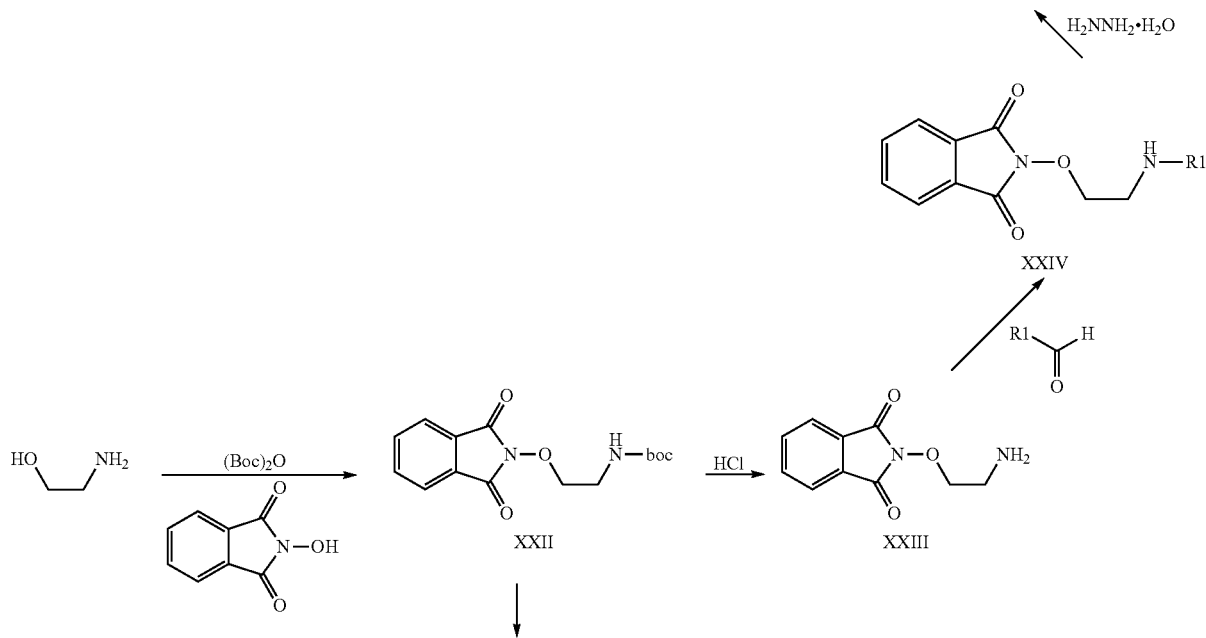

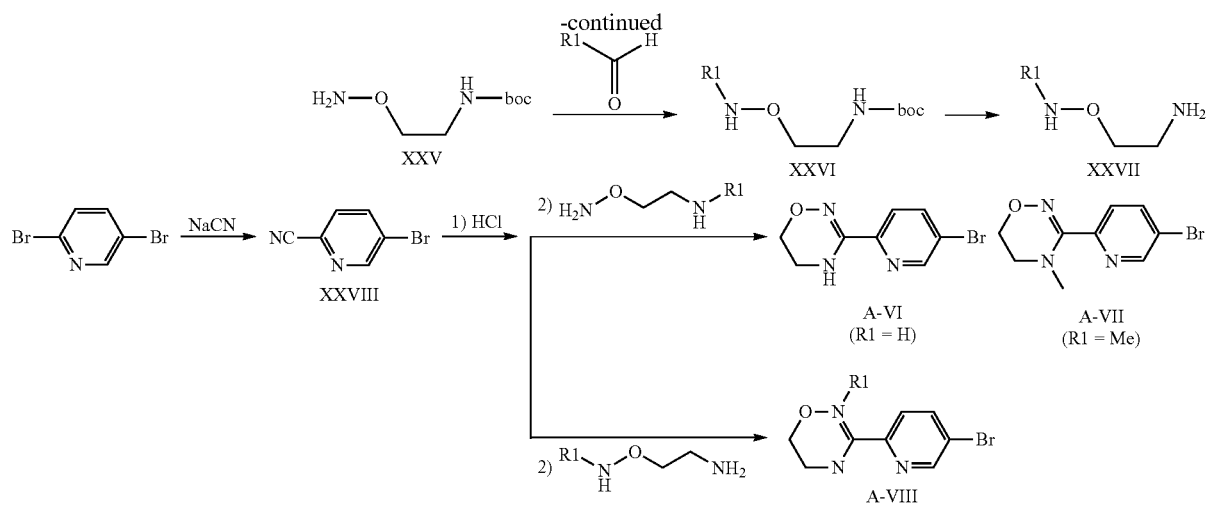

Compound XX is formed by reacting N-alkylethanolamine with Boc$_2$O and then performing Mitsunobu reaction with hydroxyphthalimide, the resulting compound is treated with hydrochloric acid to remove a Boc group, and the phthalimide is removed therefrom with hydrazine to synthesize Compound XXI into which alkyl group R1 is introduced. In addition, as a method of introducing alkyl group R1 afterwards, first, Compound XXII may be formed from ethanolamine through Mitsunobu reaction and then be treated with hydrochloric acid to obtain Compound XXIII, Compound XXIII may be subjected to reaction with aldehyde to form Compound XXIV into which alkyl group R1 is introduced, and then a phthal group may be removed from Compound XXIV with hydrazine to synthesize Compound XXI.

In addition, as synthesis methods of other compounds, an R1 location of which is different from that of the above-described compound, first, a phthal group is removed from Compound XXII with hydrazine and then is subjected to reaction with alkylaldehyde to form Compound XXVI into which an alkyl group is introduced, and the resulting compound is treated with hydrochloric acid to synthesize Compound XXVII from which a Boc group is removed. The obtained Compounds)(XI and XXVII are each subjected to reaction with cyanobromopyridine compound XXVIII to synthesize Compounds A-VI, A-VII and A-VIII. Meanwhile, compounds of Formula 1, wherein R$_1$ is hydrogen, may not be subjected to reaction with alkylaldehyde to obtain each resulting compound.

In Reaction Scheme 1 above, synthesis methods of compounds of the B part having an oxazolidinone group are represented by Reaction Scheme 7 below.

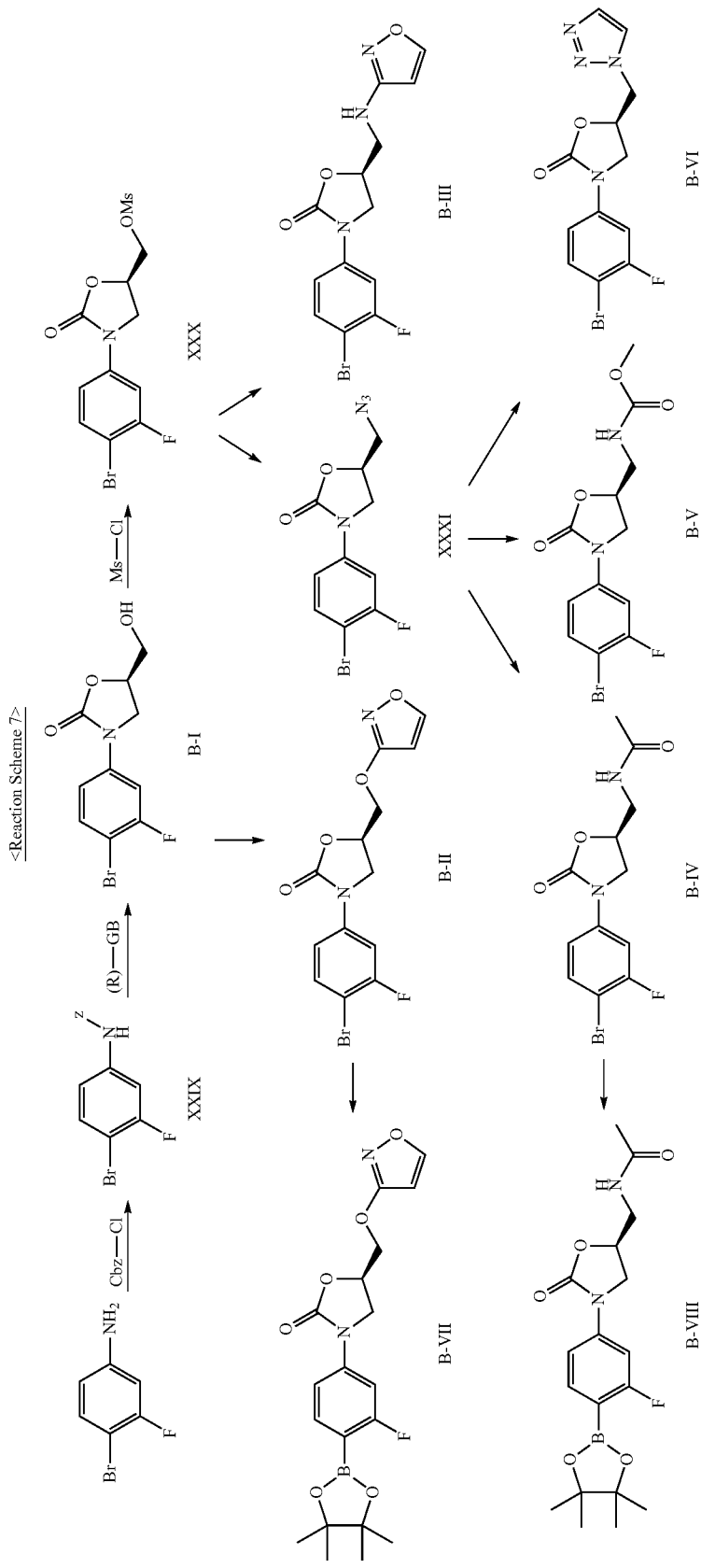

Compound XXIX is obtained by reacting 3-fluoro-4-bromoaniline with Cbz-Cl and then reaction with (R)-glycidyl butyrate to synthesize chiral Compound B-I. Alcohol of Compound B-I is converted into various kinds of derivative compounds Y to synthesize Compounds B-II, B-IV, B-V and B-VI, followed by coupling with the A part, or bromine of Compound B-I is converted into pinacolborane to obtain Compound B-VII and then is subjected to coupling, thereby completing synthesis of the compound of Formula 1.

The present invention also provides a pharmaceutical composition for an antibiotic which includes: (a) a therapeutically effective amount of the novel oxazolidinone derivative of Formula 1, a prodrug thereof, a hydrate thereof, a solvate thereof, an isomer thereof, or a pharmaceutically acceptable salt thereof; and (b) a pharmaceutically acceptable carrier, a diluent, an excipient, or a combination thereof.

The term "pharmaceutical composition" as used herein means a mixture of the compound according to the present invention and other chemical components such as a diluent or a carrier. The pharmaceutical composition facilitates administration of the compound to an organism. Administration of the compound may be performed using various methods. Examples of various administration methods include, but are not limited to, oral administration, injection, aerosol administration, parenteral administration, and local administration. The pharmaceutical composition may be obtained through reaction with an acid such as hydrochloric acid, bromic acid, sulfuric acid, nitric acid, phosphoric acid, methanesulfonic acid, p-toluenesulfonic acid, salicylic acid, or the like.

As used herein, the term "therapeutically effective amount" means an effective amount of an active ingredient of the pharmaceutical composition to alleviate or reduce one or more symptoms of disorders treated by the composition or to delay initiation of clinical markers or symptoms of diseases needed for prevention. Thus, the therapeutically effective amount means an amount that has the effect of: (1) reversing progression rate of diseases, (2) inhibiting further progression of diseases to some extent, and/or (3) alleviating (preferably, eliminating) one or more symptoms related to diseases to some extent. The therapeutically effective amount may be experientially determined through experiment of a compound in a known in vivo and in vitro model system for diseases needed for treatment.

The term "carrier" is defined as a compound that facilitates delivery of a compound into cells or tissues. For example, dimethyl sulfoxide (DMSO) is a commonly used carrier that facilitates introduction of many organic compounds into cells or tissues of an organism.

The term "diluent" is defined as a compound that stabilizes a biologically active form of a target compound and is diluted in water used to dissolve the compound. Salts dissolved in buffer solutions are used as diluents in the art. A commonly used buffer solution is phosphate buffered saline because it has similar salanity to the human body. Buffer salts can control pH of a solution at low concentrations and thus a buffered diluent rarely modifies biological activity of a compound.

The compound used may be administered alone to a patient, or be administered to a patient as a pharmaceutical composition prepared by mixing the compound with other active ingredients or with an appropriate carrier or excipient as in combination therapy. Techniques for formulation and administration of the compound of the present application can be found in "Remington's Pharmaceutical Sciences," Mack Publishing Co., Easton, Pa., 18th edition, 1990.

The pharmaceutical composition of the present invention may be prepared in a known manner by methods such as conventional mixing, dissolution, granulation, dragee making, levigating, emulsification, encapsulation, trapping, or lyophilization.

Thus, pharmaceutical compositions for use in accordance with the present invention may be prepared in a conventional manner using one or more pharmaceutically acceptable carriers including excipients or auxiliary agents which facilitate processing of active compounds into formulations for pharmaceutical use. Proper formulation is dependent upon route of administration selected. Any suitable well-known techniques, carriers, and excipients may be used as understood in the art, e.g., Remingston's Pharmaceutical Sciences described above. The compound of formula 1 according to the present invention may be formulated for injection, oral administration, or the like according to intended application.

For injection, the composition of the present invention may be formulated as an aqueous solution, preferably a physiologically acceptable buffer such as Hank's solution, Ringer's solution, or physiological saline buffer. For transmucosal administration, non-invasive agents suitable for a barrier through which the composition passes are used in formulation. Such non-invasive agents are generally known in the art.

For oral administration, the compounds may be formulated by combining active compounds with pharmaceutically acceptable carriers known in the art. Such carriers enable the compounds of the present invention to be formulated as tablets, pills, powders, granules, dragees, capsules, liquids, gels, syrups, slurries, suspensions, and the like. Capsules, tablets, pills, powders, and granules are preferable and, in particular, capsules and tablets may be used. Tablets and pills may be prepared with enteric coatings. Pharmaceutical preparations for oral use may be obtained by mixing one or more solid excipients with one or more compounds of the invention, optionally grinding the resulting mixture, and processing the mixture of granules, after adding suitable auxiliary agents, if desired, to obtain tablets or dragee cores. Suitable excipients include, in particular, fillers such as lactose, sucrose, mannitol, or sorbitol; cellulose-based materials such as maize starch, wheat starch, rice starch, potato starch, gelatin, gum tragacanth, methyl cellulose, hydroxypropylmethyl-cellulose, sodium carboxymethyl cellulose, and/or polyvinylpyrrolidone (PVP). If desired, disintegrating agents such as cross-linked polyvinyl pyrrolidone, agar, or alginic acid or a salt thereof such as sodium alginate, lubricants such as magnesium stearate, and carriers such as binders and the like may be added.

Pharmaceutical preparations which can be orally administered include push-fit capsules made of gelatin, as well as soft, sealed capsules made of gelatin and a plasticizer, such as glycerol or sorbitol. The push-fit capsules may contain active ingredients in admixture with a filler such as lactose, a binder such as starch, and/or a lubricant such as talc or magnesium stearate. In soft capsules, the active compounds may be dissolved or suspended in suitable liquids, such as fatty oils, liquid paraffin, or liquid polyethylene glycol. In addition, stabilizers may be added. All formulations for oral administration should be in dosages suitable for such administration.

The compounds may be formulated for parenteral administration by injection, e.g., by bolus injection or continuous infusion. Formulations for injection may be provided in unit dosage form, e.g., in ampoules or in multi-dose containers, with an added preservative. The compositions may take such forms as suspensions, solutions or emulsions in oily or aqueous vehicles, and may contain agents for formulation such as suspending, stabilizing and/or dispersing agents.

In addition, the compounds may be in dried powder form that is used after being dissolved in sterile pyrogen-free water.

The compounds may be formulated as suppositories including conventional suppository materials such as cacao butter or other glycerides or as compositions for rectal administration, such as retension enema.

Pharmaceutical compositions suitable for use in the present invention include compositions where the active ingredients are contained in an amount effective to achieve its intended purpose. More specifically, a therapeutically effective amount means an amount of compound effective to extend the survival, of a subject to be treated or to prevent, alleviate or ameliorate symptoms of diseases. Determination of the therapeutically effective amount may be within the capacity of one of ordinary skill in the art, in particular, in terms of the detailed description provided herein.

When formulated in a unit dosage form, the pharmaceutical composition may include the compound of Formula 1 as an active ingredient in a unit dosage of approximately 0.1 to 1,500 mg. A suitable dose of the compound of Formula 1 is given in accordance with the prescription of doctors depending upon factors, such as body weights and ages of patients and particular properties and severity of diseases. However, the formulated compound may be administered once to three times per day for treatment of adults according to frequency and intensity of administration and a dose thereof is generally in the range of about 1 to about 1,500 mg. When administered to an adult muscularly or intravenously, the pharmaceutical composition may be administered once to three times per day and a dose thereof may be generally about 1 to about 1,500 mg. For some patients, however, a higher dose may be used.

The pharmaceutical composition of the present invention may be formulated together with at least one known drug selected from clinically useful antibacterial agents (e.g., β-lactam, macrolide, quinolone, and aminoglycoside) and anti-inflammatory agents (e.g., antifungal triazole or amphotericin), or may be co-administered with one or more known drugs. The compound of the present invention may be formulated together with or co-administered with a bactericidal/permeability increasing protein (BPI) or an efflux pump inhibitor, in order to increase activity against Gram-negative bacteria and antibiotic resistant bacteria.

The compound of the present invention may be formulated together with or co-administered with vitamins, e.g., vitamin B2, vitamin B6, or vitamin B12, and folic acid. The compound of the present invention may be formulated together with or co-administered with a cyclooxygenase (COX) inhibitor, particularly a COX-2 inhibitor.

The present invention also provides an antibiotic treatment method performed using an effective amount of a novel oxazolidinone derivative represented by Formula 1 above, a prodrug thereof, a hydrate thereof, a solvate thereof, an isomer thereof, or a pharmaceutically acceptable salt thereof.

BEST MODE

Now, the present invention will be described in more detail with reference to the following examples. These examples are provided only for illustration of the present invention and should not be construed as limiting the scope and spirit of the present invention.

To synthesize the compound of Formula 1, first, synthesis of the A part and the B part was performed according to preparation examples below.

Preparation Example 1

Preparation of Compound I

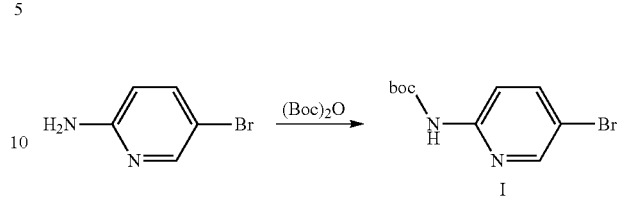

10 g (57.80 mmol) of 2-amino-5-bromopyridine, 17.4 mL (124.47 mmol) of triethylamine, 16.3 g (74.75 mmol) of ditertbutyldicarbonate, and 0.5 g (4.05 mmol) of dimethylaminopyridine were added to 270 mL of dichloromethane at 0° C. and the resulting solution was stirred for 3 hours.

The reaction mixture was dissolved in 300 mL of dichloromethane and then washed with 200 mL of an aqueous saturated sodium bicarbonate solution, and the resulting solution was dehydrated using anhydrous sodium sulfate, followed by concentration under reduced pressure and column chromatography, to obtain 9.8 g (36.21 mmol) of Compound I as a yellow solid (yield: 63%).

$^1$H NMR (600 MHz, CDCl$_3$) δ 8.32 (d, J=2.4 Hz, 1H), 7.97 (s, 1H), 7.90 (d, J=9.0 Hz, 1H), 7.75 (dd, J$_1$=9.0 Hz, J$_2$=2.4 Hz, 1H), 1.55 (s, 9H)

Preparation Example 2

Preparation of Compound II

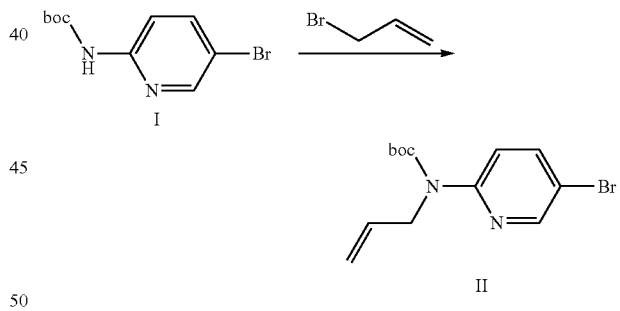

9.89 g (36.21 mmol) of Compound 1.20 g (43.45 mmol) of cesiumcarbonate, and 3.76 mL (43.45 mmol) of allyl bromide were added to 200 mL of dimethylformamide at room temperature and the resulting solution was stirred at 70° C. for 2.5 hours.

The reaction mixture was cooled to 0° C., 200 mL of distilled water was slowly added thereto, and the resulting solution was diluted with 600 mL of ethylacetate and then sequentially washed with 500 mL of distilled water, 250 mL of 0.5N HCl, and 200 mL of an aqueous saturated sodium chloride solution. Thereafter, the resultant solution was dehydrated using anhydrous sodium sulfate and concentrated under reduced pressure to obtain 11 g (35.12 mmol) of Compound II as a yellow oil (yield: 97%).

¹H NMR (600 MHz, CDCl₃) δ 8.38 (d, J=1.8 Hz, 1H), 7.70 (dd, J₁=8.4 Hz, J₂=2.4 Hz, 1H), 7.66 (d, J=8.4 Hz, 1H), 5.93 (m, 1H), 5.12 (m, 2H), 4.53 (m, 2H) 1.50 (s, 9H)

Preparation Example 3

Preparation of Compound IV

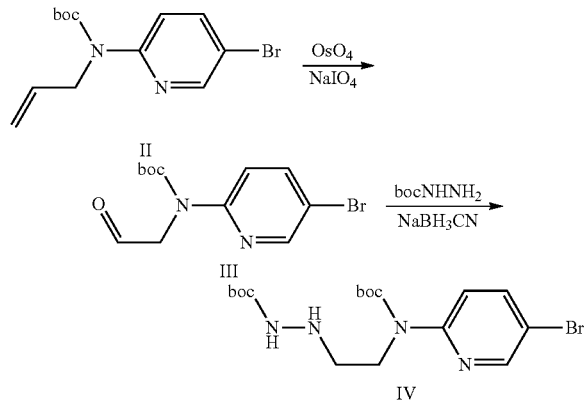

11 g (35.12 mmol) of Compound II, 11 mL (0.88 mmol) of OsO₄, and 30 g (140.48 mmol) of NaIO₄ were sequentially added at 0° C., the resulting solution was stirred at 0° C. for 5 hours, 7 g (32.73 mmol) of NaIO₄ was further added thereto, and the resultant solution was stirred for 1 hour. The reaction mixture was filtered and washed with 300 mL of ethylacetate. An organic layer was washed with 300 mL of distilled water, hydrated with anhydrous sodium sulfate and then concentrated under reduced pressure to obtain 14.19 g of Compound III as a brown oil.

14.19 g of the obtained Compound III, 12.87 g (97.50 mmol) of BocNHNH₂, 3.34 g (53.16 mmol) of sodium cyanoborohydride, and 2.1 mL (35.44 mmol) of acetic acid were sequentially added at 0° C., and the resulting solution was stirred at room temperature for 3 hours. Sequentially, 150 mL of distilled water was added to the reaction mixture, and the resultant solution was stirred at room temperature for 20 minutes and then extracted with 500 mL of ethylacetate and 300 mL of an aqueous sodium bicarbonate solution. Thereafter, a water layer was washed with 300 mL of ethylacetate, dehydrated with anhydrous sodium sulfate and then concentrated under reduced pressure. The concentrate was subjected to column chromatography to obtain 10.92 g (25.32 mmol) of Compound IV as an oil (yield: 72%).

¹H NMR (600 MHz, CDCl₃) δ 8.39 (d, J=2.4 Hz, 1H), 7.71 (dd, J₁=9.0 Hz, J₂=2.4 Hz, 1H), 7.60 (d, J=9.0 Hz, 1H), 6.52 (s, 1H), 4.01 (m, 1H), 4.03 (t, J=6.0 Hz, 2H), 3.07 (t, J=6.0 Hz, 2H) 1.52 (s, 9H), 1.46 (s, 9H)

Preparation Example 4

Preparation of Compound A-I

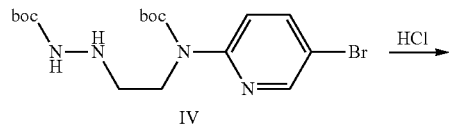

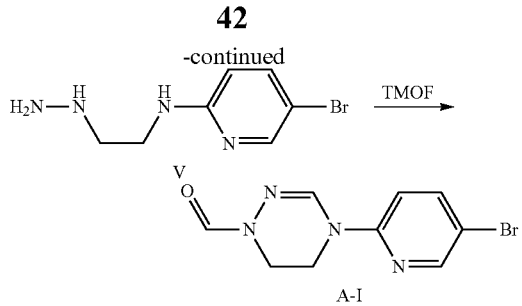

10.92 g (25.32 mmol) of Compound VI was added to 70 mL of methanol, 120 mL of 4M HCl was added thereto, the resulting solution was stirred at room temperature for 12 hours, and the stirred solution was concentrated under reduced pressure. 7.5 g of the obtained Compound V, 40 mL of trimethylorthoformate, and 3.91 g (47.68 mmol) of sodium acetate were added to 40 mL of acetic acid, and the resulting solution was refluxed by stirring for, 4 hours. The compound was cooled to room temperature and then concentrated under reduced pressure, 300 mL of dichloromethane was added thereto, and the resultant solution was washed twice with 300 mL of an aqueous saturated sodium bicarbonate solution, dehydrated with anhydrous sodium sulfate and then concentrated under reduced pressure to obtain 5.9 g (22.03 mmol) of Compound A-I as a yellow solid (yield: 87%).

¹H NMR (600 MHz, CDCl₃) δ 8.59 (s, 1H), 8.37 (d, J=2.4 Hz, 1H), 7.82 (s, 1H), 7.78 (dd, J₁=9.0 Hz, J₂=2.4 Hz, 1H), 6.80 (d, J=9.0 Hz, 1H), 4.00 (t, J=5.4 Hz 2H), 3.85 (t, J=5.4 Hz, 2H)

Preparation Example 5

Preparation of Compound VI

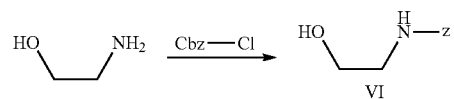

32 g (527.5 mmol) of 2-aminoethanol was dissolved in 250 mL of dichloromethane, 300 mL of an aqueous 1N NaOH solution was added thereto, and 60 g (351.7 mmol) of Cbz-Cl (benzyl chloroformate) was slowly added dropwise while the resulting solution was stirred. The resultant solution was stirred at room temperature for 2 hours, an organic layer was separated therefrom and washed twice with water, and the washed organic layer was dehydrated using anhydrous sodium sulfate and concentrated under reduced pressure to obtain 62 g (317.6 mmol) of Compound VI as a white solid (yield: 90%).

¹H NMR (600 MHz, CDCl₃) δ 7.36 (m, 5H), 5.15 (s, 1H), 5.11 (s, 2H), 3.73 (m, 2H), 3.37 (m, 2H), 2.08 (s, 1H)

Preparation Example 6

Preparation of Compound VII

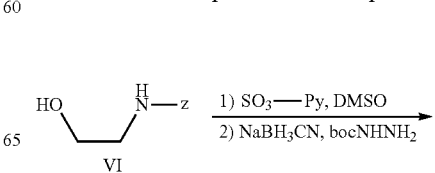

-continued

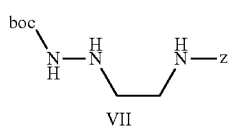

VII 30 g (153.7 mmol) of Compound VI, 49 g (307.4 mmol) of sulfone trioxide, 86 mL (614.4 mmol) of triethylamine, and 120 mL of DMSO were added to 250 mL of dichloromethane at 0° C., and the resulting solution was stirred at room temperature for 2 hours. Thereafter, 1000 mL of diethylether was added to the reaction mixture, and the resultant solution was sequentially washed with 500 mL of distilled water, 800 mL of 0.5N HCl, and 500 mL of distilled water, dehydrated with anhydrous sodium sulfate, and then concentrated under reduced pressure.

The obtained aldehyde compound was dissolved in 300 mL of methanol, 22 g (169.0 mmol) of tertbutylchabazite, 11.6 g (184.4 mmol) of sodiumcyanoborohydride, and 11 mL (184.4 mmol) of acetic acid were sequentially added thereto at 0° C., and then the resulting solution was stirred at room temperature for 12 hours. Thereafter, 11 mL (184.4 mmol) of acetic acid was added to the reaction mixture, and the resultant solution was concentrated under reduced pressure, extracted using 800 mL of ethylacetate and 500 mL of an aqueous saturated sodium bicarbonate solution, and then subjected to column chromatography to obtain 25 g (80.8. mmol) of Compound VII as a brown oil (yield: 53%).

$^1$H NMR (600 MHz, CDCl$_3$) δ 7.32 (m, 5H), 6.17 (s, 1H), 5.47 (s, 1H), 5.14 (s, 1H), 5.10 (s, 2H), 3.29 (m, 2H), 2.90 (m, 2H), 1.45 (s, 9H)

Preparation Example 7

Preparation of Compound VIII

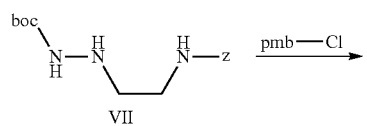

25 g (80.8 mmol) of Compound VII, 32 g (200 mmol) of paramethoxybenzylchloride, and 43 mL (243 mmol) of diisopropylethylamine were added to 50 mL of dimethylformamide, and the resulting solution was stirred at 80° C. for 5 hours. Subsequently, 500 mL of ethylacetate was added to the reaction mixture, the resultant solution was sequentially washed with 500 mL of distilled water and 500 mL of an aqueous saturated sodium bicarbonate solution, and the washed solution was dehydrated using anhydrous sodium sulfate, concentrated under reduced pressure, and then subjected to column chromatography to obtain 19 g (44.0 mmol) of Compound VIII as a brown oil.

$^1$H NMR (600 MHz, CDCl$_3$) δ 7.35 (m, 5H), 7.25 (d, J=8.4 Hz, 2H), 6.87 (d, J=8.4 Hz, 2H), 5.99 (s, 1H), 5.38 (s, 1H), 3.92 (s, 2H), 3.81 (s, 3H), 3.29 (m, 2H), 2.79 (m, 2H), 1.40 (s, 9H)

Preparation Example 8

Preparation of Compound IX

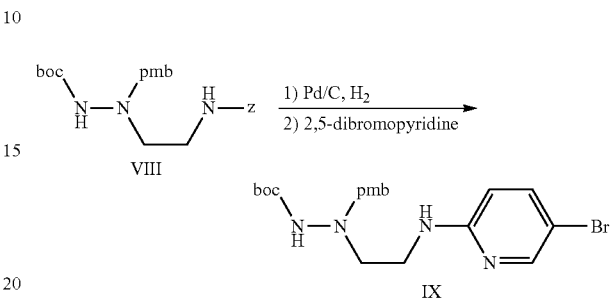

12 g (27.9 mmol) of Compound VIII and 1.2 g of Pd/C were added to 200 mL of ethanol, the resulting solution was stirred in a hydrogen gas balloon for 1 hour, the stirred solution was filtered through celite and then concentrated under reduced pressure, 13.3 g (55.87 mmol) of 2,5-dibromopyridine was added thereto, and the resultant solution was stirred at 140° C. for 1 hour. The reaction mixture was dissolved in 200 mL of dichloromethane and then washed with 50 mL of saturated sodium bicarbonate. Thereafter, the washed solution was dehydrated using anhydrous sodium sulfate and then concentrated under reduced pressure, and the concentrate was subjected to column chromatography to obtain 4.2 g (9.3 mmol) of Compound IX as a brown oil (yield: 33%).

$^1$H NMR (600 MHz, CDCl$_3$) δ 8.07 (s, 1H), 7.43 (d, J=7.8 Hz, 1H), 7.23 (d, J=8.4 Hz, 2H), 6.85 (d, J=8.4 Hz, 2H), 6.42 (d, J=7.8 Hz, 1H), 5.72 (s, 1H), 5.39 (s, 1H), 3.92 (s, 2H), 3.82 (s, 3H), 3.40 (m, 2H), 2.88 (m, 2H), 1.40 (s, 9H)

Preparation Example 9

Preparation of Compound A-II

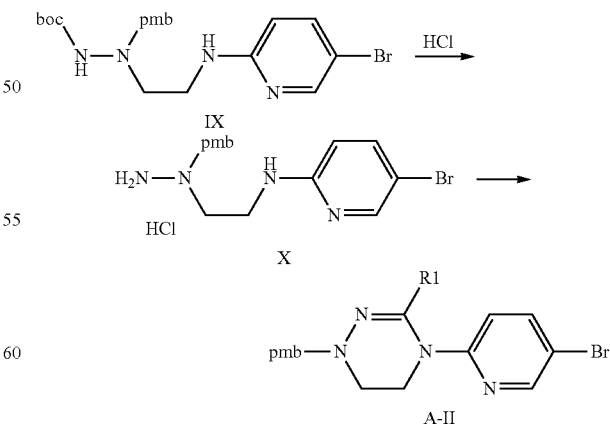

3 g (6.6 mmol) of Compound IX and 15 mL of 4M HCl were added to 15 mL of dichloromethane, the resulting solution was stirred at room temperature for 2 hours, and the stirred solution was concentrated under reduced pressure to obtain Compound X as an HCl salt from which the Boc group is removed.

Subsequently, 10 mL of trimethoxyorthoformate and 20 mL of acetic acid were added to the obtained Compound X, and the resultant solution was refluxed by stirring for 2 hours. The reaction mixture was concentrated under reduced pressure and then extracted using 150 mL of ethylacetate and 50 mL of an aqueous saturated sodium bicarbonate solution. Thereafter, the extract was dehydrated using anhydrous sodium sulfate and then subjected to column chromatography to obtain 1 g (2.8 mmol) of Compound A-II as an ivory solid (yield: 42%).

$^1$H NMR (600 MHz, CDCl$_3$) δ 8.29 (d, J=3.0 Hz, 1H), 7.87 (s, 1H), 7.67 (dd, J$_1$=9.0 Hz J$_2$=2.4 Hz, 1H), 7.32 (d, J=8.4 Hz, 2H), 6.89 (d, J=8.4 Hz, 2H), 6.65 (d, J=9.0 Hz, 1H), 4.09 (s, 2H), 3.81 (s, 3H), 3.79 (t, J=5.4 Hz, 2H), 2.92 (t, J=5.4 Hz, 2H)

Preparation Example 10

Preparation of Compound XI

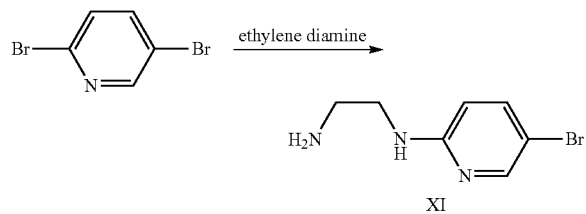

1 g (4.22 mmol) of 2,5-dibromopyridine was added to 10 mL of ethylenediamine, and the resulting solution was stirred at 100° C. for 15 hours. The reaction mixture was cooled to room temperature and concentrated under reduced pressure to remove ethylenediamine. Thereafter, 50 mL of dichloromethane was added to dilute the concentrate, the diluted solution was washed with 30 mL of distilled water, and then 50 mL of dichloromethane was added to the collected distilled water to extract an organic layer therefrom, these processes were repeated twice more. The combined organic layers were dehydrated using anhydrous sodium sulfate, followed by concentration under reduced pressure, to obtain 0.89 g (4.12 mmol) of Compound XI as a light yellow liquid (yield: 98%).

$^1$H NMR (400 MHz, CDCl$_3$) δ 8.10 (d, J=1.6 Hz, 1H), 7.45 (dd, J$_1$=8.8 Hz, J$_2$=2.4 Hz, 1H), 6.33 (d, J=8.8 Hz), 4.95 (brs, 1H), 3.34 (q, J=6 Hz, 2H), 2.94 (t, J=6 Hz, 2H)

Preparation Example 11

Preparation of Compound XII

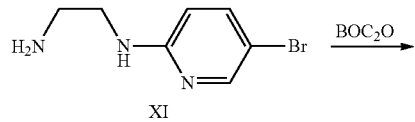

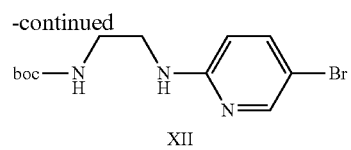

0.89 g (4.12 mmol) of Compound XI was dissolved in 10 mL of 1,4-dioxane, the resulting solution was cooled to 0° C., 0.44 g (4.12 mL) of sodium carbonate dissolved in 20 mL of distilled water was added thereto, and 0.99 mL (4.32 mmol) of ditertbutyldicarbonate dissolved in 5 mL of 1,4-dioxane was slowly added dropwise to the resultant solution. Subsequently, the temperature of the reaction mixture was raised to room temperature, the reaction mixture was stirred for 15 hours and then concentrated under reduced pressure to remove 1,4-dioxane, 2N hydrochloric acid was slowly added thereto at 0° C. to reduce pH thereof to 4, and the resulting solution was extracted using 250 mL of ethylacetate to obtain an organic layer. The organic layer was dehydrated using anhydrous sodium sulfate and then concentrated under reduced pressure to obtain a solid product. The solid product was washed with 30 mL of n-hexane to obtain 1.28 g (4.05 mmol) of Compound XII as a light yellow solid (yield: 98%).

$^1$H NMR (400 MHz, CDCl$_3$) δ 8.09 (d, J=1.6 Hz, 1H), 7.44 (dd, J$_1$=8.8 Hz, J$_2$=2.4 Hz, 1H), 6.33 (d, J=8.8 Hz, 1H), 4.94 (brs, 1H), 3.44 (m, 2H), 3.35 (m, 2H), 1.44 (s, 9H)

Preparation Example 12

Preparation of Compound XIII

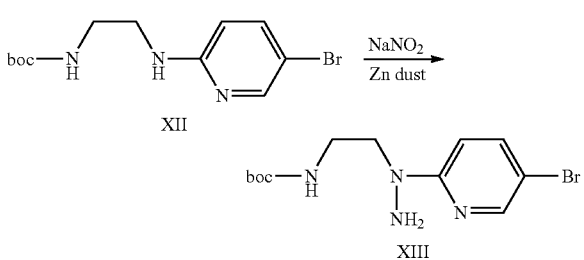

0.5 g (1.58 mmol) of Compound XII was dissolved in 6 mL of acetic acid, the resulting solution was cooled to 0° C., and 0.11 g (1.66 mmol) of sodium nitrite dissolved in 2 mL of distilled water was slowly added dropwise thereto. The reaction temperature was raised from 0° C. to room temperature, the resultant solution was stirred for 30 minutes, the temperature thereof was lowered again to 0° C., and 0.21 g (3.16 mmol) of zinc was added to the resultant solution and then was further stirred for 1 hour. The stirred solution was neutralized at 0° C. using 50 mL of distilled water and saturated sodium bicarbonate, 0.4 mL of 4M hydrochloric acid dissolved in 1,4-dioxane was added thereto, the resulting solution was extracted with 50 mL of ethylacetate, and the extract was dehydrated using anhydrous sodium sulfate and then concentrated under reduced pressure to obtain 0.41 g (1.23 mmol) of Compound XIII as a reddish brown solid (yield: 79%).

$^1$H NMR (600 MHz, CDCl$_3$) δ 8.18 (m, 1H), 7.65 (m, 2H), 7.15 (m, 1H), 5.80 (brs, 1H), 4.04 (m, 2H), 3.57 (m, 2H), 1.32 (s, 9H)

Preparation Example 13

Preparation of Compound XIV

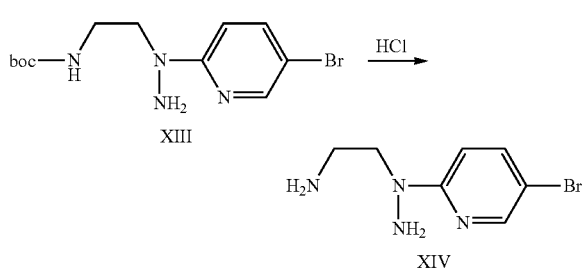

0.4 g (1.20 mmol) of Compound XIII was dissolved in 3 mL of dichloromethane, the resulting solution was cooled to 0° C., and 0.4 mL of 4M hydrochloric acid dissolved in 1,4-dioxane was added dropwise thereto under a nitrogen atmosphere. Subsequently, the resultant solution was stirred for 15 hours and then concentrated under reduced pressure to obtain a solid product. The solid product was washed with 20 mL of diethylether to obtain 0.28 g (0.97 mmol) of Compound XIV as a light yellow solid (yield: 80%).

$^1$H NMR (600 MHz, CD$_3$OD) δ 8.20 (d, J=2.4 Hz, 1H), 8.12 (dd, J$_1$=9.6 Hz, J$_2$=2.4 Hz, 1H), 7.30 (d, J=9.6 Hz, 1H), 4.06 (t, J=6.6 Hz, 2H), 3.40 (t, J=6.6 Hz, 2H)

Preparation Example 14

Preparation of Compound A-III

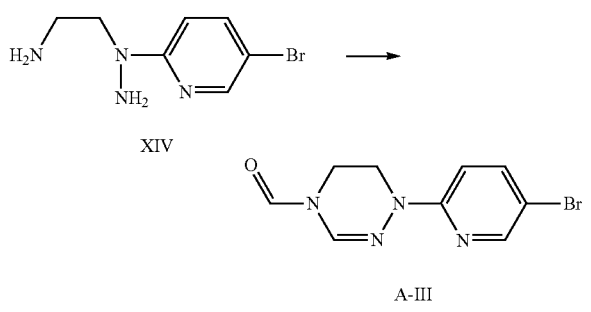

710 mg (2.45 mmol) of Compound XIV and 2 mL of trimethylorthoformate were added to 8 mL of acetic acid, and the resulting solution was refluxed by stirring for 5 hours. Subsequently, the reaction mixture was cooled to room temperature and then concentrated under reduced pressure to remove solvent, 10 mL of distilled water was added thereto, and the resulting concentrate was extracted using 20 mL of dichloromethane. Thereafter, 20 mL of dichloromethane was added to the extracted distilled water and reextracted to obtain an organic layer. The organic layer was dehydrated using anhydrous sodium sulfate, concentrated under reduced pressure, and then subjected to column chromatography to obtain 290 mg (1.07 mmol) of Compound A-III as a light yellow solid (yield: 44%).

$^1$H NMR (400 MHz, CDCl$_3$) δ 8.49 (s, 1H), 8.20 (s, 1H), 7.65 (dd, J$_1$=9.2 Hz, J$_2$=2.4 Hz, 1H), 7.33 (d, J=9.0 Hz, 1H), 7.24 (s, 1H), 4.07 (t, J=5.2 Hz, 2H), 3.90 (t, J=5.2 Hz, 2H)

Preparation Example 15

Preparation of Compound XV

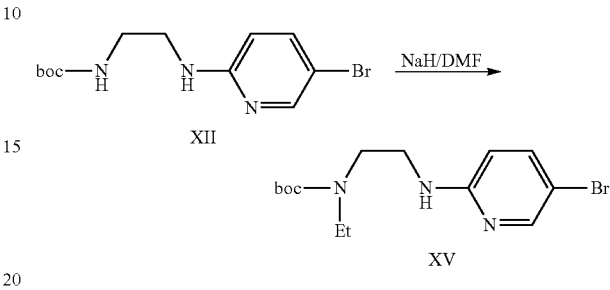

1 g (3.16 mmol) of Compound XII was dissolved in 10 mL of N,N-dimethylformamide, 0.21 g (74 mmol) of 55% sodiumhydride was added to the resulting solution at 0° C., the resulting solution was stirred for 5 minutes, and 0.3 mL (3.79 mmol) of iodoethane was slowly added dropwise to the stirred solution. Subsequently, the temperature of the resultant solution was slowly raised to room temperature and the resultant solution was stirred for 3 hours. The temperature of the reaction mixture was reduced again to 0° C., 10 mL of distilled water was slowly added thereto, the resulting solution was stirred for 5 minutes, and 30 mL of ethylacetate and 20 mL of saturated ammonium chloride were added thereto to extract an organic layer. The organic layer was washed with 30 mL of an aqueous sodium thiosulfate solution and dehydrated using anhydrous sodium sulfate. The dehydrated organic layer was concentrated under reduced pressure and then subjected to column chromatography to obtain 0.48 g (1.39 mmol) of Compound XV as a light yellow liquid (yield: 44%).

$^1$H NMR (600 MHz, CDCl$_3$) δ 8.09 (s, 1H), 7.43 (m, 1H), 6.31 (d, J=8.4 Hz, 1H), 5.26 (brs, 1H), 3.43 (m, 4H), 3.22 (m, 2H), 1.45 (s, 9H), 1.10 (t, J=6.6 Hz, 1H)

Preparation Example 16

Preparation of Compound XVI

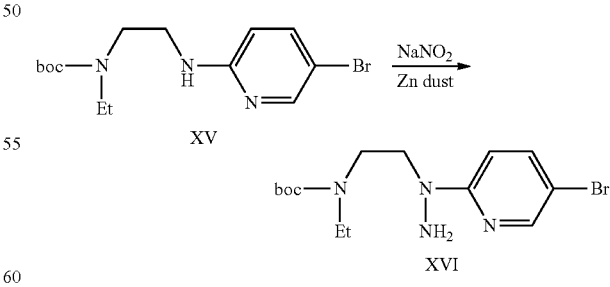

0.48 g (1.39 mmol) of Compound XV was dissolved in 6 mL of acetic acid, the resulting solution was cooled to 0° C., and 0.11 g (1.66 mmol) of sodium nitrite dissolved in 2 mL of distilled water was slowly added dropwise thereto. The reaction temperature was raised from 0° C. to room temperature, the resultant solution was stirred for 30 minutes, the temperature thereof was lowered again to 0° C., and 0.27 g (4.18 mmol) of zinc was added to the resultant solution and then was further stirred for 1 hour. The stirred solution was neutralized at 0° C. using 50 mL of distilled water and saturated sodium bicarbonate, 0.4 mL of 4M hydrochloric acid dissolved in 1,4-dioxane was added thereto, the resulting solution was extracted with 50 mL of ethylacetate, and the extract was dehydrated using anhydrous sodium sulfate and then concentrated under reduced pressure to obtain 0.51 g (1.29 mmol) of Compound XVI as a light yellow solid (yield: 93%).

$^1$H NMR (600 MHz, DMSO d-$_6$) δ 8.24 (s, 1H), 7.96 (s, 1H), 7.09 (d, J=9 Hz, 1H), 3.85 (m, 2H), 3.40 (m, 2H), 3.09 (m, 2H), 1.39~4.30 (m, 9H), 1.01 (t, J=6.6 Hz, 1H)

Preparation Example 17

Preparation of Compound A-IV

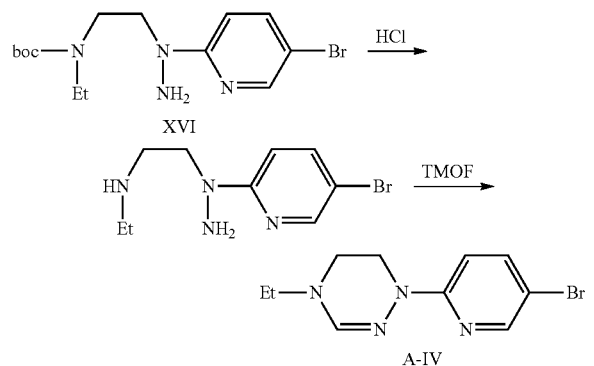

0.51 g (1.29 mmol) of Compound XVI was dissolved in 20 mL of dichloromethane, the resulting solution was cooled to 0° C., and 20 mL of 4M hydrochloric acid dissolved in 1,4-dioxane was added dropwise thereto. Subsequently, the resultant solution was stirred for 1 hour and then concentrated under reduced pressure to obtain a solid product. The solid product was washed with 20 mL of diethylether to obtain 0.42 g (1.26 mmol) of a light yellow solid compound from which the Boc group is removed (yield: 98%).

$^1$H NMR (400 MHz, DMSO d-$_6$) δ 9.20 (brs, 1H), 8.29 (d, J=2 Hz, 1H), 7.98 (dd, J$_1$=9.2 Hz, J$_2$=2.4 Hz, 1H), 7.32 (d, J=9.2 Hz, 1H), 4.04 (t, J=6.4 Hz, 1H), 3.27 (t, J=6.4 Hz, 1H), 2.97 (q, J=7.2 Hz, 1H), 1.21 (t, J=7.2 Hz, 1H)

Subsequently, 0.4 g (1.20 mmol) of the obtained compound and 3 mL of trimethylorthoformate were added to 6 mL of acetic acid and the resulting solution was refluxed by stirring for 3 hours. The reaction mixture was cooled to room temperature and then concentrated under reduced pressure, 10 mL of distilled water was added thereto, and the resultant solution was extracted using 20 mL of dichloromethane to obtain an organic layer. The organic layer was dehydrated with anhydrous sodium sulfate, concentrated under reduced pressure, and then subjected to column chromatography to obtain 171 mg (0.63 mmol) of Compound A-IV as a light brown solid (yield: 53%).

$^1$H NMR (600 MHz, CDCl$_3$) δ 8.11 (d, J=1.8 Hz, 1H), 7.55 (dd, J$_1$=9 Hz, J$_2$=2.4 Hz, 1H), 7.19 (d, J=9 Hz, 1H), 6.72 (s, 1H), 3.98 (t, J=4.8 Hz, 2H), 3.39 (t, J=4.8 Hz, 2H), 3.17 (q, J=7.2 Hz, 2H), 1.18 (t, J=7.2 Hz, 2H)

Preparation Example 18

Preparation of Compound XVII

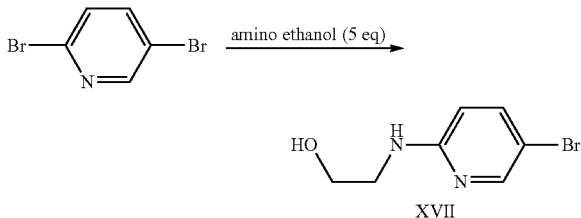

10 g (42.20 mmol) of 2,5-dibromopyridine was added to 13 mL of 2-aminoethanol, and the resulting solution was refluxed by stirring for 3 hours. The reaction mixture was cooled to room temperature and dissolved in ethylacetate, the resultant solution was washed with an aqueous saturated sodium bicarbonate solution and then dehydrated with anhydrous sodium sulfate, followed by concentration under reduced pressure, to obtain 9.05 g (41.46 mmol) of Compound XVII as a white solid (yield: 98%).

$^1$H NMR (400 MHz, CDCl$_3$) δ 8.08 (d, J=1.6 Hz, 1H), 7.46 (dd, J$_1$=8.8 Hz, J$_2$=1.6 Hz, 1H), 6.37 (d, J=8.8 Hz), 4.87 (s, 1H), 3.81 (t, J=4.4 Hz, 2H), 3.65 (s, 1H), 3.45 (m, 2H)

Preparation Example 19

Preparation of Compound XVIII

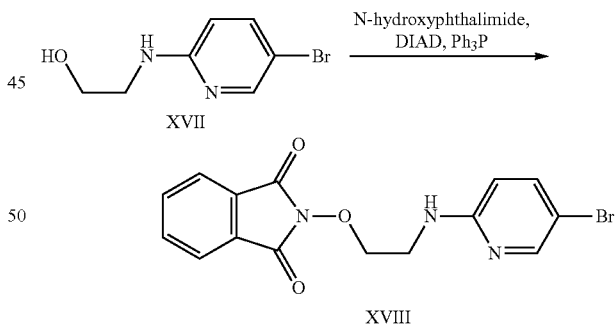

9 g (41.46 mmol) of Compound XVII, 7.44 g (45.61 mmol) of N-hydroxyphthalimide, and 14.14 g (53.90 mmol) of triphenylphosphine were added to 150 mL of tetrahydrofuran, and the resulting solution was stirred under an argon gas atmosphere. Subsequently, 10.61 mL (53.90 mmol) of diisopropyl azodicarboxylate was slowly added dropwise to the stirred solution at −5° C. Thereafter, solid produced after 1 hour was filtered, and the filtrate was concentrated under reduced pressure and then subjected to column chromatography to obtain 8.1 g of Compound XVIII as a white solid (yield: 54%).

¹H NMR (600 MHz, CDCl₃) δ 8.10 (d, J=2.4 Hz, 1H), 7.85 (m, 2H), 7.78 (m, 2H), 7.46 (dd, J₁=9.0 Hz, J₂=2.4 Hz, 1H), 6.47 (dd, J₁=8.4 Hz, J₂=0.6 Hz, 1H), 5.62 (m, 1H), 4.37 (t, J=4.8 Hz, 2H), 3.70 (m, 2H)

¹H NMR (600 MHz, CDCl₃) δ 8.39 (s, 1H), 8.35 (dd, J₁=2.4 Hz, J₂=0.6 Hz, 1H), 7.78 (dd, J₁=13.8 Hz, J₂=2.4 Hz, 1H), 6.73 (dd, J₁=9.0 Hz, J₂=0.6 Hz, 1H), 4.21 (t, J=4.8 Hz, 2H), 3.83 (t, J=4.8 Hz, 2H)

Preparation Example 20

Preparation of Compound XIX

Preparation Example 22

Preparation of Compound XX

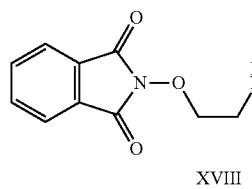

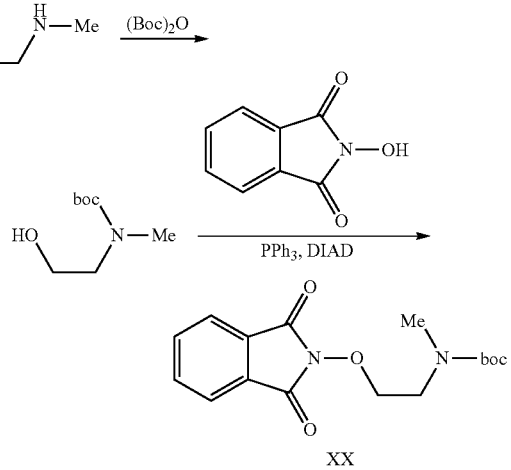

8.1 g (22.36 mmol) of Compound XVIII was added to 100 mL of ethanol, 2.24 mL (44.73 mmol) of hydrazine monohydrate was added dropwise thereto, and the resulting solution was heated to 70° C. and then was stirred for 2 hours. The produced solid was washed with dichloromethane and diethylether and the filtrate was concentrated under reduced pressure to obtain 4.51 g (19.4 mmol) of Compound XIX as a brown solid (yield: 87%).

¹H NMR (400 MHz, CDCl₃) δ 8.10 (dd, J₁=2.8 Hz, J₂=0.8 Hz, 1H), 7.46 (dd, J₁=8.8 Hz, J₂=2.4 Hz, 1H), 6.33 (dd, J₁=8.8 Hz, J₂=0.4 Hz, 1H), 3.86 (t, J=4.8 Hz, 2H), 3.52 (m, 2H)

Preparation Example 21

Preparation of Compound A-V

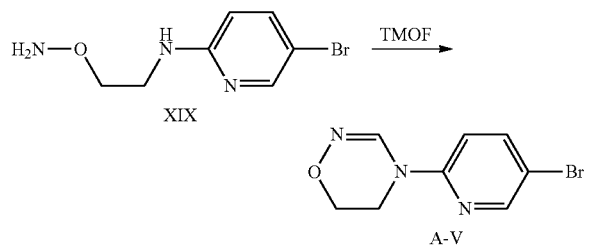

2.5 g (10.77 mmol) of Compound XIX was added to 40 mL of acetic acid and 20 mL of trimethylorthoformate, and the resulting solution was refluxed by stirring for 1.5 hours. The resultant compound was cooled to room temperature and concentrated under reduced pressure, 100 mL of ethylacetate was added thereto, the resulting solution was washed twice with 80 mL of an aqueous saturated sodium bicarbonate solution and then dehydrated using anhydrous sodium sulfate, followed by concentration under reduced pressure and column chromatography, to obtain 2.03 g (8.42 mmol) of Compound A-V as a white solid (yield: 78%).

90.1 g (1.2 mol) of 2-(methylamino)ethanol was dissolved in 1.2 L of methylene chloride, 218 g (1 mol) of Boc₂O was slowly added thereto while the resulting solution was stirred at 0° C., and the resulting solution was stirred at room temperature for 3 hours. The reaction mixture was sequentially washed with 700 mL of an aqueous saturated ammonium chloride solution and 300 mL of water, dehydrated using anhydrous sodium sulfate, and then concentrated under reduced pressure to obtain 175 g (1 mol) of an achromic oil compound protected by the Boc group (yield: 100%).

¹H NMR (600 MHz, CDCl₃) δ 7.84 (br s, 2H), 7.76 (br s, 2H), 4.34 (d, J=15.0 Hz, 2H), 3.63 (br s, 2H), 3.04 (d, J=15.0 Hz, 3H), 1.46 (d, J=16.2 Hz, 9H)

90 g (0.514 mol) of the obtained compound was dissolved in 1.5 L of tetrahydrofuran, 88.0 g (539 mol) of N-hydroxyphthalimide and 141 g (0.539 mol) of triphenylphosphine were added thereto, 106 mL (0.539 mol) of diisopropyl azodicarboxylate was slowly added thereto while stirring the resulting solution at 0° C., and the resulting solution was stirred for 3 hours while the temperature thereof was raised to room temperature. After concentration of the reaction mixture under reduced pressure, 600 mL of isopropylether was added thereto, the resulting solution was stirred at 0° C. for 1 hour, and white solid-type triphenylphosphine oxide was filtered. The solid was washed with 200 mL of isopropylether cooled to 0° C. and collected with the first filtrate, and the resulting filtrate was concentrated under reduced pressure to obtain 198 g of a mixture of Compound XX and diisopropyl hydrazodicarboxylate in a mixing ratio of 10 to 15% (yield: 120%).

$^1$H NMR (600 MHz, CDCl$_3$) δ 7.84 (br s, 2H), 7.76 (br s, 2H), 4.34 (d, J=15.0 Hz, 2H), 3.63 (br s, 2H), 3.04 (d, J=15.0 Hz, 3H), 1.46 (d, J=16.2 Hz, 9H)

Preparation Example 23

Preparation of Compound XXI

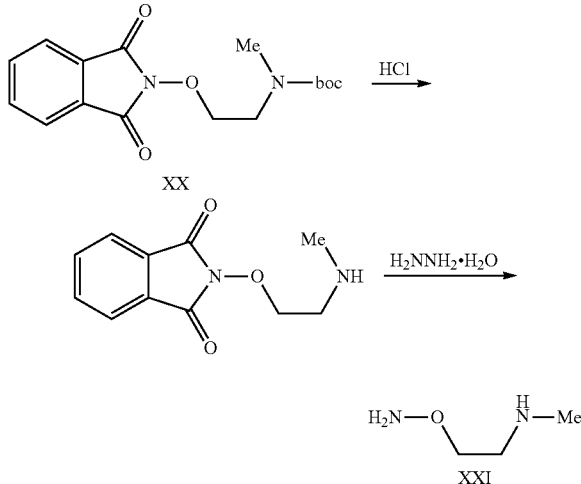

198 g (514 mmol) of Compound XX was dissolved in 260 mL of 1,4-dioxane, 385 mL (1.54 mol) of 4M-hydrochloric acid dissolved in 1,4-dioxane was slowly added thereto while stirring the resulting solution at 0° C., and the resulting solution was stirred at room temperature for 4 hours and further stirred at 0° C. for 1 hour. White solid produced after reaction therebetween was filtered and then washed with 200 mL of 1,4-dioxane cooled to 0° C. to obtain 116 g (514 mmol) of a white solid compound from which the boc group is removed.

$^1$H NMR (600 MHz, DMSO-d$_6$) δ 9.31 (br s, 1H), 7.88-7.92 (m, 4H), 4.46 (t, J=5.4 Hz, 2H), 3.30 (t, J=5.4 Hz, 2H), 2.66 (s, 3H)

53 g (210 mmol) of the obtained compound was dissolved in 1.5 L of ethanol, 25.1 mL (0.518 mol) of hydrazine monohydrate was added thereto while stirring the resulting solution at room temperature using a mechanical stirrer, and the resulting solution was refluxed by stirring for 4 hours. The reaction mixture was cooled to 0° C. and stirred for 1 hour. The produced solid (i.e., phthalhydrazide) was filtered and washed with 100 mL of ethanol cooled to 0° C., and the filtrate was concentrated under reduced pressure. The concentrate was further concentrated under reduced pressure after adding 250 mL of dichloromethane and 500 mL of toluene thereto, 250 mL of toluene was added thereto, and concentration under reduced pressure was repeated twice to remove an excess of hydrazine to obtain 25.1 g (202 mmol) of Compound XXI as a white solid (yield: 96%).

$^1$H NMR (600 MHz, DMSO-d$_6$) δ 3.74 (t, J=4.8 Hz, 2H), 3.08 (t, J=4.8 Hz, 2H), 2.54 (s, 3H),

Preparation Example 24

Preparation of Compound XXVIII

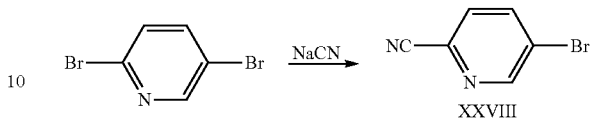

30 g (126.63 mmol) of 2,5-dibromopyridine, 9.87 g (108.90 mmol) of copper cyanide, and 5.3 g (108.90 mmol) of sodium cyanide were added to 300 mL of N,N-dimethylformamide, and the resulting solution was heated to 150° C. and stirred for 5 hours. The compound was cooled to room temperature, 400 mL of ethylacetate was added thereto, and the resultant compound was washed three times with 300 mL of water. The obtained organic layer was washed with 200 mL of saturated sodium chloride and dehydrated using anhydrous sodium sulfate, followed by concentration under reduced pressure and column chromatography, to obtain 12.17 g of Compound XXVIII as a white solid (yield: 53%).

$^1$H NMR (600 MHz, CDCl$_3$) δ 8.80 (dd, J$_1$=2.4 Hz, J$_2$=0.6 Hz, 1H), 8.00 (dd, J$_1$=8.4 Hz, J$_2$=1.8 Hz, 1H), 7.60 (dd, J$_1$=8.4 Hz, J$_2$=1.2 Hz, 1H)

Preparation Example 25

Preparation of Compound A-VI

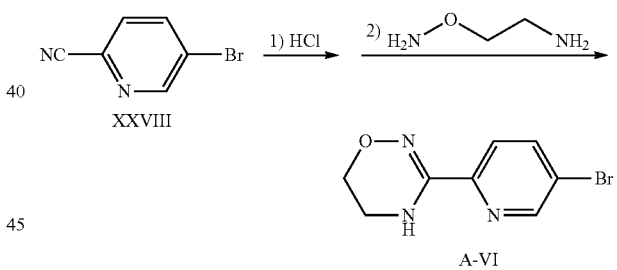

2 g (10.93 mmol) of Compound XXVIII was added to 1.91 mL of ethanol, 13.7 mL of 4M-hydrochloric acid dissolved in dioxane was added thereto, the resulting solution was stirred under an argon gas atmosphere at room temperature for 18 hours and then concentrated under reduced pressure, and the concentrate was dissolved in 30 mL of methanol. Subsequently, 2.46 g (21.86 mmol) of a diamine compound synthesized from ethanolamine using the same method as that used in Preparation Examples 22 and 23 was added to 100 mL of methanol, 3.02 g (21.86 mmol) of potassium carbonate was added thereto while stirring the resulting solution, the resulting solution was stirred at room temperature for 30 minutes and then filtered, the filtrate was concentrated under reduced pressure, the pre-formed methanol solution was added thereto, and the resulting filtrate was stirred at room temperature for 12 hours. The compound was concentrated under reduced pressure, 30 mL of acetic acid was added thereto, and the resulting compound was refluxed by stirring for 4 hours. The resulting compound was cooled to room temperature and then concentrated under reduced pressure, 100 mL of dichloromethane was added thereto, and the resulting solution was washed with 100 mL of saturated sodium bicarbonate and dehydrated using anhydrous sodium sulfate, followed by concentration under reduced pressure and column chromatography, to obtain 1.14 g (4.71 mmol) of Compound A-VI (yield: 43%).

$^1$H NMR (600 MHz, CDCl$_3$) δ 8.57 (d, J=2.4 Hz), 7.94 (dd, J$_1$=8.4 Hz, J$_2$=0.6 Hz, 1H), 7.85 (dd, J$_1$=8.4 Hz, J$_2$=2.4 Hz, 1H), 6.43 (m, 1H), 4.06 (t, J=4.8 Hz, 2H), 3.83 (m, 2H)

Preparation Example 26

Preparation of Compound A-VII

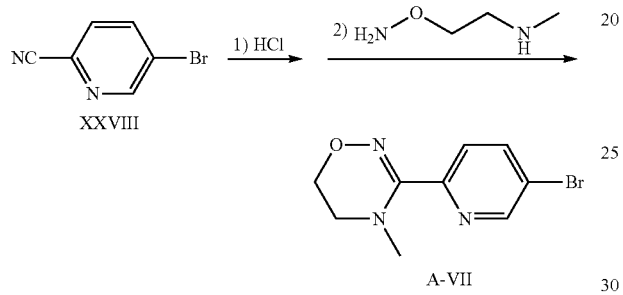

1.15 g (4.49 mmol) of Compound A-VII was obtained as a white solid (yield: 41%) from 2 g (10.93 mmol) of Compound XXVIII by reaction with diamine compound XXI prepared according to Preparation Example 23 in the same manner as in Example 25.

$^1$H NMR (600 MHz, CDCl$_3$) δ 8.70 (d, J=2.4 Hz), 7.89 (dd, J$_1$=8.4 Hz, J$_2$=2.4 Hz, 1H), 7.56 (d, J=8.4 Hz, 1H), 4.14 (t, J=4.8 Hz, 2H), 3.48 (t, J=4.8 Hz, 2H), 2.88 (s, 3H)

Preparation Example 27

Preparation of Compound XXIX

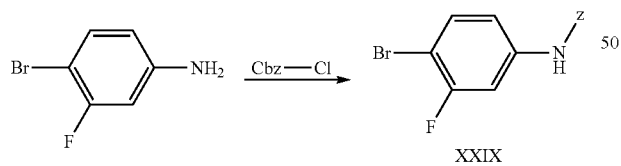

100 g (528 mmol) of 3-fluoro-4-bromoaniline was dissolved in 500 mL of dichloromethane, 800 mL of an aqueous 1N NaOH solution was added thereto, and 82 mL (580 mmol) of Cbz-Cl (benzyl chloroformate) was slowly added dropwise thereto while stirring the resulting solution. The resulting solution was stirred at room temperature for 1 hour to separate an organic layer therefrom. The organic layer was washed twice with water, dehydrated using anhydrous sodium sulfate, and then concentrated under reduced pressure to obtain 173 g (528 mmol) of Compound XXIX as a white solid.

$^1$H NMR (600 MHz, CDCl$_3$) δ 7.40 (m, 7H), 6.93 (dd, J$_1$=9.0 Hz, J$_Z$=2.4 Hz, 1H), 6.71 (s, 1H), 5.20 (s, 2H)

Preparation Example 28

Preparation of Compound B-I

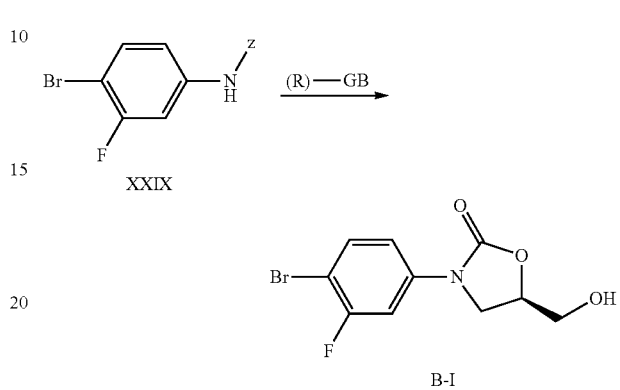

119 g (367 mmol) of Compound XXIX was dissolved in 300 mL of tetrahydrofuran/150 mL of dimethylformamide, 38.19 g (477 mmol) of lithium-t butoxide was slowly added dropwise thereto at 0° C., the resulting solution was stirred for 10 minutes, 63 mL (440 mmol) of (R)-glycidyl butyrate and 21 mL (550 mmol) of methanol were added thereto, and the resultant solution was stirred at room temperature for 3 hours. Subsequently, pH of the reaction mixture was adjusted to approximately 6 using an aqueous ammonium chloride solution and then the reaction mixture was concentrated under reduced pressure. The concentrate was dissolved in 1000 mL of 80% ethylacetate/hexane, was sequentially washed with water and an aqueous saturated sodium chloride solution (brine), and then dehydrated using anhydrous sodium sulfate, followed by concentration under reduced pressure and column chromatography, to obtain 93 g (320 mmol) of Compound B-I as a white solid (yield: 87%).

$^1$H NMR (600 MHz, CDCl$_3$) δ 7.53 (m, 2H), 7.15 (dd, J$_1$=9.0 Hz, J$_2$=2.4 Hz, 1H), 4.77 (m, 1H), 4.00 (m, 3H), 3.77 (m, 1H), 2.10 (t, J=6.0 Hz, 1H)

Preparation Example 29

Preparation of Compound B-II

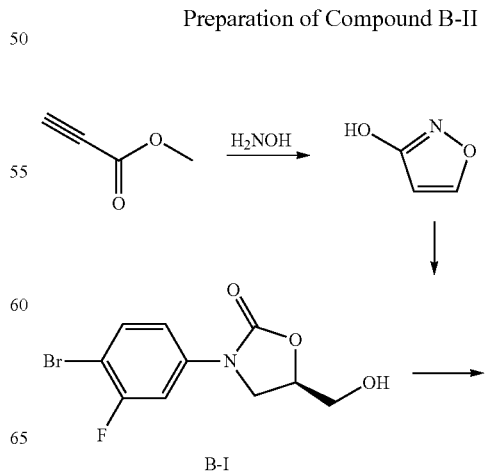

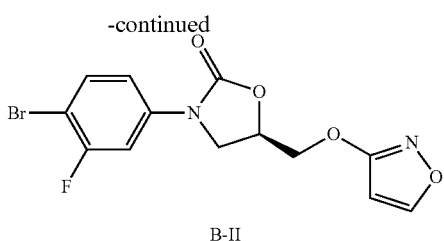

B-II 58 g (1.45 mol) of sodium hydroxide was added to 580 mL of water, 35 g (0.5 mol) of hydroxylamine hydrochloride was added thereto while stirring the resulting solution, and a solution prepared by diluting 38 mL (0.43 mol) of methyl propiolate in 600 mL of methanol was added thereto. The resulting solution was stirred at room temperature for 6 days, pH thereof was adjusted to 2 using strong hydrochloric acid, and the solution was saturated with sodium chloride and then extracted eight times with 500 mL of dichloromethane. The extract was dehydrated using anhydrous sodium sulfate and then concentrated under reduced pressure to obtain a solid. The obtained solid was washed three times with 200 mL of hot hexane to obtain 11.53 g (140 mmol) of a hydroxyisoxazole compound as ivory solid (yield: 32%).

$^1$H NMR (400 MHz, CDCl$_3$) δ 11.25 (bs, 1H), 8.52 (d, J=2.0 Hz, 1H), 6.07 (d, J=2.0 Hz, 1H)

5 g (17.24 mmol) of the obtained hydroxyisoxazole compound, 1.8 g (20.68 mmol) of Compound B-I, and 5.9 g (22.41 mmol) of triphenylphosphine were added to 90 mL of tetrahydrofuran, and 4.4 mL (22.41 mmol) of diisopropyl azodicarboxylate was slowly added dropwise thereto at 0° C. The resulting solution was stirred at room temperature for 1.5 hours, followed by concentration under reduced pressure and column chromatography, to obtain 4.58 g (12.8 mmol) of Compound B-II as a white solid (yield: 74%).

$^1$H NMR (400 MHz, CDCl$_3$) δ 8.16 (d, J=2.0 Hz, 1H), 7.55 (m, 2H), 7.18 (m, 1H), 6.01 (d, J=2.0 Hz, 1H), 5.03 (m, 1H), 4.59 (dd, J$_1$=11.6 Hz, J$_2$=4.0 Hz, 1H), 4.51 (dd, J$_1$=11.6 Hz, J$_2$=4.4 Hz, 1H), 4.16 (t, J=8.8 Hz, 1H), 3.97 (dd, J$_1$=8.8 Hz, J$_2$=6.0 Hz, 1H)

Preparation Example 30

Preparation of Compound XXX

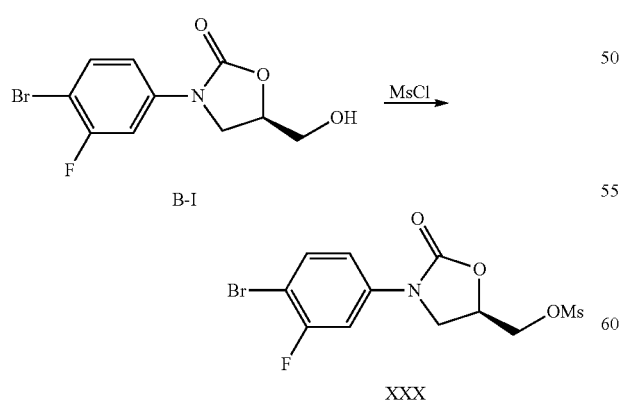

30 g (103 mmol) of Compound B-I and 23 mL (134 mmol) of diisopropylethylamine were dissolved in 350 mL of dichloromethane, 9.6 mL (124 mmol) of methanesulfonyl chloride (MsCl) was slowly added dropwise thereto at 0° C., and the resulting solution was stirred for 20 minutes and further stirred at room temperature for 1 hour. The reaction mixture was dissolved in 300 mL of dichloromethane and then sequentially washed with 200 mL of an aqueous 0.5 N hydrochloric acid solution, 100 mL of an aqueous saturated sodium bicarbonate solution, and 100 mL of an aqueous saturated sodium chloride solution, followed by dehydration with anhydrous sodium sulfate and concentration under reduced pressure, to obtain 38 g (103 mol) of Compound XXX as a brown solid (yield: 99%).

$^1$H NMR (400 MHz, CDCl$_3$) δ 7.53 (m, 2H), 7.14 (dd, J$_1$=8.8 Hz, J$_2$=2.4 Hz, 1H), 4.95 (m, 1H), 4.46 (m, 2H), 4.13 (dd, J$_1$=9.2 Hz, J$_2$=9.2 Hz, 1H), 3.94 (dd, J$_1$=9.2 Hz, J$_2$=6.4 Hz, 1H), 3.10 (s, 3H)

Preparation Example 31

Preparation of Compound B-III

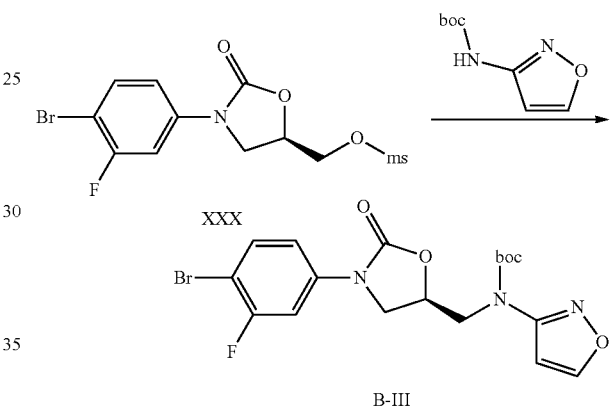

B-III 2.5 g (6.87 mmol) of Compound XXX and 1.26 g (6.87 mmol) of Boc-aminoisoxazole were dissolved in 7 mL of dimethylformamide, 0.33 g (7.56 mmol) of NaH was added thereto at 0° C., and the resulting solution was stirred at 75° C. for 2.5 hours. The reaction mixture was extracted using ethylacetate and distilled water to obtain an organic layer. The organic layer was dehydrated using anhydrous sodium sulfate, followed by concentration under reduced pressure and column chromatography, to obtain 2.61 g (5.72 mmol) of Compound B-III as a white solid (yield: 83%).

$^1$H NMR (600 MHz, CDCl$_3$) δ 8.26 (d, J=1.8 Hz, 1H), 7.53 (m, 2H), 7.14 (dd, J=9.0 Hz, J=3.0 Hz, 1H), 6.01 (br, 1H), 5.92 (m, 1H), 4.37 (dd, J=7.8 Hz, 1H), 4.12 (m, 2H), 3.81 (dd, J=8.4 Hz, J=4 Hz, 1H), 1.56 (s, 9H)

Preparation Example 32

Preparation of Compound XXXI

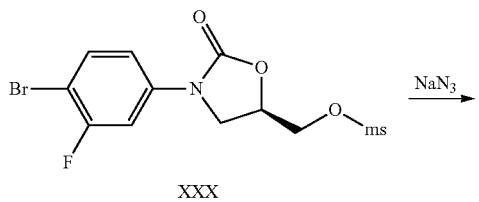

-continued

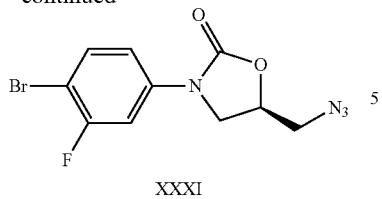

XXXI 38 g (103 mmol) of Compound XXX and 16.8 g (258 mmol) of sodium azide were added to 90 mL of dimethylformamide, and the resulting solution was stirred at 90° C. for 3 hours. The reaction mixture was dissolved in 500 mL of ethylacetate and then washed with distilled water, followed by dehydration with anhydrous sodium sulfate and concentration under reduced pressure, to obtain 33 g (103 mol) of Compound XXXI as a light brown solid (yield: 99%).

$^1$H NMR (600 MHz, CDCl$_3$) δ 7.53 (m, 2H), 7.15 (dd, $J_1$=9.0 Hz, $J_2$=2.4 Hz, 1H), 4.80 (m, 1H), 4.06 (dd, $J_1$=9.0 Hz, $J_2$=9.0 Hz, 1H), 3.84 (dd, $J_1$=9.0 Hz, $J_2$=6.0 Hz, 1H), 3.73 (dd, $J_1$=13.2 Hz, $J_2$=4.8 Hz, 1H), 3.61 (dd, $J_1$=13.2 Hz, $J_2$=4.8 Hz, 1H)

Preparation Example 33

Preparation of Compound B-IV

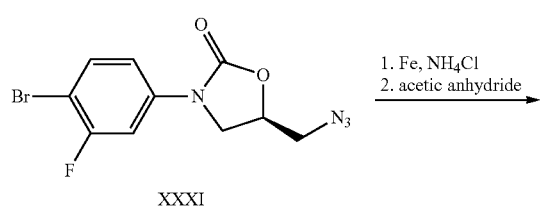

XXXI

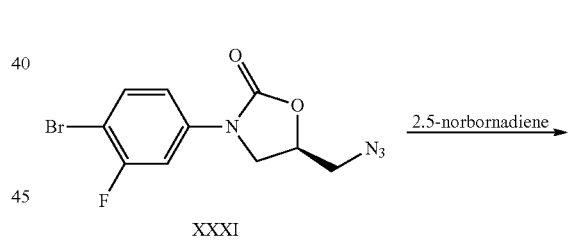

B-IV 4.2 g (13.3 mmol) of Compound XXXI, 2.2 g (40.0 mmol) of iron powder, 7.1 g (133.3 mmol) of ammonium chloride, and 10 mL of distilled water were added to 40 mL of ethanol, and the resulting solution was refluxed by stirring for 12 hours. The reaction mixture was cooled to room temperature, filtered through celite, concentrated under reduced pressure, extracted with dichloromethane and an aqueous sodium bicarbonate solution, dehydrated using anhydrous sodium sulfate, and then filtered, 1.4 mL (14.0 mmol) of acetic anhydride was added thereto, and the resulting solution was stirred at room temperature for 1 hour. The reaction mixture was extracted with dichloromethane and an aqueous sodium bicarbonate solution, dehydrated using anhydrous sodium sulfate, and then filtered, followed by concentration under reduced pressure and column chromatography, to obtain 3.5 g (10.6 mol) of Compound B-IV as a light brown solid (yield: 79%).

$^1$H NMR (600 MHz, DMSO) δ 8.26 (t, J=6.0 Hz, 1H), 7.72 (t, J=8.4 Hz, 1H), 7.65 (dd, $J_1$=12.0 Hz, $J_2$=2.4 Hz 1H), 7.32 (dd, $J_1$=8.4 Hz, $J_2$=3.6 Hz, 1H), 4.74 (m, 1H), 4.12 (dd, $J_1$=9.0 Hz, $J_2$=9.0 Hz, 1H), 3.73 (dd, $J_1$=9.0 Hz, $J_2$=6.6 Hz, 1H), 3.42 (t, J=5.4 Hz, 2H), 1.83 (s, 3H)

Preparation Example 34

Preparation of Compound B-V

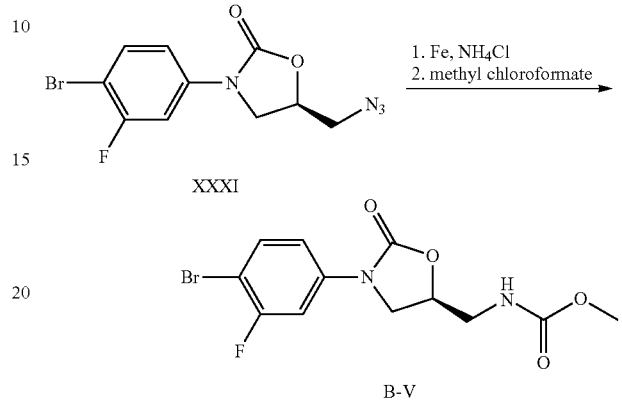

19.7 g (56.7 mmol) of Compound B-V Was obtained as a white solid using methyl chloroformate in the same manner as in Preparation Example 33.

$^1$H NMR (600 MHz, CDCl$_3$) δ 7.53 (m, 2H), 7.11 (dd, $J_1$=9.0 Hz, $J_2$=2.4 Hz, 1H), 5.11 (s, 1H), 4.78 (m, 1H), 4.04 (dd, $J_1$=9.0 Hz, $J_2$=9.0 Hz, 1H), 3.80 (m, 1H), 3.68 (s, 3H), 3.61 (m, 2H)

Preparation Example 35

Preparation of Compound B-VI 2.92 g (9.27 mmol) of Compound XXXI and 9.4 mL (92.7 mmol) of 2.5-norbornadiene(bycyclo[2,2,1]hepta-2,5-diene) were added to 50 mL of 1,4-dioxane, and the resulting solution was refluxed by stirring for 2.5 hours. The reaction mixture was concentrated under reduced pressure and then extracted using 150 mL of dichloromethane and 100 mL of distilled water. The extracted organic layer was dehydrated using anhydrous sodium sulfate, followed by concentration under reduced pressure and column chromatography, to obtain 2 g (5.8 mmol) of Compound B-VI (yield: 63%).

$^1$H NMR (600 MHz, CDCl$_3$) δ 7.78 (d, J=1.2 Hz, 1H), 7.75 (d, J=1.2 Hz, 1H), 7.49 (dd, $J_1$=8.4 Hz, $J_2$=7.8 Hz, 1H), 7.42

(dd, $J_1$=10.8 Hz, $J_2$=2.4 Hz, 1H), 7.00 (dd, $J_1$=9.0 Hz, $J_2$=2.4 Hz, 1H), 5.08 (m, 1H), 4.80 (dd, $J_1$=4.2 Hz, $J_2$=1.2 Hz, 2H), 4.15 (dd, $J_1$=9.6 Hz, $J_2$=9.6 Hz, 1H), 3.94 (dd, $J_1$=9.6 Hz, $J_2$=6.6 Hz, 1H)

Preparation Example 36

Preparation of Compound B-VII

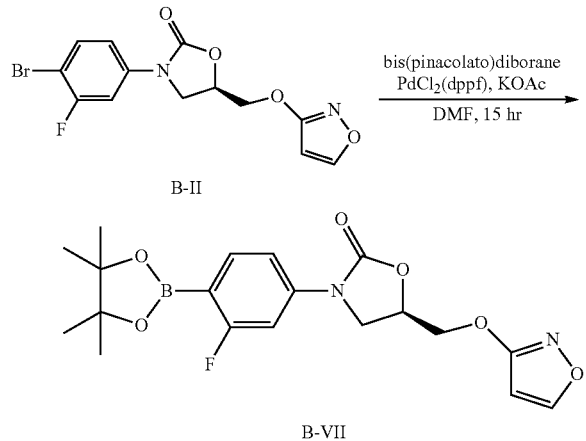

To 20 mL of N,N-dimethylformamide were sequentially added 2 g (5.60 mmol) of Compound B-II, 2.1 g (8.40 mmol) of bispinacolatodiborane, 274 mg (0.34 mmol) of $PdCl_2$(dppf), and 1.65 g (16.80 mmol) of potassium acetate, and the resulting solution was stirred under a nitrogen atmosphere at 90° C. for 15 hours. The reaction mixture was cooled to room temperature and then was extracted with 80 mL of distilled water and 100 mL of ethylacetate. The extracted organic layer was dehydrated using anhydrous sodium sulfate, followed by concentration under reduced pressure and column chromatography, to obtain 1.11 g (2.75 mmol) of Compound B-VII (yield: 49%).

$^1$H NMR (600 MHz, $CDCl_3$) δ 8.16 (d, J=1.8 Hz, 1H), 7.44 (dd, $J_1$=8.4 Hz, $J_2$=1.2 Hz, 1H), 7.41 (dd, $J_1$=11.4 Hz, $J_2$=1.8 Hz, 1H), 7.28 (dd, $J_1$=7.8 Hz, $J_2$=1.8 Hz, 1H), 6.00 (d, J=1.8 Hz, 1H), 5.04 (m, 1H), 4.59 (m, 1H), 4.05 (m, 1H), 4.18 (t, J=9.0 Hz, 1H), 3.99 (dd, $J_1$=9.0 Hz, $J_2$=6.6 Hz, 1H), 1.36 (s, 12H)

Preparation Example 37

Preparation of Compound B-VIII

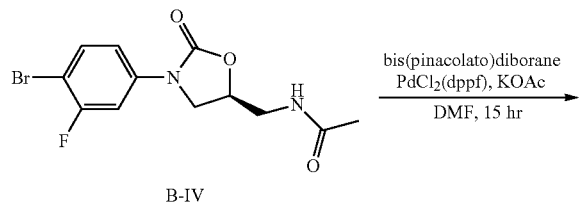

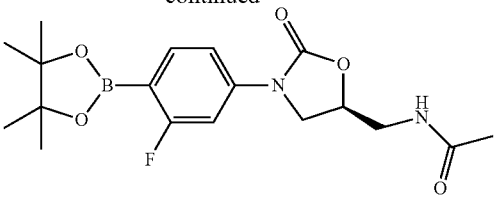

To 5 mL of N,N-dimethylformamide were sequentially added 0.3 g (0.90 mmol) of Compound B-IV, 0.3 g (1.18 mmol) of bispinacolatodiborane, 22 mg (0.03 mmol) of $PdCl_2$(dppf), and 0.27 g (2.71 mmol) of potassium acetate, and the resulting solution was stirred under a nitrogen atmosphere at 90° C. for 15 hours. The reaction mixture was cooled to room temperature and then was extracted with 40 mL of distilled water and 50 mL of ethylacetate. The extracted organic layer was dehydrated using anhydrous sodium sulfate, followed by concentration under reduced pressure, to obtain 350 mg of Compound B-VIII in a mixture form. The obtained compound was used in a subsequent process without purification.

Preparation Example 38

Preparation of Compound B-IX

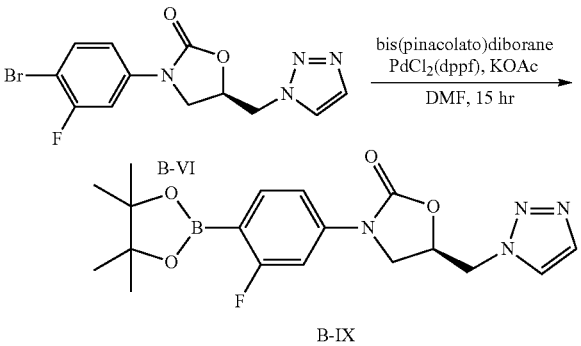

0.75 g (1.95 mmol) of Compound B-IX was obtained (yield: 55%) from 1.2 g (3.52 mmol) of Compound B-VI in the same manner as in Preparation Example 36.

$^1$H NMR (600 MHz, $CDCl_3$) δ 7.78 (d, J=1.2 Hz, 1H), 7.45 (d, J=1.2 Hz, 1H), 7.70 (dd, $J_1$=8.4 Hz, $J_2$=7.2 Hz, 1H), 7.31 (dd, $J_1$=11.4 Hz, $J_2$=1.8 Hz, 1H), 7.12 (dd, $J_1$=8.4 Hz, $J_2$=1.8 Hz, 1H), 5.07 (m, 1H), 4.79 (m, 2H), 4.18 (dd, $J_1$=9.0 Hz, $J_2$=9.0 Hz, 1H), 3.93 (dd, $J_1$=9.0 Hz, $J_2$=5.4 Hz, 1H), 1.32 (s, 12H)

Preparation Example 39

Preparation of Compound B-X

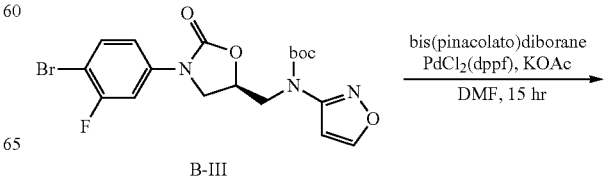

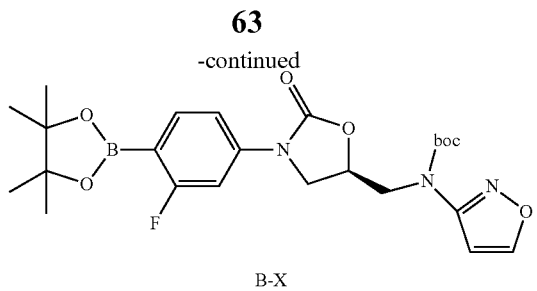

B-X 0.8 g (1.59 mmol) of Compound B-X was obtained (yield: 98%) from 0.74 g (1.62 mmol) of Compound B-III in the same manner as in Preparation Example 36.

$^1$H NMR (600 MHz, CDCl$_3$) δ 8.26 (d, J=0.6 Hz, 1H), 7.23 (dd, J$_1$=7.8 Hz, J$_2$=7.8 Hz, 1H), 7.39 (dd, J$_1$=11.4 Hz, J$_2$=1.2 Hz, 1H), 7.25 (dd, J$_1$=8.4 Hz, J$_2$=1.2 Hz, 1H), 6.92 (br, 1H), 5.09 (m, 1H), 4.38 (dd, J$_1$=8.4 Hz, J$_2$=8.4 Hz, 1H), 4.12 (dd, J$_1$=8.4 Hz, 2H), 3.82 (dd, J$_1$=8.4 Hz, J$_2$=5.4 Hz, 1H), 1.36 (s, 9H), 1.26 (s, 12H)

Preparation Example 40

Preparation of Compound B-XI

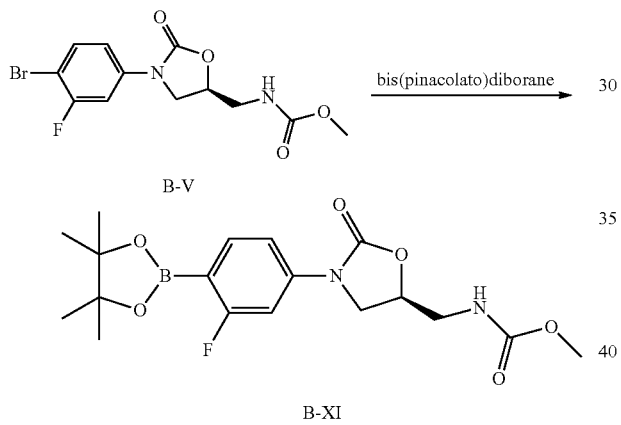

0.88 g (2.24 mmol) of Compound B-XI was obtained (yield: 78%) from 1 g (2.88 mmol) of Compound B-V in the same manner as in Preparation Example 36.

$^1$H NMR (600 MHz, CDCl$_3$) δ 7.24 (dd, J$_1$=8.4 Hz, J$_2$=8.4 Hz, 1H), 7.39 (dd, J$_1$=11.4 Hz, J$_2$=1.2 Hz, 1H), 7.23 (dd, J$_1$=8.4 Hz, J$_2$=1.8 Hz, 1H), 5.14 (m, 1H), 4.78 (m, 1H), 4.07 (dd, J$_1$=9.0 Hz, J$_2$=9.0 Hz, 1H), 3.81 (m, 1H), 3.68 (s, 3H), 3.62 (m, 1H), 3.54 (m, 1H) 1.36 (s, 12H)

Preparation Example 41

Preparation of Compound B-XII

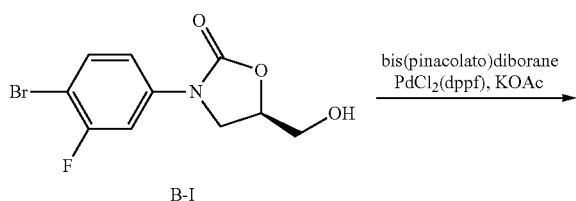

B-XII 1.03 g (3.06 mmol) of Compound B-XII was obtained (yield: 88%) from 1 g (3.45 mmol) of Compound B-I in the same manner as in Preparation Example 36.

$^1$H NMR (600 MHz, CDCl$_3$) δ 7.45 (dd, J$_1$=8.4 Hz, J$_2$=8.4 Hz, 1H), 7.43 (dd, J$_1$=10.8 Hz, J$_2$=1.8 Hz, 1H), 7.29 (dd, J$_1$=7.8 Hz, J$_2$=1.8 Hz, 1H), 4.77 (m, 1H), 4.01 (m, 3H), 3.78 (m, 1H), 2.10 (t, J=5.4 Hz, 1H), 1.37 (s, 12H)

EXAMPLES

Example 1

Preparation of Compound 1

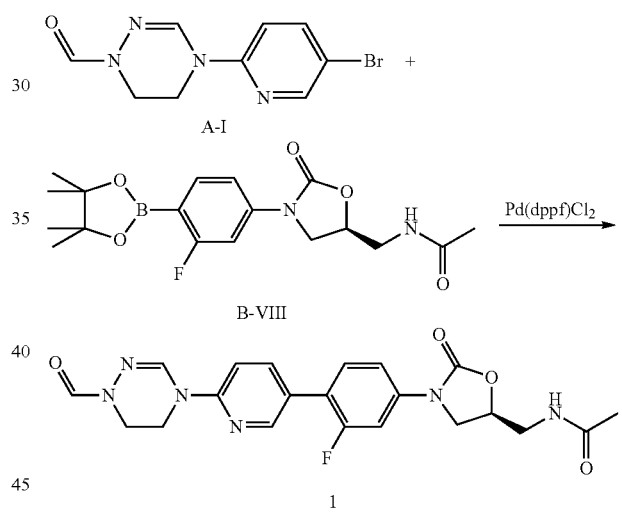

0.8 g (2.99 mmol) of Compound A-I synthesized in preparation example above, 1.3 g (3.30 mmol) of Compound B-VIII, PdCl$_2$(dppf), and a 2M aqueous sodium carbonate solution were added to 20 mL of dimethylformamide, and the resulting solution was stirred at 90° C. for 2 hours. The reaction mixture was cooled to room temperature and then extracted with 150 mL of dichloromethane and 300 mL of distilled water, followed by dehydration using anhydrous sodium sulfate and concentration under reduced pressure.

The concentrate was purified by column chromatography to obtain 1.04 g (2.28 mmol) of Compound 1 as a gray solid (yield: 76%).

$^1$H NMR (600 MHz, DMSO d-$_6$) δ 8.52 (s, 1H), 8.50 (s, 1H), 8.28 (t, J=6.0 Hz, 1H), 8.06 (s, 1H), 8.10 (d, J=9.0 Hz), 1H), 7.63 (m, 2H), 7.43 (dd, J$_1$=8.4 Hz, J$_2$=2.4 Hz), 7.36 (d, J=8.4 Hz, 1H), 4.76 (m, 1H), 4.17 (t, J=9.0 Hz, 1H), 4.18 (t, J=7.8 Hz, 2H), 3.92 (m, 4H), 3.78 (dd, J$_1$=9.0 Hz, J$_2$=6.6 Hz, 1H), 3.44 (t, J=6.0 Hz, 2H), 1.84 (s, 3H)

LCMS: 441 (M+H$^+$) for C$_{21}$H$_{21}$FN$_6$O$_4$

Example 2

Preparation of Compound 2

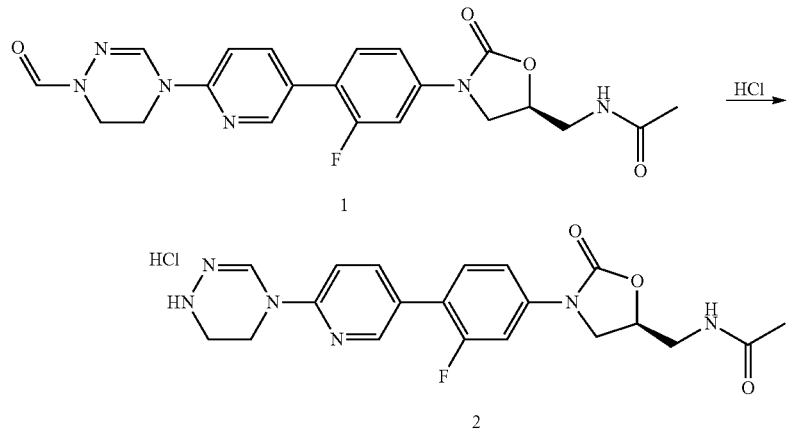

0.6 g (1.36 mmol) of Compound 1 synthesized according to Example 1 was dissolved in 4.5 mL of methanol and 4.5 mL of dichloromethane, 1 mL of 4M HCl was added thereto at 0° C., and the resulting solution was stirred for 30 minutes. The reaction mixture was concentrated under reduced pressure to obtain 0.8 g (1.36 mmol) of Compound 2 as a yellow foam.

$^1$H NMR (600 MHz, DMSO d-$_6$) δ 9.00 (s, 1H), 8.62 (s, 1H), 8.30 (t, J=6.0 Hz, 1H), 8.14 (d, J=9.0 Hz, 1H), 7.68 (dd, J$_1$=9.0 Hz, J$_2$=9.0 Hz, 1H), 7.65 (dd, J=7.8 Hz, J$_2$=2.4 Hz, 1H), 7.57 (d, J=8.4 Hz, 1H), 7.46 (dd, J$_1$=9.0 Hz, J$_2$=2.4 Hz, 1H), 4.78 (m, 1H), 4.19 (t, J=9.0 Hz, 1H), 4.03 (t, J=4.8 Hz, 2H), 3.79 (dd, J$_1$=9.0 Hz, J$_2$=6.6 Hz, 1H), 3.44 (m, 4H), 1.84 (s, 3H)

LCMS: 413 (M+H$^+$) for C$_{20}$H$_{21}$FN$_6$O$_3$

Example 3

Preparation of Compound 3

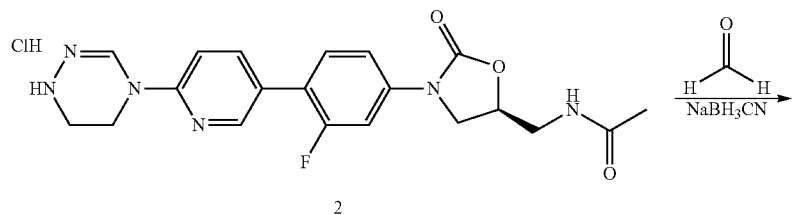

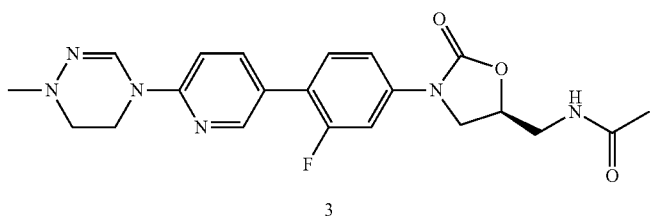

0.23 g (0.50 mmol) of Compound 2 synthesized according to Example 2, 0.06 mL (0.75 mmol) of formaldehyde, 0.09 mL (0.50 mmol) of diisopropylethylamine, 47 mg (0.75 mmol) of sodium cyanoborohydride, and 0.03 mL (0.5 mmol) of acetic acid were sequentially added to 2 mL of methanol at 0° C., and the resulting solution was stirred at room temperature for 3 hours. The reaction mixture was filtered and washed with 3 mL of methanol to obtain 78 mg (0.17 mmol) of Compound 3 (yield: 34%).

$^1$H NMR (600 MHz, DMSO d-$_6$) δ 8.44 (s, 1H), 8.25 (t, J=6.0 Hz, 1H), 7.95 (s, 1H), 7.92 (d, J=9.6 Hz, 1H), 7.61 (m, 2H), 7.41 (dd, J$_1$=9.0 Hz, J$_2$=2.4 Hz, 1H), 7.16 (d, J=8.4 Hz, 1H), 4.76 (m, 1H), 4.17 (dd, J$_1$=9.0 Hz, J$_2$=9.0 Hz, 1H), 3.84 (t, J=5.4 Hz, 2H), 3.79 (dd, J$_1$=9.0 Hz, J$_2$=6.0 Hz, 1H), 3.43 (t, J=5.4 Hz, 2H), 2.95 (t, J=5.4 Hz, 2H), 2.68 (s, 3H), 1.84 (s, 3H)

LCMS: 427 (M+H$^+$) for C$_{21}$H$_{23}$FN$_6$O$_3$

Example 4

Preparation of Compound 4

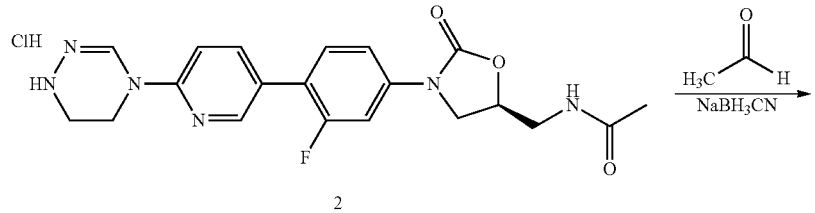

230 mg (0.52 mmol) of Compound 4 was obtained (yield: 63%) using acetaldehyde in the same manner as in Example 3.

$^1$H NMR (400 MHz, CDCl$_3$) δ 8.45 (s, 1H), 8.00 (s, 1H), 7.81 (d, J=8.8 Hz, 1H), 7.56 (dd, J$_1$=13.2 Hz, J$_2$=2.4 Hz, 1H), 7.43 (dd, J$_1$=8.8 Hz, J$_2$=8.8 Hz, 1H), 7.32 (dd, J$_1$=9.2 Hz, J$_2$=2.4 Hz, 1H), 6.87 (d, J=8.8 Hz, 1H), 6.09 (t, J=5.6 Hz, 1H), 4.84 (m, 1H), 4.11 (dd, J$_1$=8.8 Hz, J$_2$=8.8 Hz, 1H), 3.97 (t, J=5.2 Hz, 2H), 3.84 (dd, J$_1$=9.2 Hz, J$_2$=5.6 Hz, 1H), 3.69 (m, 2H), 3.08 (t, J=5.6 Hz, 2H), 3.04 (m, 2H), 2.06 (s, 3H), 1.28 (t, J=7.2 Hz, 3H)

LCMS: 441 (M+H$^+$) for C$_{22}$H$_{25}$FN$_6$O$_3$

Example 5

Preparation of Compound 5

0.20 g (0.38 mmol) of Compound 2 synthesized according to Example 2 and 0.13 mL (0.76 mmol) of diisopropylethylamine were sequentially added to 5 mL of dimethylformamide, 0.05 mL (0.46 mmol) of ethylbromoacetate was slowly added thereto, and the resulting solution was stirred at 80° C. The reaction mixture was cooled to room temperature and then washed twice with 50 mL of ethylacetate and 60 mL of distilled water, followed by dehydration using anhydrous sodium sulfate and concentration under reduced pressure. The concentrate was separated by column chromatography to obtain 110 mg (0.22 mmol) of Compound 5 as a brown solid.

$^1$H NMR (600 MHz, CDCl$_3$) δ 8.45 (s, 1H), 7.98 (s, 1H), 7.81 (d, J=9.0 Hz, 1H), 7.56 (dd, J$_1$=12.6 Hz, J$_2$=2.4 Hz, 1H), 7.42 (t, J=8.4 Hz, 1H), 7.29 (m, 1H), 6.87 (d, J=9.0 Hz, 1H), 6.08 (t, J=6.6 Hz, 1H), 4.83 (m, 1H), 4.25 (q, J=7.2 Hz, 2H), 4.10 (m, 1H), 3.99 (t, J=5.4 Hz, 2H), 3.84 (s, 2H), 3.75 (m, 1H), 3.72 (m, 1H), 3.66 (m, 1H), 3.03 (t, J=5.4 Hz, 2H), 2.05 (s, 3H), 1.32 (t, J=7.2 Hz, 3H)

LCMS: 499 (M+H$^+$) for C$_{24}$H$_{27}$FN$_6$O$_5$

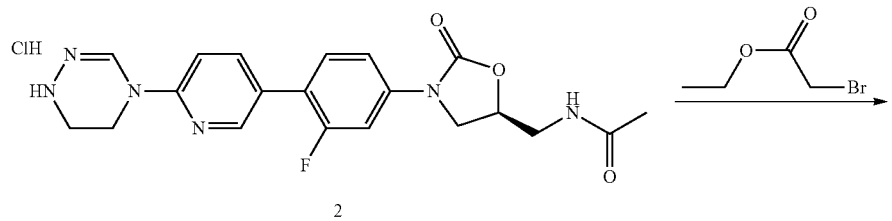

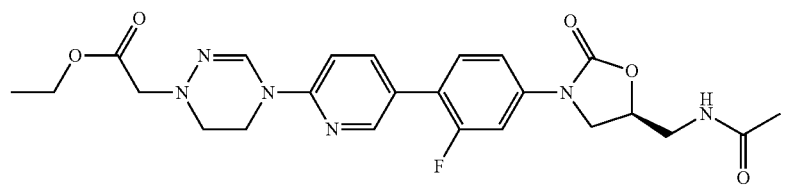

Example 6

Preparation of Compound 6

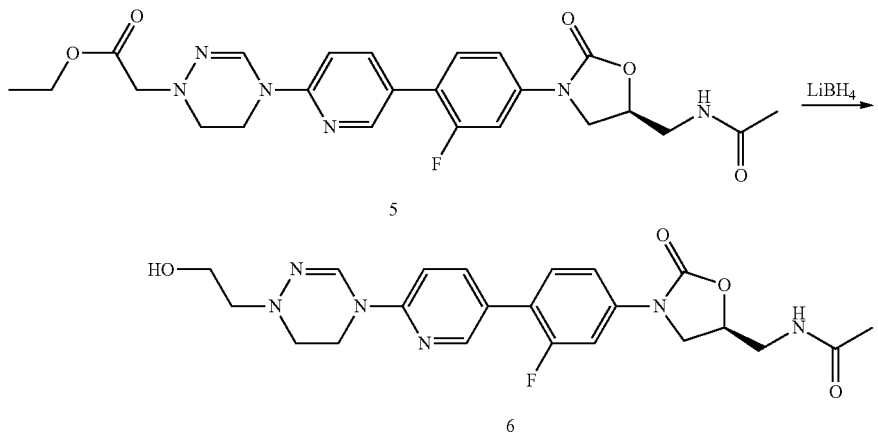

0.11 g (0.22 mmol) of Compound 5 synthesized according to Example 5 was dissolved in 10 mL of tetrahydrofuran, and 0.2 mL of 2M lithium borohydride dissolved in tetrahydrofuran was slowly added dropwise thereto. The resulting solution was stirred at room temperature for 1 hour, and 0.2 mL of 2M lithium borohydride dissolved in tetrahydrofuran was added dropwise again thereto. Thereafter, 0.5 mL of an aqueous saturated ammonium chloride solution was added to the resulting solution and the resulting solution was diluted with 30 mL of dichloromethane, followed by dehydration with anhydrous sodium sulfate and concentration under reduced pressure. The concentrate was separated by column chromatography to obtain 24 mg (0.05 mmol) of Compound 6 as a yellow solid (yield: 24%).

$^1$H NMR (600 MHz, CDCl$_3$) δ 8.44 (s, 1H), 8.02 (s, 1H), 7.82 (d, J=8.4 Hz, 1H), 7.56 (dd, J$_1$=12.6 Hz, J$_2$=1.8 Hz, 1H), 7.41 (t, J=8.4 Hz, 1H), 7.29 (m, 1H), 6.87 (d, J=9.0 Hz, 1H), 6.17 (t, J=6.6 Hz), 4.83 (m, 1H), 3.99 (m, 2H), 3.97 (t, J=5.4 Hz, 1H), 3.84 (m, 1H), 3.73 (m, 1H), 3.69 (m, 1H), 3.50 (m, 2H), 3.12 (m, 2H), 3.06 (m, 2H), 2.05 (s, 3H)

LCMS: 457 (M+H$^+$) for C$_{22}$H$_{25}$FN$_6$O$_4$

Example 7

Preparation of Compound 7

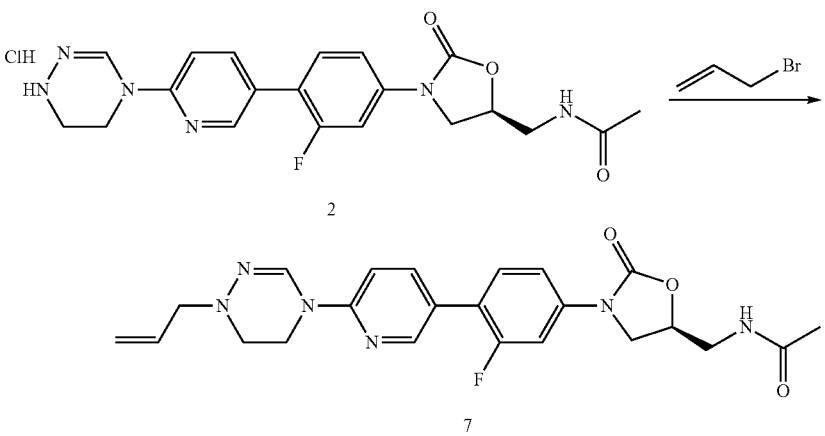

0.10 g (0.19 mmol) of Compound 2 of Example 2 and 0.06 mL (0.38 mmol) of diisopropylethylamine were sequentially added to 3 mL of dimethylformamide, 0.02 mL (0.23 mmol) of allylbromide was slowly added thereto, and the resulting solution was stirred at room temperature for 20 hours. The reaction mixture was washed twice with 50 mL of dichloromethane and 50 mL of distilled water, followed by dehydration with anhydrous sodium sulfate and concentration under reduced pressure. The concentrate was separated by column chromatography to obtain 25 mg (0.06 mmol) of Compound 7 as a brown solid (yield: 29%).

$^1$H NMR (600 MHz, CDCl$_3$) δ 8.43 (s, 1H), 7.99 (s, 1H), 7.79 (d, J=8.4 Hz, 1H), 7.54 (dd, J$_1$=13.2 Hz, J$_2$=2.4 Hz, 1H), 7.38 (t, J=9.0 Hz, 1H), 7.31 (m, 1H), 6.85 (d, J=9.0 Hz, 1H), 6.30 (t, J=6.0 Hz, 1H), 6.02 (m, 1H), 5.31 (d, J=16.8 Hz, 1H), 5.25 (d, J=9.6 Hz, 1H), 4.83 (m, 1H), 4.10 (m, 1H), 3.94 (t, J=4.8 Hz, 2H), 3.84 (m, 1H), 3.73 (m, 1H), 3.72 (m, 1H), 3.65 (m, 2H), 3.12 (q, J=7.2 Hz, 2H), 3.04 (t, J=5.4 Hz, 2H), 2.04 (s, 3H)

LCMS: 453 (M+H⁺) for $C_{23}H_{25}FN_6O_3$

Example 8

Preparation of Compound 8

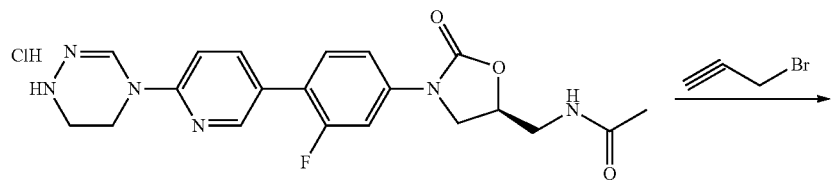

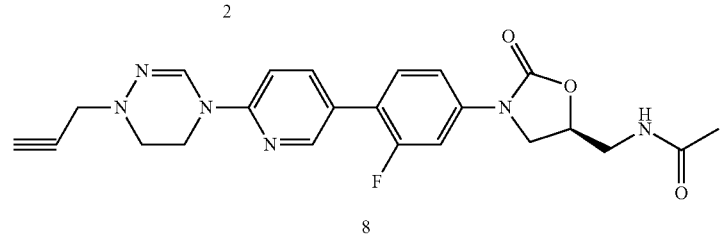

0.10 g (0.19 mmol) of Compound 2 of Example 2 and 0.06 mL (0.38 mmol) of diisopropylethylamine were sequentially added to 3 mL of dimethylformamide, 0.06 mL (0.38 mmol) of propargyl bromide (80% in toluene) was slowly added thereto, and the resulting solution was stirred at room temperature for 20 hours. The reaction mixture was washed twice with 50 mL of dichloromethane and 50 mL of distilled water, dehydrated using anhydrous sodium sulfate, and then concentrated under reduced pressure. The concentrate was separated by column chromatography to obtain 40 mg (0.09 mmol) of Compound 8 as a brown solid (yield: 47%).

¹H NMR (600 MHz, CDCl₃) δ 8.45 (s, 1H), 8.04 (s, 1H), 7.89 (d, J=9.6 Hz, 1H), 7.55 (d, J=12.6 Hz, 1H), 7.42 (t, J=8.9 Hz, 1H), 7.29 (d, J=8.4 Hz, 1H), 6.88 (d, J=9.0 Hz, 1H), 5.97 (m, 1H), 4.82 (m, 1H), 4.09 (t, J=8.7 Hz, 1H), 3.98 (m, 2H), 3.88 (s, 2H), 3.81 (t, J=7.8 Hz, 1H), 3.67 (m, 1H), 3.48 (m, 2H), 3.18 (m, 2H), 2.04 (s, 3H)

LCMS: 451 (M+H⁺) for $C_{23}H_{23}FN_6O_3$

Example 9

Preparation of Compound 9

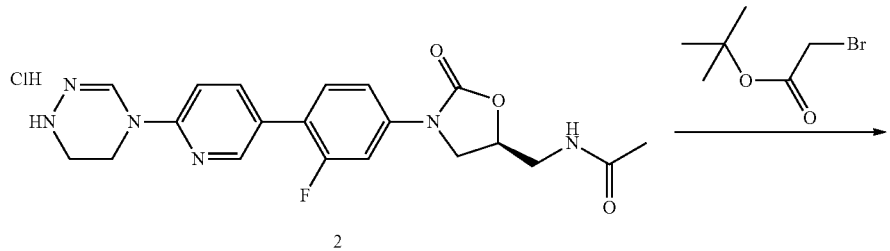

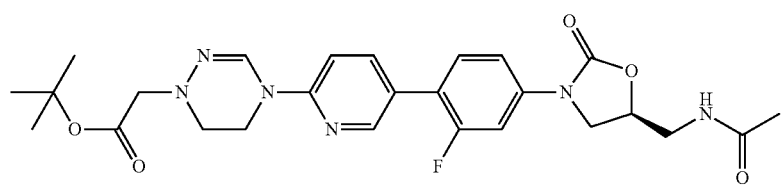

0.10 g (0.19 mmol) of Compound 2 of Example 2 and 0.06 mL (0.38 mmol) of diisopropylethylamine were sequentially added to 2 mL of dimethylformamide, 0.06 mL (0.38 mmol) of tert-butyl bromoacetate was slowly added thereto, and the resulting solution was stirred at room temperature for 20 hours. The reaction mixture was washed three times with 50 mL of ethylacetate and 50 mL of distilled water, dehydrated using anhydrous sodium sulfate, and then concentrated under reduced pressure. The concentrate was separated by column chromatography to obtain 47 mg (0.07 mmol) of Compound 9 as a brown solid (yield: 37%).

$^1$H NMR (600 MHz, CDCl$_3$) δ 8.43 (s, 1H), 7.95 (s, 1H), 7.80 (d, J=8.4 Hz, 1H), 7.55 (dd, J$_1$=12.6 Hz, J$_2$=1.8 Hz, 1H), 7.41 (t, J=8.7 Hz, 1H), 7.28 (dd, J$_1$=9.0 Hz, J$_2$=2.4 Hz, 1H), 6.86 (d, J=9.0 Hz, 1H), 6.08 (t, J=6.3 Hz, 1H), 4.82 (m, 1H), 4.09 (t, J=9.0 Hz, 1H), 3.98 (t, J=4.8 Hz, 2H), 3.82 (dd, J$_1$=9.6 Hz, J$_2$=7.2 Hz, 1H), 3.76 (s, 2H), 3.72 (m, 2H), 3.65 (m, 2H), 3.30 (t, J=4.8 Hz, 2H), 2.04 (s, 9H), 1.50 (s, 9H)

LCMS: 527 (M+H$^+$) for C$_{26}$H$_{31}$FN$_6$O$_5$

Example 10

Preparation of Compound 10

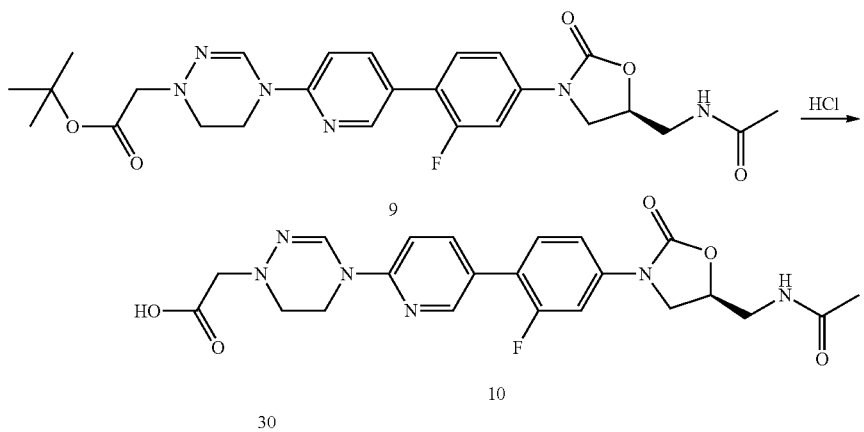

47 mg (0.09 mmol) of Compound 9 synthesized according to Example 9 was added to 2 mL of dichloromethane, 5 mL of 4M hydrochloric acid dissolved in dioxane was added thereto, and the resulting solution was stirred at room temperature for 2 hours, followed by concentration under reduced pressure, to obtain 26 mg (0.06 mmol) of Compound 10 as a yellow solid (yield: 62%).

$^1$H NMR (600 MHz, DMSO d-$_6$) δ 8.52 (s, 1H), 8.37 (bs, 1H), 8.30 (t, J=5.4 Hz, 1H), 8.02 (d, J=7.8 Hz, 1H), 7.65 (m, 2H), 7.44 (d, J=8.4 Hz, 1H), 7.34 (d, J=8.4 Hz, 1H), 4.78 (m, 1H), 4.18 (t, J=8.4 Hz, 1H), 3.96 (m, 2H), 3.81 (s, 2H), 3.79 (m, 2H), 3.44 (m, 2H), 3.34 (m, 1H), 1.84 (s, 3H)

LCMS: 471 (M+H$^+$) for C$_{22}$H$_{23}$FN$_6$O$_5$

Example 11

Preparation of Compound 11

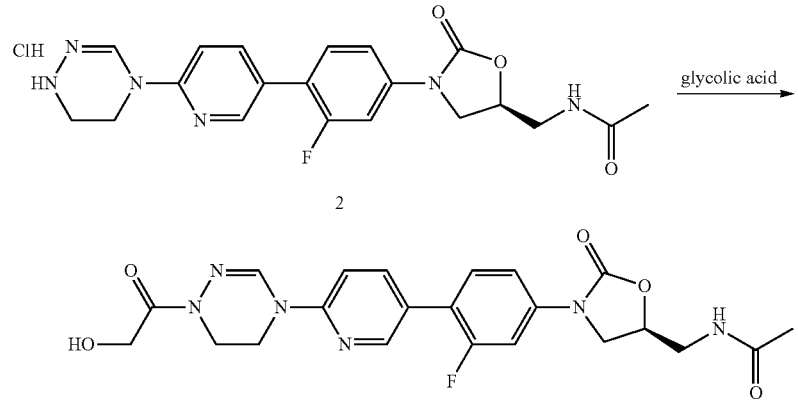

0.5 g (1.11 mmol) of Compound 2 of Example 2, 0.1 g (1.13 mmol) of glycolic acid, 0.39 mL (2.22 mmol) of diisopropylethylamine, and 0.7 g (1.33 mmol) of PyBoP were 3 mL of dimethylformamide at 0° C., and the resulting solution was stirred at room temperature for 2 hours. The reaction mixture was diluted in 30 mL of dichloromethane, washed with 30 mL of distilled water, and then dehydrated using anhydrous sodium sulfate, followed by concentration under reduced pressure. The concentrate was separated by column chromatography to obtain 70 mg (0.15 mmol) of Compound 11 as a white solid (yield: 14%).

$^1$H NMR (600 MHz, DMSO d-$_6$) δ 8.51 (s, 1H), 8.27 (t, J=6.0 Hz, 1H), 8.02 (s, 1H), 8.00 (d, J=9.0 Hz, 1H), 7.64 (dd, J$_1$=9.0 Hz, J$_2$=9.0 Hz, 1H), 7.62 (dd, J=12.0 Hz, J$_2$=1.8 Hz, 1H), 7.43 (dd, J$_1$=9.0 Hz, J$_2$=1.8 Hz, 1H), 7.35 (d, J=8.4 Hz, 1H), 4.78 (m, 1H), 4.63 (t, J=6.0 Hz, 1H), 4.37 (d, J=6.0 Hz, 1H), 4.17 (t, J=9.0 Hz, 1H), 3.93 (s, 4H), 3.78 (dd, J$_1$=9.0 Hz, J$_2$=6.6 Hz, 1H), 3.44 (t, J=6.6 Hz, 1H), 1.84 (s, 3H)

LCMS: 471 (M+H$^+$) for C$_{22}$H$_{23}$FN$_6$O$_5$

Example 12

Preparation of Compound 12

100 mg (0.19 mmol) of Compound 2 of Example 2 and 0.06 mL (0.38 mmol) of diisopropylethylamine were sequentially added to 2 mL of dichloromethane, 0.02 mL (0.19 mmol) of acetoxyacetyl chloride was slowly added thereto, and the resulting solution was stirred at room temperature for 1 hour, followed by concentration under reduced pressure. The concentrate was separated by column chromatography to obtain 38 mg (0.08 mmol) of Compound 12 as a yellow solid (yield: 39%).

$^1$H NMR (600 MHz, CDCl$_3$) δ 8.49 (d, J=0.6 Hz, 1H), 7.91 (s, 1H), 7.88 (dd, J$_1$=8.4 Hz, J$_2$=1.2 Hz, 1H), 7.58 (d, J=12.6 Hz, 1H), 7.42 (t, J=9.0 Hz, 1H), 7.31 (d, J=8.4 Hz, 1H), 6.95 (d, J=9.0 Hz, 1H), 6.10 (t, J=6.3 Hz, 1H), 5.13 (s, 2H), 4.83 (m, 1H), 4.10 (t, J=8.4 Hz, 1H), 4.06 (t, J=4.8 Hz, 2H), 3.93 (t, J=5.1 Hz, 2H), 3.84 (m, 1H), 3.72 (m, 1H), 3.67 (m, 1H), 2.22 (s, 3H), 2.04 (s, 3H)

LCMS: 513 (M+H$^+$) for C$_{24}$H$_{25}$FN$_6$O$_6$

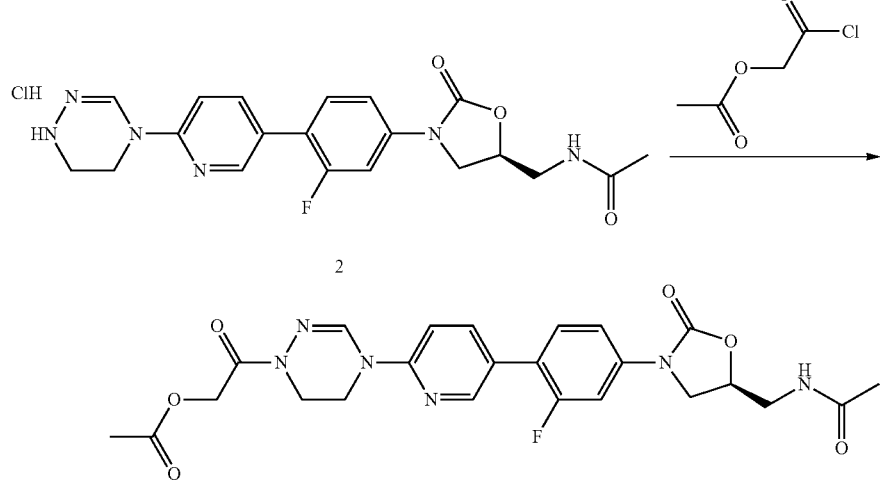

Example 13

Preparation of Compound 13

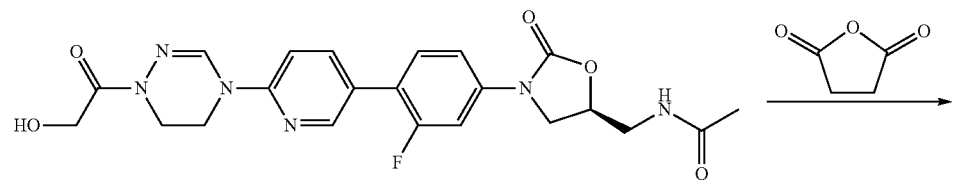

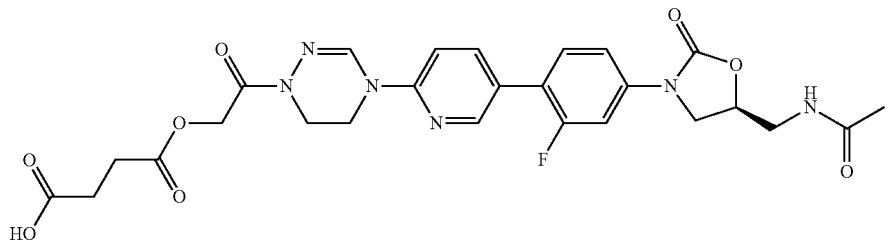

13

30 mg (0.06 mmol) of Compound 11 synthesized according to Example 11, 70 mg (0.07 mmol) of succinic anhydride, and 7.8 mg (0.01 mmol) of dimethylaminopyridine were sequentially added to 2 mL of tetrahydrofuran, and the resulting solution was stirred at room temperature for 5 hours and then concentrated under reduced pressure. The concentrate was separated by column chromatography to obtain 30 mg (0.05 mmol) of Compound 13 as an ivory solid (yield: 83%).

$^1$H NMR (600 MHz, DMSO d-$_6$) δ 8.52 (s, 1H), 8.28 (t, J=6.0 Hz, 1H), 8.08 (d, J=5.4 Hz, 1H), 8.01 (d, J=9.0 Hz, 1H), 7.64 (m, 2H), 7.43 (d, J=8.4 Hz, 1H), 7.40 (d, J=9.0 Hz, 1H), 5.04 (s, 1H), 4.81 (s, 1H), 4.77 (m, 1H), 4.18 (t, J=9.0 Hz, 1H), 3.94 (m, 4H), 3.79 (t, J=8.4 Hz, 1H), 3.44 (t, J=5.4 Hz, 2H), 3.38 (m, 2H), 2.62 (m, 2H), 1.84 (s, 3H)

LCMS: 571 (M+H$^+$) for $C_{26}H_{27}FN_6O_8$

Example 14

Preparation of Compound 14

35 mg (0.07 mmol) of Compound 11 of Example 11, 29 mg (0.11 mmol) of triphenylphosphine, 23 μl (0.11 mmol) of DIAD, and 31 mg (0.11 mmol) of dibenzyl phosphate were added to 1 mL of trihydrofuran at room temperature, and the resulting solution was stirred at room temperature for 2 hours. The reaction mixture was concentrated under reduced pressure and then separated by column chromatography to obtain 40 mg (0.05 mmol) of Compound 14 as a white solid (yield: 71%).

$^1$H NMR (600 MHz, CDCl$_3$) δ 8.49 (s, 1H), 7.88 (d, J=8.4 Hz, 1H), 7.86 (s, 1H), 7.58 (dd, J$_1$=12.6 Hz, J$_2$=2.4 Hz, 1H), 7.43 (dd, J$_1$=8.4 Hz, J$_2$=8.4 Hz, 1H), 7.35 (m, 11H), 6.94 (d, J=7.8 Hz, 1H), 6.00 (t, J=6.0 Hz, 1H), 5.18 (m, 4H), 5.11 (d, J$_1$=11.4 Hz, 1H), 4.82 (m, 1H), 4.11 (dd, J$_1$=9.0 Hz, J$_2$=9.0 Hz, 1H), 4.06 (t, J=5.4 Hz, 2H), 3.90 (s, 2H), 3.82 (dd, J$_1$=9.0 Hz, J$_2$=7.2 Hz, 1H), 3.74 (m, 1H), 3.66 (m, 1H), 2.04 (s, 3H)

LCMS: 741 (M+H$^+$) for $C_{36}H_{36}FN_6O_8P$

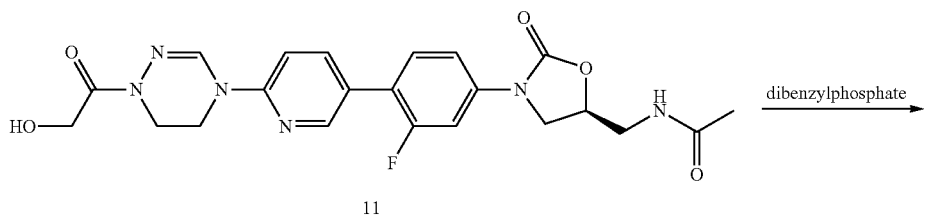

11 → dibenzylphosphate

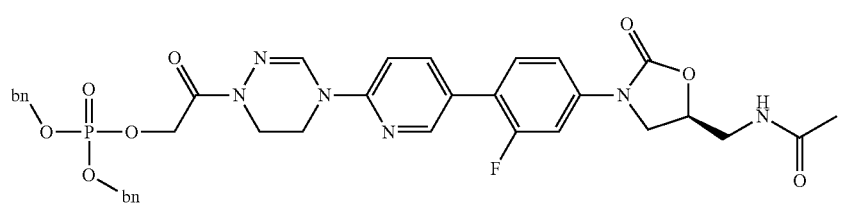

14

Example 15

Preparation of Compound 15

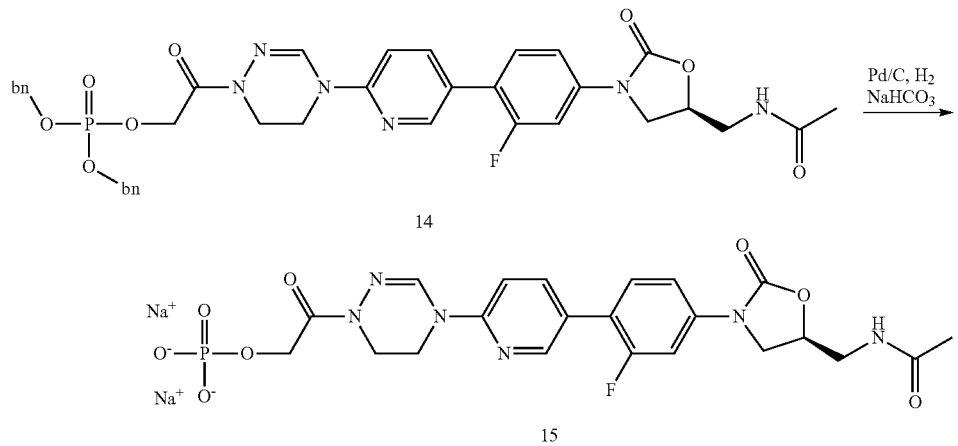

40 mg (0.05 mmol) of Compound 14 synthesized according to Example 14, 20 mg of Pd/C, and 8 mg (0.1 mmol) of sodium bicarbonate were added to tetrahydrofuran (1 mL)/distilled water (2 mL), and the resulting solution was stirred in a hydrogen balloon for 3 hours. The reaction mixture was filtered using celite, was concentrated under reduced pressure, and then was dissolved in 1 mL of distilled water. Thereafter, 3 mL of ethanol was added to the resulting solution, and the resulting solution was solidified and filtered to obtain 15 mg (0.25 mmol) of Compound 15 as a light gray solid (yield: 50%).

$^1$H NMR (600 MHz, $D_2O$) δ 8.18 (s, 1H), 7.78 (d, J=8.4 Hz, 1H), 7.61 (s, 1H), 7.29 (dd, $J_1$=8.4 Hz, $J_2$=8.4 Hz, 1H), 7.23 (d, J=12.4 Hz, 1H), 7.09 (d, J=8.4 Hz, 1H), 6.97 (d, J=9.0 Hz, 1H), 4.58 (m, 3H), 4.00 (dd, $J_1$=9.0 Hz, $J_2$=9.0 Hz, 1H), 3.75 (s, 2H), 3.64 (m, 3H), 3.43 (m, 1H), 3.34 (dd, $J_1$=15.0 Hz, $J_2$=5.4 Hz, 1H), 1.79 (s, 3H)

LCMS: 551 (M+H$^+$) for $C_{22}H_{24}FN_6O_8P$

Example 16

Preparation of Compound 16

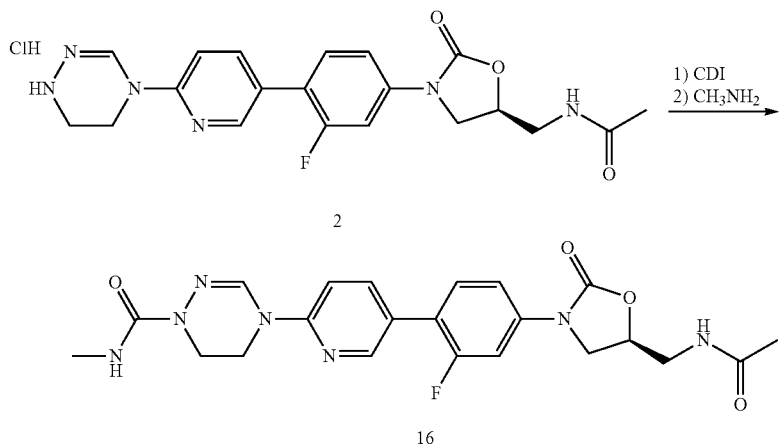

0.25 g (0.55 mmol) of Compound 2 of Example 2, 0.18 g (1.10 mmol) of carbonyldiimidazole, and 0.19 mL (1.09 mmol) of diisopropylethylamine were added to 20 mL of dichloromethane, and the resulting solution was stirred for 1 hour. The reaction mixture was concentrated under reduced pressure to approximately 5 mL, 0.5 mL of 33% methylamine was added thereto, and the resultant mixture was stirred at 50° C. for 1 hour. The reaction mixture was cooled to room temperature and then an obtained precipitate was filtered to obtain 0.17 g (0.36 mmol) of Compound 16 as a white solid (yield: 65%).

$^1$H NMR (600 MHz, DMSO d-$_6$) δ 8.49 (s, 1H), 8.23 (t, J=6.0 Hz, 1H), 7.97 (m, 2H), 7.61 (m, 2H), 7.42 (dd, $J_1$=8.4 Hz, $J_2$=2.4 Hz, 1H), 7.29 (d, J=8.4 Hz, 1H), 6.97 (q, J=4.8 Hz, 1H), 4.76 (m, 1H), 4.17 (dd, J1=9.6 Hz, J2=9.6 Hz, 1H), 3.90

(t, J=5.4 Hz, 2H), 3.79 (m, 3H), 3.44 (t, J=5.4 Hz, 1H), 2.67 (d, J=4.2 Hz, 3H), 1.84 (s, 3H)

LCMS: 470 (M+H$^+$) for $C_{22}H_{24}FN_7O_4$

Example 17

Preparation of Compound 17

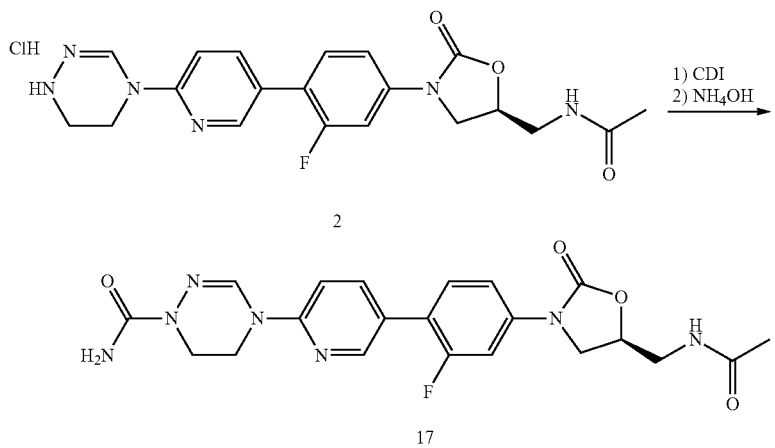

0.14 g (0.31 mmol) of Compound 17 was obtained (yield: 56%) as a white solid in the same manner as in Example 16, except that aqueous ammonia was used instead of methylamine.

$^1$H NMR (600 MHz, DMSO d-$_6$) δ 8.50 (s, 1H), 8.27 (t, J=6.0 Hz, 1H), 7.98 (d, J=6.0 Hz, 1H), 7.96 (s, 1H), 7.62 (m, 2H), 7.43 (dd, J$_1$=8.4 Hz, J$_2$=2.4 Hz, 1H), 7.30 (d, J=9.0 Hz, 1H), 6.44 (s, 2H), 4.77 (m, 1H), 4.17 (dd, J$_1$=9.0 Hz, J$_2$=9.0 Hz, 1H), 3.90 (t, J=5.4 Hz, 2H), 3.80 (m, 3H), 3.44 (t, J=5.4 Hz, 1H), 1.84 (s, 3H)

LCMS: 456 (M+H$^+$) for $C_{21}H_{22}FN_7O_4$

Example 18

Preparation of Compound 18

50 mg (0.09 mmol) of Compound 18 was obtained (yield: 41%) using boc-Glycine in the same manner as in Example 11.

$^1$H NMR (600 MHz, DMSO d-$_6$) δ 8.52 (s, 1H), 8.28 (t, J=6.0 Hz, 1H), 8.05 (s, 1H), 8.00 (dd, J$_1$=7.2 Hz, J$_2$=2.4 Hz, 1H), 7.65 (dd, J$_1$=8.4 Hz, J$_2$=8.4 Hz, 1H), 7.62 (dd, J$_1$=13.8 Hz, J$_2$=2.4 Hz, 1H), 7.43 (dd, J$_1$=8.4 Hz, J$_2$=2.4 Hz, 1H), 7.35 (d, J=8.4 Hz, 1H), 6.48 (t, 6.0 Hz, 1H), 4.77 (m, 1H), 4.17 (dd, J$_1$=9.0 Hz, J$_2$=9.0 Hz, 1H), 4.05 (d, J=6.0 Hz, 2H), 3.93 (s, 4H), 3.79 (dd, J=9.0 Hz, J$_2$=6.0 Hz, 1H), 3.44 (t, J=6.0 Hz, 2H) 1.84 (s, 3H), 1.38 (s, 9H)

LCMS: 570 (M+H$^+$) for $C_{27}H_{32}FN_7O_6$

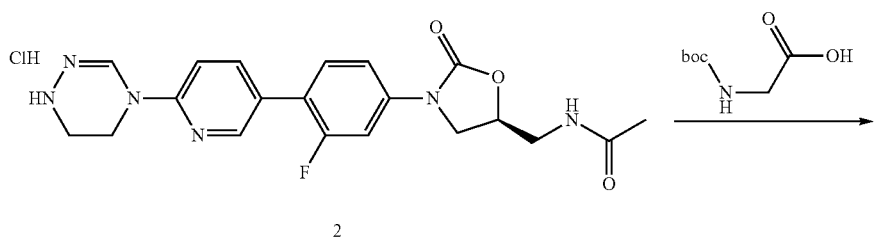

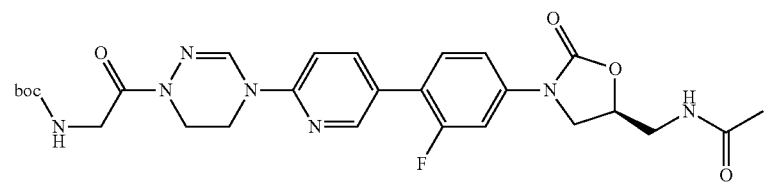

Example 19

Preparation of Compound 19

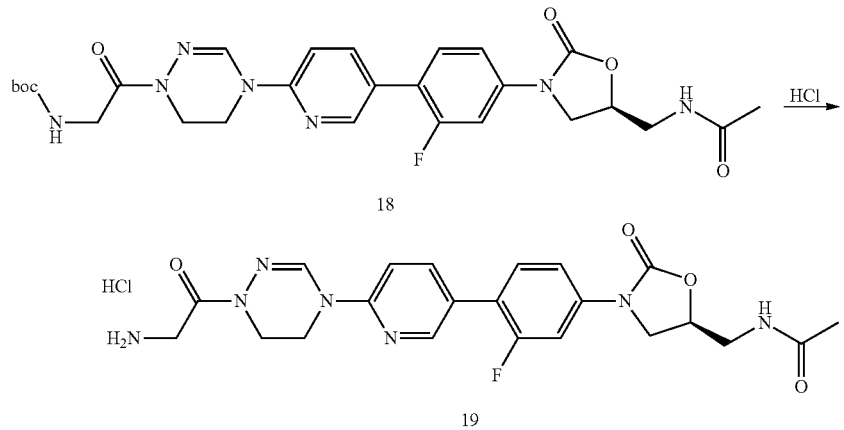

50 mg (0.09 mmol) of Compound 18 synthesized according to Example 18 was dissolved in 10 mL of dichloromethane, 1 mL of 4M HCl was added thereto, and the resulting solution was stirred for 1 hour. The reaction mixture was concentrated under reduced pressure to obtain 46 mg (0.09 mmol) of Compound 19 as a yellow solid (yield: 99%).

$^1$H NMR (600 MHz, DMSO d-$_6$) δ 8.53 (s, 1H), 8.29 (t, J=6.0 Hz, 1H), 8.18 (m, 4H), 8.02 (dd, J$_1$=8.4 Hz, J$_2$=2.4 Hz, 1H), 7.63 (m, 2H), 7.44 (dd, J$_1$=13.2 Hz, J$_2$=2.4 Hz, 1H), 7.40 (d, J=7.2 Hz, 1H), 6.48 (t, 6.0 Hz, 1H), 4.77 (m, 1H), 4.17 (dd, J$_1$=7.8 Hz, J$_2$=7.8 Hz, 1H), 4.00 (m, 4H), 3.80 (m, 1H), 3.45 (m, 4H), 1.84 (s, 3H)

LCMS: 470 (M+H$^+$) for C$_{22}$H$_{24}$FN$_7$O$_4$

Example 20

Preparation of Compound 20

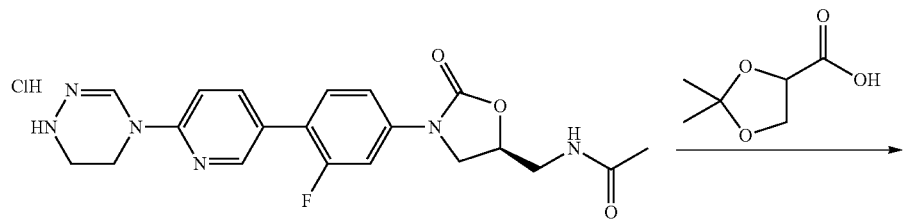

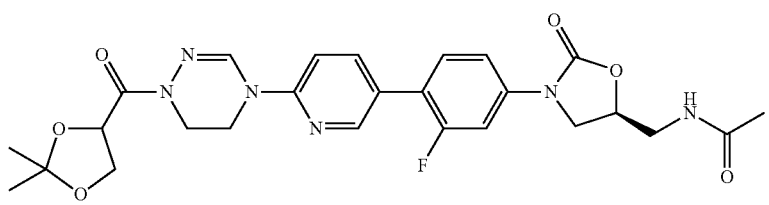

0.12 g (0.22 mmol) of Compound 20 was obtained (yield: 50%) as white solid using glyceric acid acetoaceto in the same manner as in Example 11.

$^1$H NMR (600 MHz, DMSO d-$_6$) δ 8.47 (s, 1H), 8.23 (t, J=6.0 Hz, 1H), 7.98 (s, 1H), 7.96 (d, J=8.4 Hz, 1H), 7.60 (m, 2H), 7.39 (dd, J$_1$=9.0 Hz, J$_2$=1.8 Hz, 1H), 7.32 (d, J=8.8 Hz, 1H), 5.18 (t, 6.6 Hz, 1H), 4.73 (m, 1H), 4.26 (dd, J$_1$=7.8 Hz, J$_2$=7.8 Hz, 1H), 4.13 (t, J=9.0 Hz, 1H), 4.92 (m, 3H), 3.85 (m, 2H), 3.74 (dd, J$_1$=9.0 Hz, J$_2$=6.6 Hz, 1H), 3.40 (t, J=5.4 Hz, 2H), 1.80 (s, 3H), 1.36 (s, 3H), 1.30 (s, 3H)

LCMS: 541 (M+H$^+$) for C$_{26}$H$_{29}$FN$_6$O$_6$

Example 21

Preparation of Compound 21

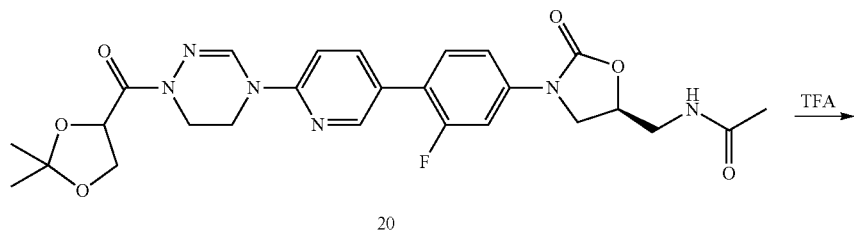

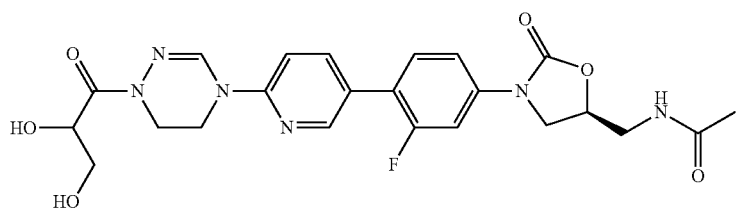

0.12 g (0.22 mmol) of Compound 20 prepared according to Example 20 was dissolved in 2 mL of tetrahydrofuran, 2 mL of TFA was added thereto, and the resulting solution was stirred at room temperature for 1 hour. Subsequently, 15 mL of diethylether was added to the reaction mixture and the resulting mixture was filtered to obtain 65 mg (0.13 mmol) of Compound 21 as a white solid (yield: 59%).

$^1$H NMR (600 MHz, DMSO d-$_6$) δ 8.47 (s, 1H), 8.25 (t, J=5.4 Hz, 1H), 8.00 (s, 1H), 7.96 (d, J=9.0 Hz, 1H), 7.59 (m, 2H), 7.39 (dd, J1=9.0 Hz, J2=2.4 Hz, 1H), 7.32 (d, J1=9.0 Hz, 1H), 4.81 (m, 1H), 4.72 (m, 1H), 4.65 (m, 2H), 4.13 (dd, J1=9.0 Hz, J2=9.0 Hz, 1H), 4.02 (m, 1H), 3.95 (m, 1H), 3.80 (m, 3H), 3.60 (m, 2H), 3.40 (t, J=5.4 Hz, 2H), 1.80 (s, 3H)

LCMS: 501 (M+H$^+$) for $C_{22}H_{25}FN_6O_6$

Example 22

Preparation of Compound 22

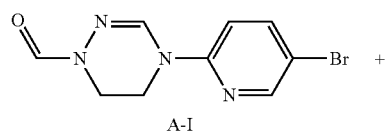

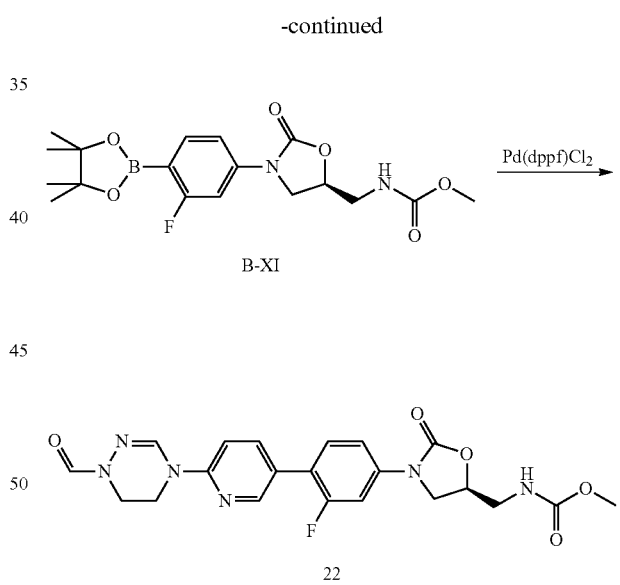

1.04 g (2.28 mmol) of Compound 22 was obtained (yield: 76%) as a gray solid by reacting Compound A-I with Compound B-XI in the same manner as in Example 1.

$^1$H NMR (600 MHz, DMSO d-$_6$) δ 8.51 (m, 2H), 8.06 (s, 1H), 8.00 (d, J=8.4 Hz, 1H), 7.63 (m, 2H), 7.56 (t, J=5.4 Hz, 1H), 7.43 (dd, J$_1$=8.4 Hz, J$_2$=1.8 Hz, 1H), 7.35 (d, J=9.0 Hz, 1H), 4.76 (m, 1H), 4.18 (t, J=8.4 Hz, 1H), 3.93 (t, J=4.8 Hz, 2H), 3.88 (t, J=4.8 Hz, 2H), 3.82 (dd, J$_1$=9.0 Hz, J$_2$=6.0 Hz, 1H), 3.54 (s, 3H), 3.38 (m, 2H)

LCMS: 457 (M+H$^+$) for $C_{21}H_{21}FN_6O_5$

Example 23

Preparation of Compound 23

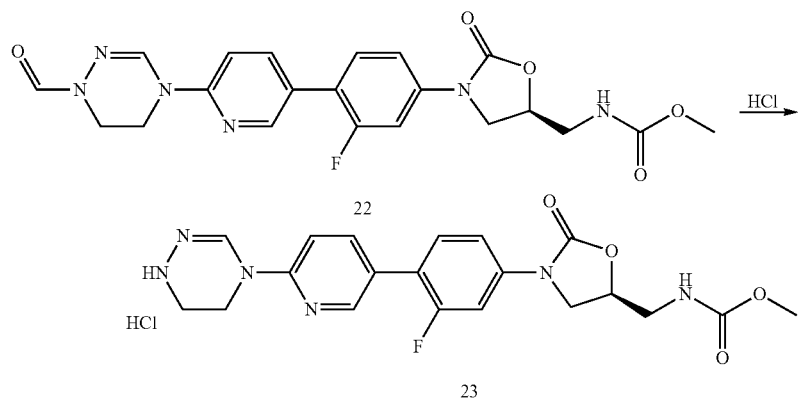

1 g (2.19 mmol) of brown solid-type Compound 23 was quantitatively obtained by treating Compound 22 with hydrochloric acid in the same manner as in Example 2.

$^1$H NMR (600 MHz, DMSO d-$_6$) δ 8.51 (m, 2H), 8.06 (s, 1H), 8.00 (d, J=8.4 Hz, 1H), 7.63 (m, 2H), 7.56 (t, J=5.4 Hz, 1H), 7.43 (dd, J$_1$=8.4 Hz, J$_2$=1.8 Hz, 1H), 7.35 (d, J=9.0 Hz, 1H), 4.76 (m, 1H), 4.18 (t, J=8.4 Hz, 1H), 3.93 (t, J=4.8 Hz, 2H), 3.88 (t, J=4.8 Hz, 2H), 3.82 (dd, J$_1$=9.0 Hz, J$_2$=6.0 Hz, 1H), 3.54 (s, 3H), 3.38 (m, 2H)

LCMS: 457 (M+H$^+$) for C$_{21}$H$_{21}$FN$_6$O$_5$

Example 24

Preparation of Compound 24

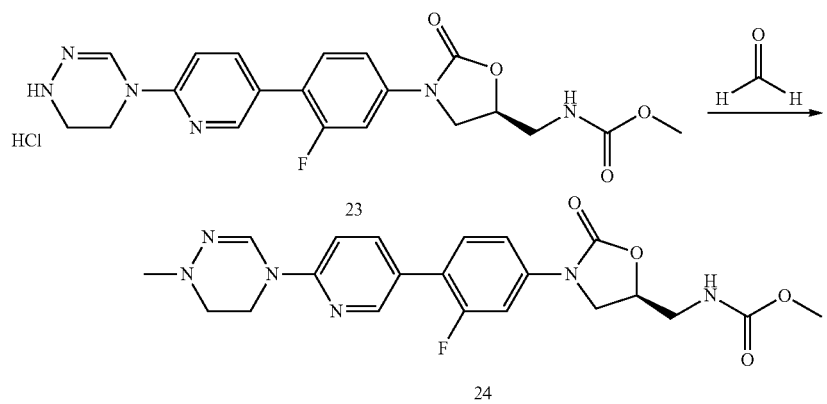

153 mg (0.35 mmol) of yellow solid-type Compound 24 was obtained (yield: 81%) from Compound 23 in the same manner as in Example 3.

$^1$H NMR (600 MHz, CDCl$_3$) δ 8.45 (s, 1H), 7.98 (s, 1H), 7.81 (m, 1H), 7.54 (dd, J$_1$=13.2 Hz, J$_2$=2.4 Hz, 1H), 7.41 (t, J=8.4 Hz, 1H), 7.31 (dd, J$_1$=8.4 Hz, J$_2$=2.4 Hz, 1H), 6.86 (d, J=8.4 Hz, 1H), 5.14 (m, 1H), 4.81 (m, 1H), 4.09 (t, J=8.4 Hz, 1H), 3.94 (t, J=4.8 Hz, 2H), 3.85 (t, J=8.4 Hz, 1H), 3.69 (s, 3H), 3.64 (m, 1H), 3.58 (m, 1H), 3.03 (t, J=4.8 Hz, 2H), 2.84 (s, 3H)

LCMS: 443 (M+H$^+$) for C$_{21}$H$_{23}$FN$_6$O$_4$

Example 25

Preparation of Compound 25

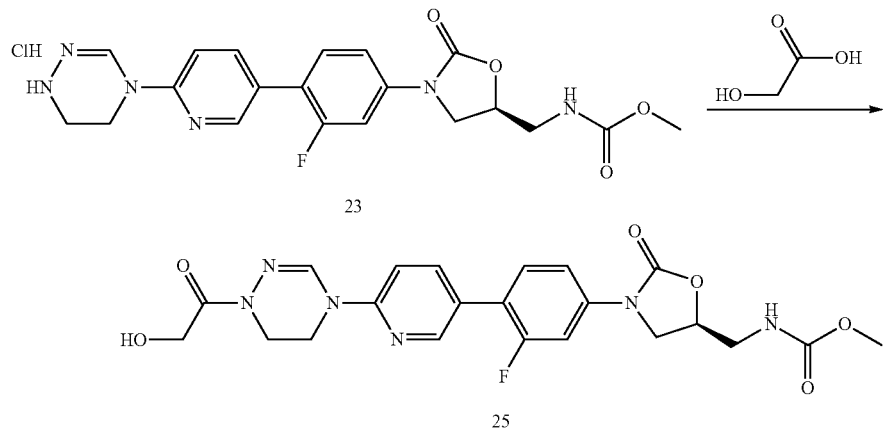

55 mg (0.11 mmol) of Compound 25 was obtained (yield: 18%) as a white solid from Compound 23 in the same manner as in Example 11.

$^1$H NMR (600 MHz, CDCl$_3$) δ 8.05 (s, 1H), 7.93 (s, 1H), 7.89 (d, J=8.4 Hz, 1H), 7.71 (dd, J$_1$=12.6 Hz, J$_2$=2.4 Hz, 1H), 7.43 (t, J=8.4 Hz, 1H), 7.34 (dd, J$_1$=8.4 Hz, J$_2$=2.4 Hz, 1H), 6.96 (d, J=7.8 Hz, 1H), 5.12 (m, 1H), 4.82 (m, 1H), 4.55 (d, J=4.8 Hz, 2H), 4.11 (t, J=5.4 Hz, 2H), 4.06 (m, 1H), 3.95 (t, J=5.4 Hz, 2H), 3.87 (t, J=7.8 Hz, 1H), 3.70 (s, 3H), 3.65 (m, 1H), 3.57 (m, 1H)

LCMS: 487 (M+H$^+$) for C$_{22}$H$_{23}$FN$_6$O$_6$

Example 26

Preparation of Compound 26

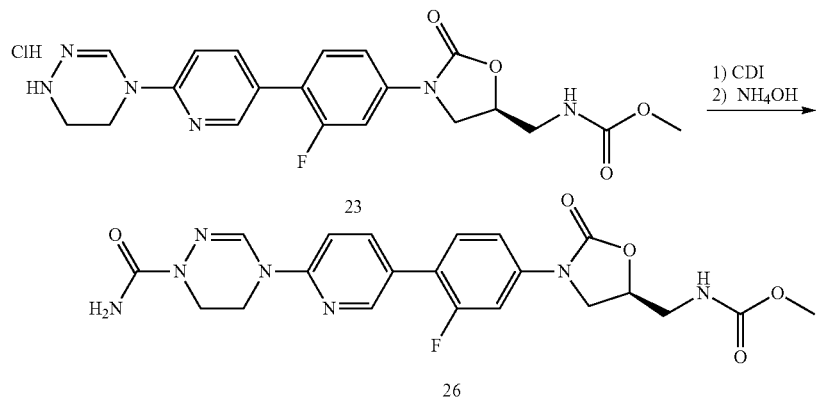

35 mg (0.07 mmol) of Compound 26 was obtained (yield: 32%) as a white solid from Compound 23 in the same manner as in Example 17.

$^1$H NMR (600 MHz, DMSO d-$_6$) δ 8.50 (s, 1H), 7.98 (d, J=9.0 Hz, 1H), 7.95 (s, 1H), 7.63 (m, 2H), 7.56 (m, 1H), 7.43 (d, J=9.0 Hz, 1H), 7.30 (d, J=9.0 Hz, 1H), 6.44 (s, 2H), 4.76 (m, 1H), 4.18 (t, J=9.6 Hz, 1H), 3.90 (t, J=4.8 Hz, 2H), 3.81 (m, 2H), 3.54 (s, 3H), 3.36 (m, 3H)

LCMS: 472 (M+H$^+$) for C$_{21}$H$_{22}$FN$_7$O$_5$

Example 27

Preparation of Compound 27

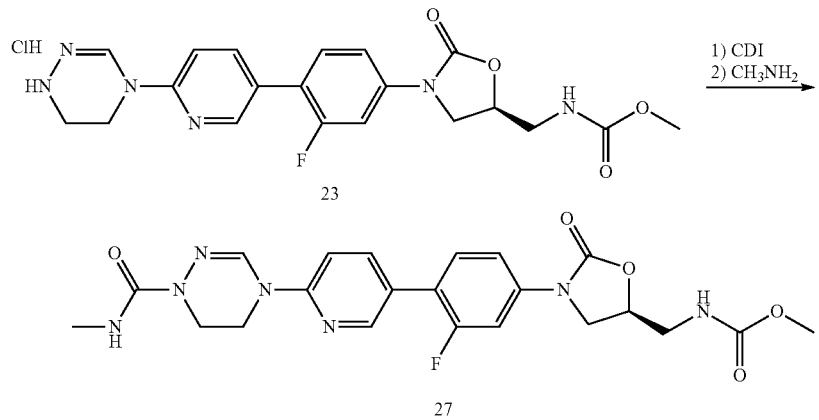

56 mg (0.12 mmol) of Compound 27 was obtained (yield: 46%) as a white solid from Compound 23 in the same manner as in Example 16.

$^1$H NMR (600 MHz, CDCl$_3$) δ 8.48 (s, 1H), 7.90 (s, 1H), 7.86 (d, J=9.0 Hz, 1H), 7.56 (d, J=12.6 Hz, 1H), 7.42 (t, J=9.0 Hz, 1H), 7.33 (d, J=6.0 Hz, 1H), 6.91 (d, J=8.4 Hz, 1H), 6.34 (d, J=4.8 Hz, 1H), 5.14 (m, 1H), 4.81 (m, 1H), 4.10 (t, J=8.4 Hz, 1H), 4.01 (t, J=4.8 Hz, 2H), 3.90 (t, J=4.8 Hz, 2H), 3.86 (t, J=7.8 Hz, 1H), 3.69 (s, 3H), 3.64 (m, 1H), 3.58 (m, 1H), 2.91 (d, J=4.8 Hz, 3H)

LCMS: 486 (M+H$^+$) for C$_{22}$H$_{24}$FN$_7$O$_5$

Example 28

Preparation of Compound 28

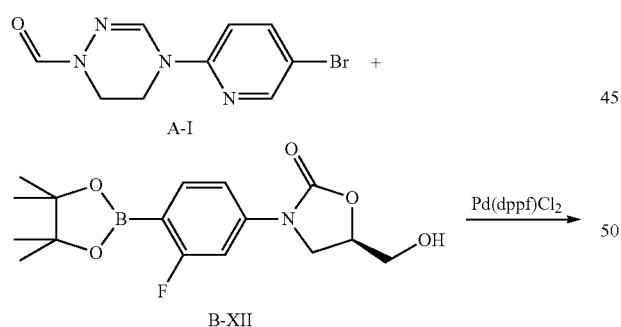

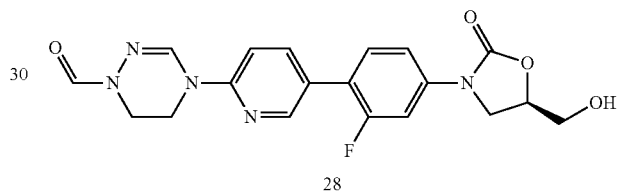

200 mg (0.50 mmol) of Compound 28 was obtained (yield: 36%) as a white solid by reacting Compound A-I and Compound B-XII in the same manner as in Example 1.

$^1$H NMR (400 MHz, DMSO d-$_6$) δ 8.50 (s, 1H), 8.49 (s, 1H), 8.05 (s, 1H), 7.99 (d, J=8.4 Hz, 1H), 7.63 (m, 2H), 7.45 (dd, J$_1$=8.4 Hz, J$_2$=1.8 Hz, 1H), 7.33 (d, J=9.6 Hz, 1H), 5.24 (t, J=5.4 Hz, 1H), 4.73 (m, 1H), 4.18 (dd, J$_1$=8.4 Hz, J$_2$=8.4 Hz, 1H), 3.89 (m, 5H), 3.67 (m, 1H), 3.58 (m, 1H)

LCMS: 400 (M+H$^+$) for C$_{19}$H$_{18}$FN$_5$O$_4$

Example 29

Preparation of Compound 29

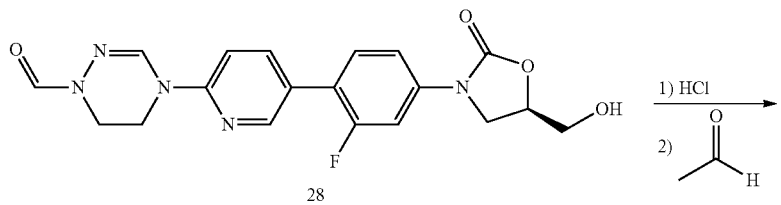 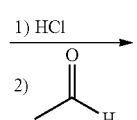

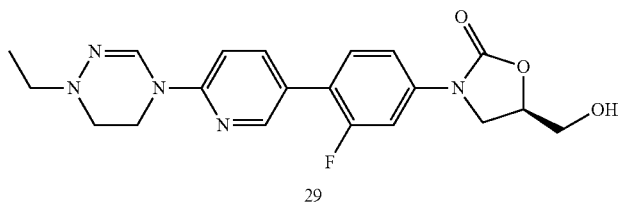

29

55 mg (0.12 mmol) of Compound 29 was obtained (yield: 28%) as a white solid from Compound 28 in the same manner as in Examples 2 and 4.

$^1$H NMR (600 MHz, DMSO d-$_6$) δ 8.43 (s, 1H), 7.94 (s, 1H), 7.90 (d, J=9.0 Hz, 1H), 7.62 (m, 2H), 7.42 (dd, J$_1$=9.0 Hz, J$_2$=2.4 Hz, 1H), 7.17 (d, J=8.4 Hz, 1H), 4.75 (m, 1H), 4.14 (dd, J$_1$=9.0 Hz, J$_2$=9.0 Hz, 1H), 3.87 (dd, J$_1$=9.0 Hz, J$_2$=6.0 Hz, 1H), 3.73 (m, 1H), 3.58 (m, 1H), 3.43 (t, J=5.4 Hz, 2H), 2.97 (m, 4H), 1.31 (t, J=5.4 Hz, 3H)

LCMS: 400 (M+H$^+$) for C$_{20}$H$_{22}$FN$_5$O$_3$

Example 30

Preparation of Compound 30

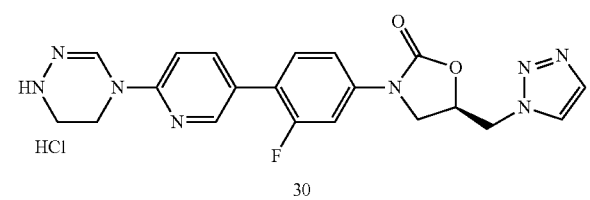

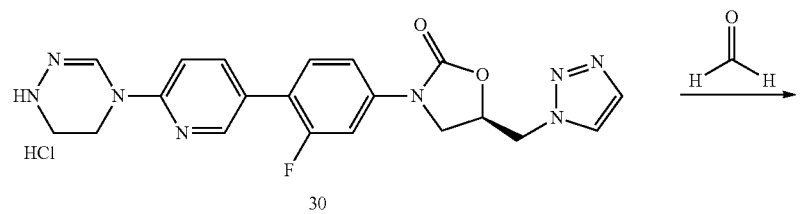

30

900 mg (1.96 mmol) of Compound 30 was obtained (yield: 68%) as a brown solid by reacting Compound A-I and Compound B-IX in the same manner as in Examples 1 and 2.

$^1$H NMR (600 MHz, DMSO d-$_6$) δ 9.00 (s, 1H), 8.61 (s, 1H), 8.20 (s, 1H), 8.14 (d, J=8.4 Hz, 1H), 7.78 (s, 1H), 7.66 (t, J=9.0 Hz, 1H), 7.62 (m, 1H), 7.56 (s, 1H), 7.40 (dd, J$_1$=9.0 Hz, J$_2$=2.4 Hz, 1H), 5.19 (m, 1H), 4.87 (d, J=4.8 Hz, 2H), 4.30 (t, J=9.0 Hz, 1H), 4.03 (t, J=4.8 Hz, 2H), 3.96 (m, 2H), 3.66 (m, 1H), 3.46 (m, 2H)

LCMS: 423 (M+H$^+$) for C$_{20}$H$_{19}$FN$_8$O$_2$

Example 31

Preparation of Compound 31

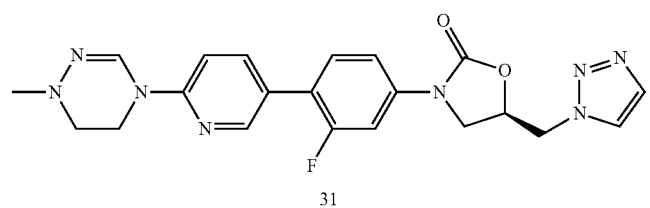

68 mg (0.15 mmol) of Compound 31 was obtained (yield: 63%) as a brown solid from Compound 30 in the same manner as in Example 3.

$^1$H NMR (600 MHz, DMSO d-$_6$) δ 8.44 (s, 1H), 8.19 (s, 1H), 7.95 (s, 1H), 7.91 (d, J=9.0 Hz, 1H), 7.77 (s, 1H), 7.60 (t, J=8.4 Hz, 1H), 7.54 (dd, J$_1$=13.8 Hz, J$_2$=1.8 Hz, 1H), 7.36 (dd, J$_1$=8.4 Hz, J$_2$=2.4 Hz, 1H), 7.16 (d, J=9.0 Hz, 1H), 5.18 (m, 1H), 4.86 (m, 1H), 4.29 (t, J=9.0 Hz, 1H), 3.95 (m, 1H), 3.84 (t, J=4.8 Hz, 2H), 2.95 (t, J=4.8 Hz, 2H), 2.68 (s, 3H)

LCMS: 437 (M+H$^+$) for C$_{21}$H$_{21}$FN$_8$O$_2$

Example 32

Preparation of Compound 32

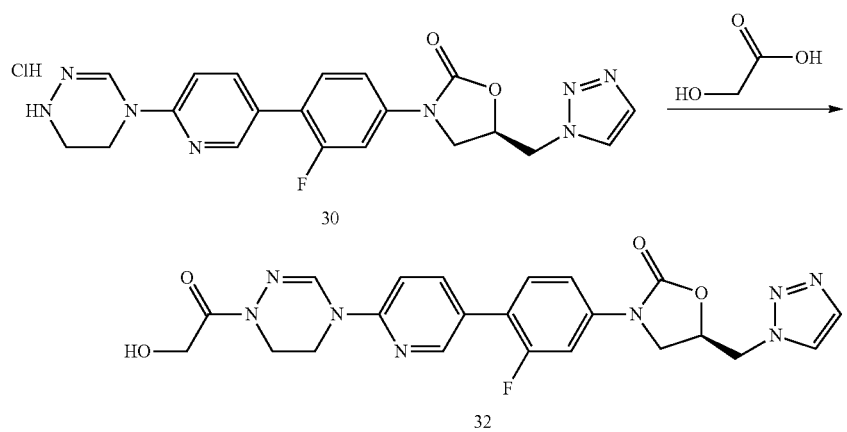

J=8.4 Hz, 1H), 7.55 (d, J=13.2 Hz, 1H), 7.38 (d, J=8.4 Hz, 1H), 7.35 (d, J=9.0 Hz, 1H), 5.19 (m, 1H), 4.86 (d, J=4.2 Hz, 2H), 4.37 (s, 2H), 4.29 (t, J=9.0 Hz, 1H), 3.95 (m, 1H), 3.93 (m, 4H)

LCMS: 481 (M+H$^+$) for C$_{21}$H$_{22}$FN$_8$O$_4$

Example 33

Preparation of Compound 33

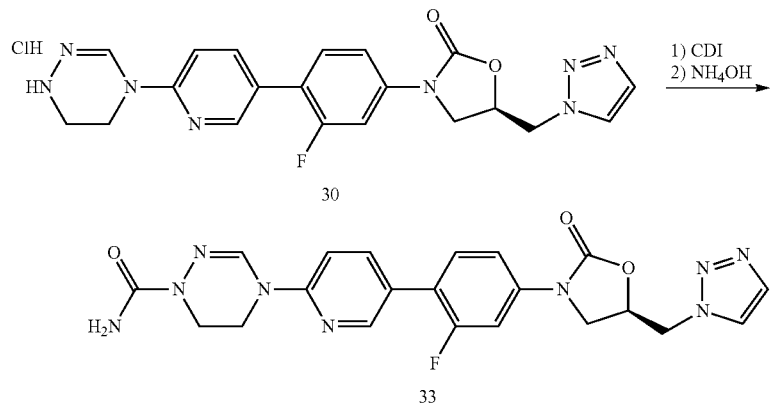

84 mg (0.17 mmol) of Compound 32 was obtained (yield: 35%) as a yellow solid from Compound 30 in the same manner as in Example 11.

$^1$H NMR (600 MHz, DMSO d-$_6$) δ 8.51 (s, 1H), 8.19 (s, 1H), 8.02 (s, 1H), 7.99 (d, J=8.4 Hz, 1H), 7.78 (s, 1H), 7.62 (t, 225 mg (0.48 mmol) of Compound 33 was obtained (yield: 71%) as a brown solid from Compound 30 in the same manner as in Example 17.

$^1$H NMR (600 MHz, DMSO d-$_6$) δ 8.49 (s, 1H), 8.19 (s, 1H), 7.97 (d, J=9.0 Hz, 1H), 7.95 (s, 1H), 7.78 (s, 1H), 7.62 (t,

J=9.0 Hz, 1H), 7.55 (d, J=13.2 Hz, 1H), 7.38 (d, J=8.4 Hz, 1H), 7.30 (d, J=9.0 Hz, 1H), 6.44 (s, 2H), 5.18 (m, 1H), 4.86 (d, J=4.8 Hz, 2H), 4.29 (t, J=9.0 Hz, 1H), 3.96 (m, 1H), 3.90 (t, J=4.8 Hz, 2H), 3.82 (t, J=4.8 Hz, 2H)

LCMS: 466 (M+H$^+$) for $C_{21}H_{20}FN_9O_3$

Example 34

Preparation of Compound 34

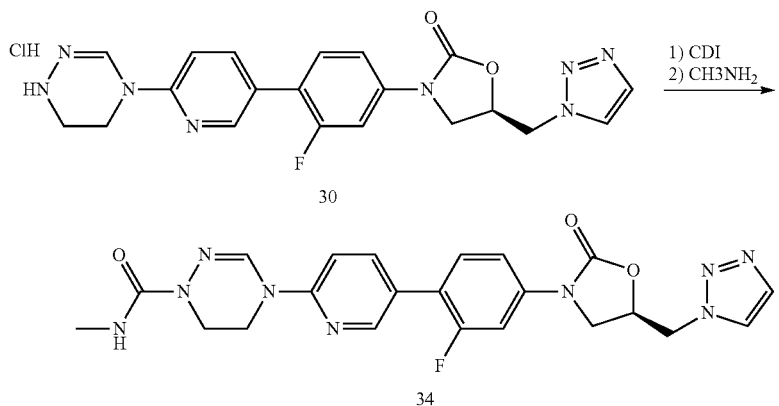

188 mg (0.39 mmol) of Compound 34 was obtained (yield: 57%) as a white solid from Compound 30 in the same manner as in Example 16.

$^1$H NMR (600 MHz, DMSO d-$_6$) δ 8.49 (s, 1H), 8.19 (s, 1H), 7.96 (m, 2H), 7.78 (s, 1H), 7.62 (t, J=9.0 Hz, 1H), 7.55 (m, 1H), 7.38 (m, 1H), 7.29 (d, J=9.0 Hz, 1H), 6.97 (m, 1H), 5.19 (m, 1H), 4.86 (d, J=4.8 Hz, 2H), 4.29 (t, J=9.0 Hz, 1H), 3.95 (m, 1H), 3.90 (t, J=4.8 Hz, 2H), 3.81 (t, J=4.8 Hz, 2H), 2.67 (d, J=4.2 Hz, 3H)

LCMS: 480 (M+H$^+$) for $C_{22}H_{22}FN_9O_3$

Example 35

Preparation of Compound 35

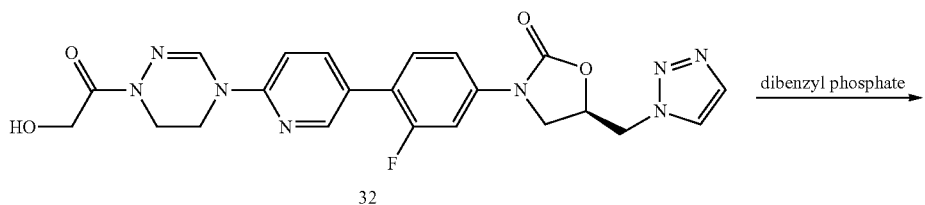

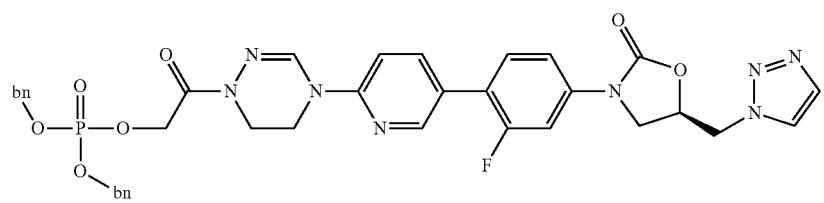

90 mg (0.12 mmol) of Compound 35 was obtained (yield: 68%) as a white solid from Compound 32 in the same manner as in Example 14.

$^1$H NMR (400 MHz, CDCl$_3$) δ 8.48 (s, 1H), 7.87 (m, 2H), 7.81 (d, J=0.8 Hz, 1H), 7.77 (dd, J=0.8 Hz, 1H), 7.45 (dd, J$_1$=8.8 Hz, J$_2$=2.4 Hz, 1H), 7.35 (m, 1H), 7.20 (dd, J$_1$=8.8 Hz, J$_2$=2.4 Hz, 1H), 6.94 (d, J=8.8 Hz, 1H), 5.12 (m, 4H), 5.14 (m, 3H) 4.83 (d, J=4.0 Hz, 2H), 4.15 (dd, J$_1$=9.6 Hz, J$_2$=9.6 Hz, 1H), 4.03 (m, 3H), 3.91 (t, J=5.2 Hz, 2H)

LCMS: 741 (M+H$^+$) for $C_{36}H_{34}FN_8O_7P$

Example 36

Preparation of Compound 36

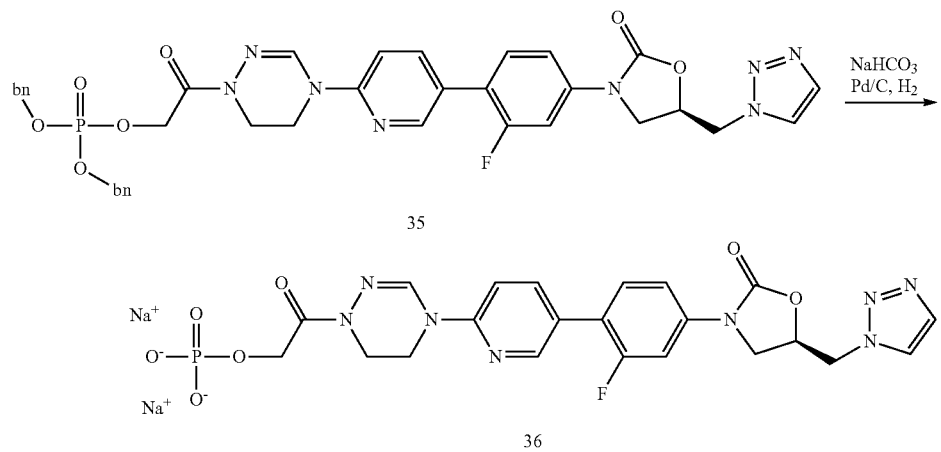

50 mg (0.08 mmol) of Compound 36 was obtained (yield: 74%) as a white solid from Compound 35 in the same manner as in Example 15.

$^1$H NMR (600 MHz, D$_2$O) δ 8.17 (s, 1H), 7.90 (s, 1H), 7.77 (d, J=7.8 Hz, 1H), 7.62 (s, 1H), 7.58 (s, 1H), 7.26 (dd, J$_1$=8.4 Hz, J$_2$=8.4 Hz, 1H), 7.05 (d, J=12.6 Hz, 1H), 6.97 (d, J=7.8 Hz, 1H), 6.93 (d, J=8.4 Hz, 1H), 5.04 (m, 1H), 4.73 (m, 2H), 4.60 (m, 2H), 4.13 (dd, J$_1$=8.4 Hz, J$_2$=8.4 Hz, 1H), 3.75 (m, 3H), 3.37 (m, 2H)

LCMS: 561 (M+H$^+$) for C$_{22}$H$_{22}$FN$_8$O$_7$P

Example 37

Preparation of Compound 37

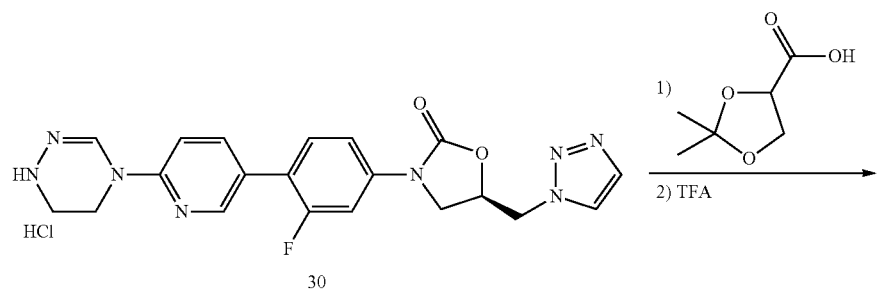

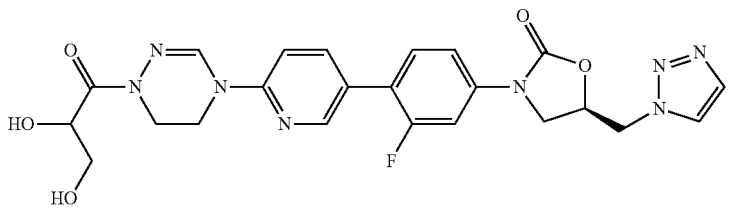

17 mg (0.03 mmol) of Compound 37 was obtained (yield: 30%) as a yellow solid from Compound 30 in the same manner as in Examples 20 and 21.

$^1$H NMR (600 MHz, DMSO) δ 8.51 (s, 1H), 8.18 (s, 1H), 8.04 (s, 1H), 7.99 (d, J=9.0 Hz, 1H), 7.77 (s, 1H), 7.62 (dd, J$_1$=8.4 Hz, J$_2$=8.4 Hz, 1H), 7.55 (d, J=13.8 Hz, 1H), 7.36 (m, 2H), 5.17 (m, 1H), 4.86 (d, J=4.2 Hz, 2H), 4.29 (dd, J$_1$=9.0 Hz, J$_2$=9.0 Hz, 1H), 4.04 (m, 1H), 3.95 (m, 3H), 3.83 (m, 2H), 3.64 (m, 1H), 3.55 (m, 1H)

LCMS: 511 (M+H$^+$) for C$_{23}$H$_{23}$FN$_8$O$_5$

Example 38

Preparation of Compound 38

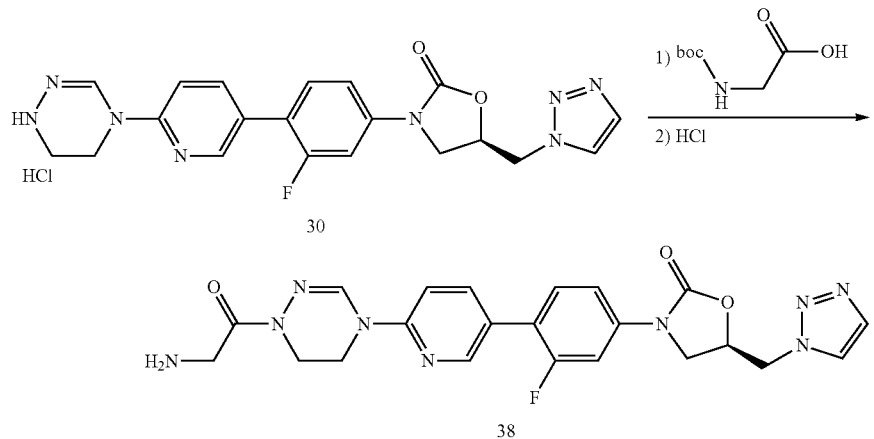

25 mg (0.05 mmol) of Compound 38 was obtained (yield 70%) as a light yellow solid from Compound 30 in the same manner as in Examples 18 and 19.

$^1$H NMR (400 MHz, DMSO) δ 8.53 (s, 1H), 8.20 (d, J=1.2 Hz, 1H), 8.13 (s, 1H), 8.00 (d, J=7.2 Hz, 1H), 7.77 (d, J=1.2 Hz, 1H), 7.63 (dd, J1=8.8 Hz, J$_2$=8.8 Hz, 1H), 7.55 (dd, J$_1$=13.2 Hz, J$_2$=2.0 Hz, 1H), 7.40 (m, 2H), 5.19 (m, 1H), 4.87 (d, J=5.4 Hz, 2H), 4.29 (dd, J$_1$=9.2 Hz, J$_2$=9.2 Hz, 1H), 4.04 (m, 3H), 3.96 (m, 4H),

LCMS: 480 (M+H$^+$) for C$_{22}$H$_{22}$FN$_9$O$_3$

Example 39

Preparation of Compound 39

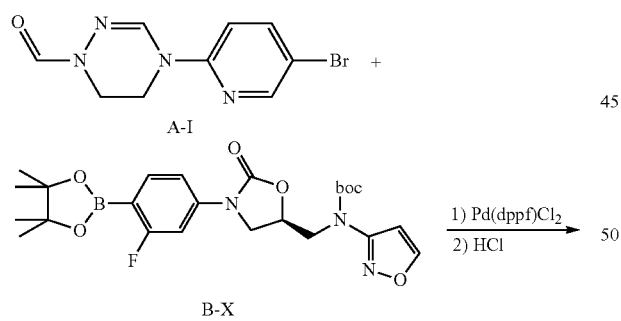

1.1 g (2.53 mmol) of Compound 39 was obtained (yield: 45%) as a yellow solid by reacting Compound A-I and Compound B-X in the same manner as in Examples 1 and 2.

$^1$H NMR (600 MHz, DMSO-$_6$) δ 8.98 (s, 1H), 8.62 (s, 1H), 8.40 (d, J=1.8 Hz, 1H), 8.14 (d, J=9.0 Hz, 1H), 7.67 (m, 2H), 7.58 (d, J=9 Hz, 1H), 7.46 (dd, J$_1$=9.0 Hz, J$_2$=2.4 Hz, 1H), 6.02 (d, J=1.8 Hz, 1H), 4.93 (m, 1H), 4.22 (dd, J$_1$=9.0 Hz, J$_2$=9.0 Hz 1H), 4.12 (t, J=5.4 Hz, 2H), 3.88 (dd, J=6.6 Hz, 1H), 3.46 (m, 4H)

LCMS: 439 (M+H$^+$) for C$_{21}$H$_{21}$FN$_7$O$_3$

Example 40

Preparation of Compound 40

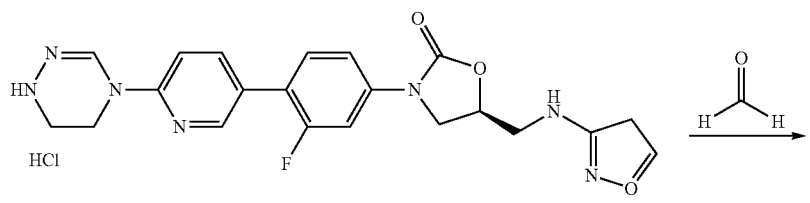

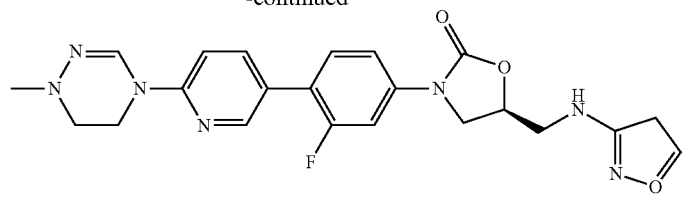

40

45 mg (0.10 mmol) of Compound 40 was obtained (yield: 23%) as a white solid from Compound 39 in the same manner as in Example 3.

$^1$H NMR (600 MHz, DMSO) δ 8.94 (s, 1H), 8.60 (s, 1H), 8.39 (d, J=1.8 Hz, 1H), 8.13 (d, J=9.0 Hz, 1H), 7.66 (m, 2H), 7.57 (d, J=9.0 Hz, 1H), 7.46 (dd, $J_1$=8.4 Hz, $J_2$=2.4 Hz, 1H), 6.01 (d, J=1.8 Hz, 1H), 4.92 (m, 1H), 4.21 (dd, $J_1$=9.0 Hz, $J_2$=9.0 Hz, 1H), 4.12 (t, J=5.4 Hz, 2H), 3.88 (dd, $J_1$=9.0 Hz, $J_2$=6.6 Hz, 1H), 3.45 (m, 4H), 2.92 (s, 3H)

LCMS: 452 (M+H$^+$) for $C_{22}H_{22}FN_7O_3$

Example 41

Preparation of Compound 41

28 mg (0.06 mmol) of Compound 41 was obtained (yield: 15%) as a white solid from Compound 39 in the same manner as in Example 11.

$^1$H NMR (600 MHz, DMSO) δ 8.05 (s, 1H), 8.40 (s, 1H), 8.00 (m, 2H), 7.63 (m, 2H), 7.44 (d, J=7.8 Hz, 1H), 7.34 (d, J=8.4 Hz, 1H), 6.60 (s, 1H), 6.01 (s, 1H), 4.92 (m, 1H), 4.66 (s, 1H), 4.36 (m, 2H), 4.20 (dd, $J_1$=8.4 Hz, $J_2$=8.4 Hz, 1H), 3.93 (s, 4H), 3.86 (m, 1H), 3.46 (s, 2H)

LCMS: 496 (M+H$^+$) for $C_{23}H_{22}FN_7O_5$

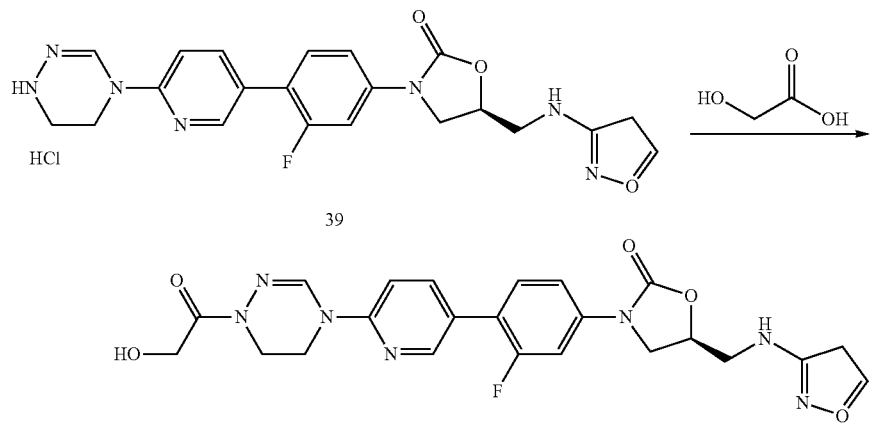

Example 42

Preparation of Compound 42

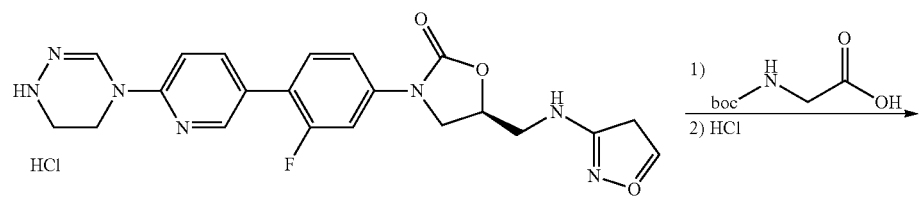

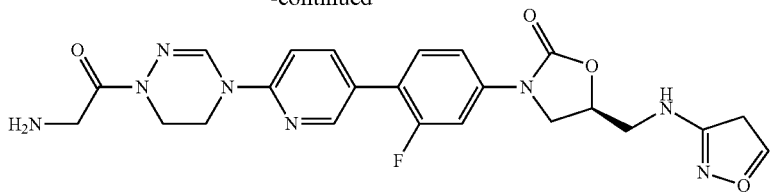

42

20 mg (0.04 mmol) of Compound 42 was obtained (yield: 40%) as a white solid from Compound 39 in the same manner as in Examples 18 and 19.

$^1$H NMR (600 MHz, DMSO) δ 8.55 (s, 1H), 8.41 (d, J=0.6 Hz, 1H), 8.24 (s, 2H), 8.14 (s, 1H), 8.03 (d, J=8.4 Hz, 1H), 7.65 (m, 2H), 7.45 (dd, J$_1$=9.0 Hz, J$_2$=2.4 Hz, 1H), 7.40 (d, J=8.4 Hz, 1H), 6.01 (d, J=1.2 Hz, 1H), 4.93 (m, 1H), 4.21 (dd, J$_1$=9.0 Hz, J$_2$=9.0 Hz, 1H), 4.00 (m, 4H), 3.87 (dd, J$_1$=9.0 Hz, J$_2$=6.6 Hz, 1H), 3.46 (m, 2H), 1.29 (m, 2H)

LCMS: 495 (M+H$^+$) for $C_{23}H_{23}FN_8O_4$

Example 43

Preparation of Compound 43

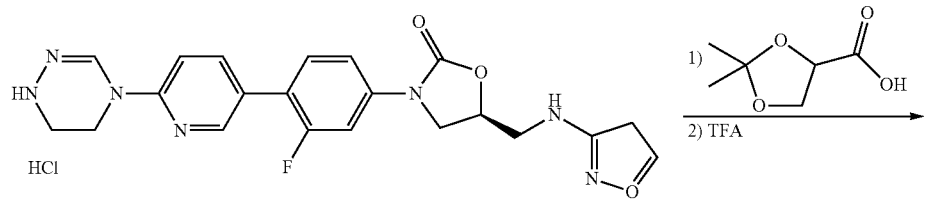

62 mg (0.12 mmol) of white solid-type Compound 43 was obtained (yield: 41%) from Compound 39 in the same manner as in Examples 20 and 21.

$^1$H NMR (600 MHz, DMSO) δ 8.52 (s, 1H), 8.41 (d, J=1.2 Hz, 1H), 8.05 (s, 1H), 8.00 (d, J=9.0 Hz, 1H), 7.64 (m, 2H), 7.44 (d, J=7.2 Hz, 1H), 7.36 (d, J=8.4 Hz, 1H), 6.61 (s, 1H), 6.01 (d, J=1.2 Hz, 1H), 4.92 (m, 1H), 4.86 (m, 1H), 4.21 (dd, J$_1$=8.4 Hz, J$_2$=8.4 Hz, 1H), 4.03 (m, 2H), 3.84 (m, 5H), 3.47 (m, 2H)

LCMS: 526 (M+H$^+$) for $C_{24}H_{24}FN_7O_6$

Example 44

Preparation of Compound 44

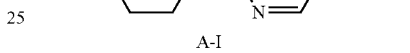

A-I

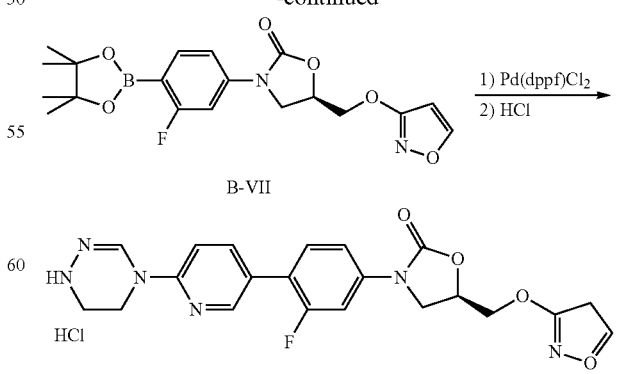

44

887 mg (1.84 mmol) of Compound 44 was obtained (yield: 35%) as a yellow solid by reacting Compound A-I and Compound B-VII in the same manner as in Examples 1 and 2.

$^1$H NMR (600 MHz, DMSO d-$_6$) δ 8.95 (m, 1H), 8.72 (d, J=1.8 Hz, 1H), 8.61 (s, 1H), 8.14 (d, J=7.8 Hz, 1H), 7.69 (m, 2H), 7.55 (d, J=8.4 Hz, 1H), 7.50 (dd, J$_1$=9.0 Hz, J$_2$=2.4 Hz, 1H), 6.41 (d, J=1.8 Hz, 1H), 5.14 (m, 1H), 4.51 (m, 2H), 4.27 (t, J=9.0 Hz, 1H), 3.99 (m, 3H), 3.39 (m, 2H)

LCMS: 440 (M+H$^+$) for C$_{21}$H$_{20}$FN$_6$O$_4$

Example 45

Preparation of Compound 45

54 mg (0.12 mmol) of Compound 45 was obtained (yield: 57%) as a white solid from Compound 44 in the same manner as in Example 3.

$^1$H NMR (600 MHz, CDCl$_3$) δ 8.46 (s, 1H), 8.17 (d, J=1.8 Hz, 1H), 7.99 (s, 1H), 7.82 (m, 1H), 7.57 (dd, J$_1$=13.2 Hz, J$_2$=2.4 Hz, 1H), 7.43 (t, J=9.0 Hz, 1H), 7.36 (dd, J$_1$=8.4 Hz, J$_2$=2.4 Hz, 1H), 6.87 (d, J=8.4 Hz, 1H), 6.02 (d, J=1.8 Hz, 1H), 5.06 (m, 1H), 4.61 (dd, J$_1$=11.4 Hz, J$_2$=3.6 Hz, 1H), 4.53 (dd, J$_1$=12.0 Hz, J$_2$=4.8 Hz, 1H), 4.21 (t, J=9.0 Hz, 1H), 4.02 (dd, J$_1$=9.0 Hz, J$_2$=6.6 Hz, 1H), 3.94 (t, J=5.4 Hz, 2H), 3.03 (t, J=4.8 Hz, 2H), 2.85 (s, 3H)

LCMS: 454 (M+H$^+$) for C$_{22}$H$_{22}$FN$_6$O$_4$

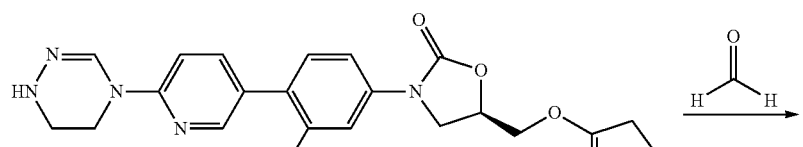

44

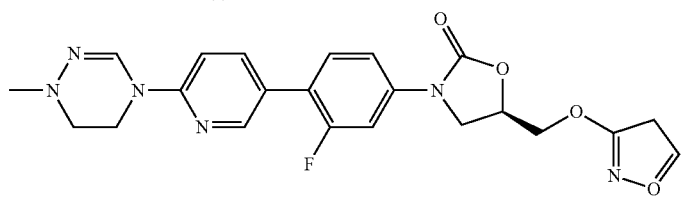

45

Example 46

Preparation of Compound 46

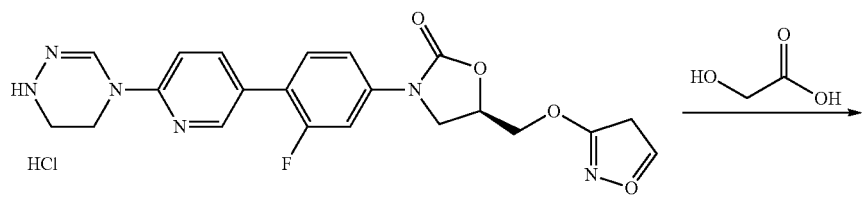

44

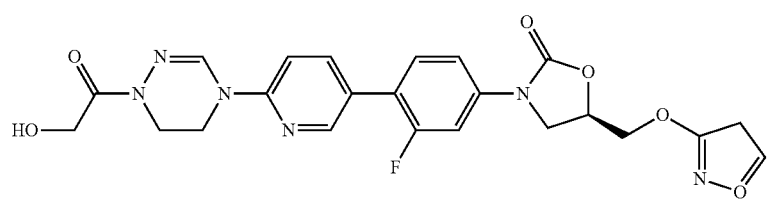

46

88 mg (0.18 mmol) of Compound 46 was obtained (yield: 42%) as a brown solid from Compound 44 in the same manner as in Example 11.

$^1$H NMR (400 MHz, DMSO d-$_6$) δ 8.72 (d, J=1.6 Hz, 1H), 8.52 (s, 1H), 8.01 (m, 1H), 7.64 (m, 2H), 7.47 (dd, J$_1$=8.4 Hz, J$_2$=2.0 Hz, 1H), 7.35 (d, J=8.8 Hz, 1H), 6.41 (d, J=1.6 Hz, 1H), 5.13 (m, 1H), 4.64 (t, J=6.0 Hz, 1H), 4.51 (m, 2H), 4.37 (d, J=6.4 Hz, 2H), 4.26 (t, J=9.2 Hz, 1H), 3.99 (dd, J$_1$=9.2 Hz, J$_2$=6.0 Hz, 1H), 3.93 (m, 4H)

LCMS: 498 (M+H$^+$) for C$_{23}$H$_{22}$FN$_6$O$_6$

Example 47

Preparation of Compound 47

100 mg (0.17 mmol) of Compound 47 was obtained (yield: 80%) as a yellow solid from Compound 44 in the same manner as in Example 18.

$^1$H NMR (400 MHz, DMSO d-$_6$) δ 8.72 (d, J=1.6 Hz, 1H), 8.52 (s, 1H), 8.01 (m, 1H), 7.64 (m, 2H), 7.47 (dd, J$_1$=8.4 Hz, J$_2$=2.0 Hz, 1H), 7.35 (d, J=8.8 Hz, 1H), 6.41 (d, J=1.6 Hz, 1H), 5.13 (m, 1H), 4.64 (t, J=6.0 Hz, 1H), 4.51 (m, 2H), 4.37 (d, J=6.4 Hz, 2H), 4.26 (t, J=9.2 Hz, 1H), 3.99 (dd, J$_1$=9.2 Hz, J$_2$=6.0 Hz, 1H), 3.93 (m, 4H)

LCMS: 498 (M+H$^+$) for C$_{23}$H$_{22}$FN$_6$O$_6$

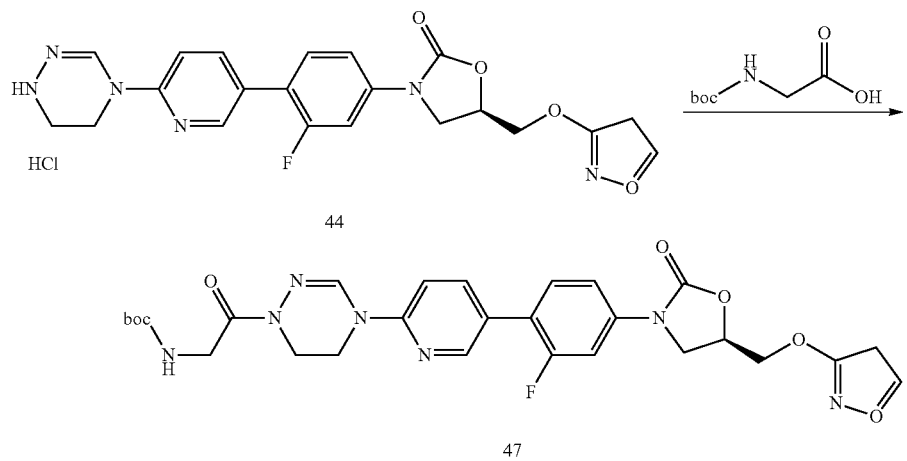

Example 48

Preparation of Compound 48

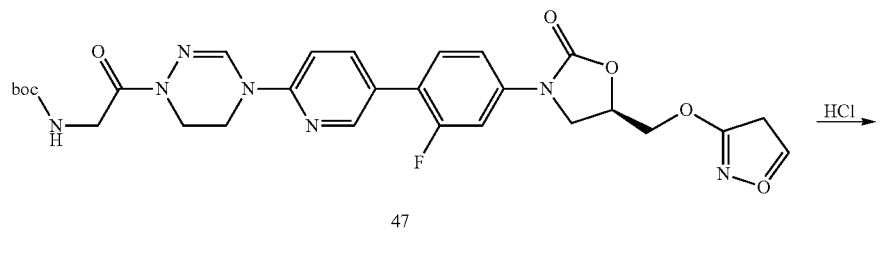

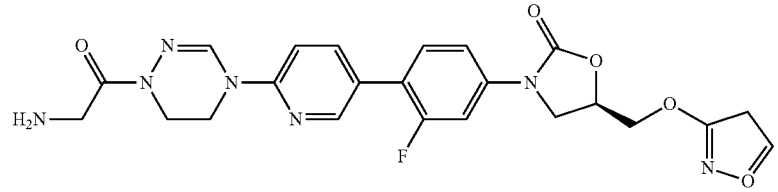

70 mg (0.14 mmol) of Compound 48 was obtained (yield: 88%) as a yellow solid from Compound 47 in the same manner as in Example 19.

$^1$H NMR (600 MHz, DMSO d$_6$) δ 8.72 (d, J=1.8 Hz, 1H), 8.54 (s, 1H), 8.18 (t, J=5.4 Hz, 2H), 8.14 (s, 1H), 8.04 (d, J=9.0 Hz, 1H), 7.65 (m, 2H), 7.48 (dd, J$_1$=9.0 Hz, J$_2$=2.4 Hz, 1H), 7.41 (d, J=9.0 Hz, 1H), 6.41 (d, J=1.8 Hz, 1H), 5.13 (m, 1H), 4.53 (dd, J$_1$=11.4 Hz, J$_2$=3.0 Hz, 1H), 4.49 (dd, J$_1$=11.4 Hz, J$_2$=6.0 Hz, 1H), 4.26 (t, J=9.0 Hz, 1H), 4.03 (m, 2H), 3.98 (m, 5H)

LCMS: 497 (M+H$^+$) for C$_{23}$H$_{23}$FN$_7$O$_5$

Example 49

Preparation of Compound 49

234 mg (0.41 mmol) of Compound 49 was obtained (yield: 79%) as a white solid from Compound 44 in the same manner as in Example 20.

$^1$H NMR (600 MHz, CDCl$_3$) δ 8.50 (s, 1H), 8.18 (d, J=1.8 Hz, 1H), 7.90 (s, 2H), 7.89 (m, 1H), 7.60 (dd, J$_1$=13.2 Hz, J$_2$=2.4 Hz, 1H), 7.44 (t, J=8.4 Hz, 1H), 7.34 (dd, J$_1$=8.4 Hz, J$_2$=2.4 Hz, 1H), 6.97 (d, J=9.0 Hz; 1H), 6.02 (d, J=1.8 Hz, 1H), 5.33 (t, J=6.6 Hz, 1H), 5.07 (m, 1H), 4.61 (dd, J$_1$=11.4 Hz, J$_2$=3.6 Hz, 1H), 4.53 (dd, J$_1$=12.4 Hz, J$_2$=4.8 Hz, 1H), 4.22 (t, J=9.0 Hz, 1H), 4.12 (m, 1H), 4.01 (m, 3H), 3.94 (m, 1H), 3.89 (m, 1H), 1.56 (s, 3H), 1.48 (s, 3H)

LCMS: 568 (M+H$^+$) for C$_{27}$H$_{28}$FN$_6$O$_7$

Example 50

Preparation of Compound 50

88 mg (0.17 mmol) of Compound 50 was obtained (yield: 47%) as a white solid from Compound 49 in the same manner as in Example 21.

$^1$H NMR (600 MHz, DMSO d-$_6$) δ 8.72 (d, J=1.8 Hz, 1H), 8.53 (s, 1H), 8.05 (s, 1H), 8.01 (m, 1H), 7.66 (m, 2H), 7.48 (m, 1H), 7.37 (d, J=9.6 Hz, 1H), 6.41 (d, J=1.8 Hz, 1H), 5.12 (m, 1H), 4.86 (m, 1H), 4.67 (m, 2H), 4.51 (m, 2H), 4.26 (t, J=9.0 Hz, 1H), 4.06 (m, 1H), 4.00 (m, 2H), 3.84 (m, 2H), 3.65 (m, 1H), 3.56 (m, 1H)

LCMS: 528 (M+H$^+$) for C$_{24}$H$_{24}$FN$_6$O$_7$

Example 51

Preparation of Compound 51

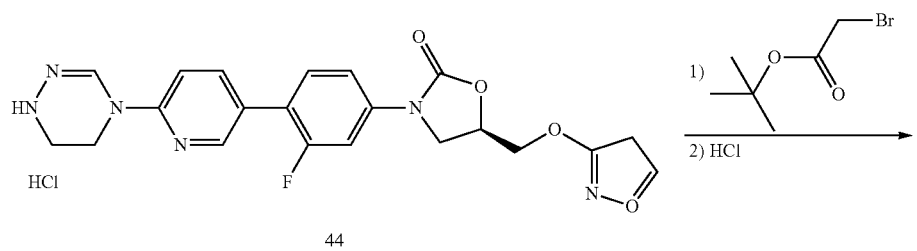

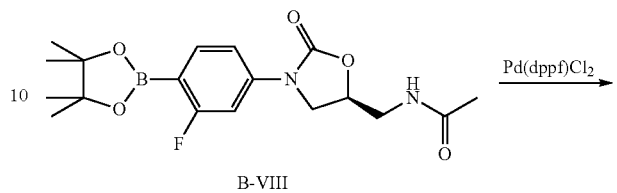

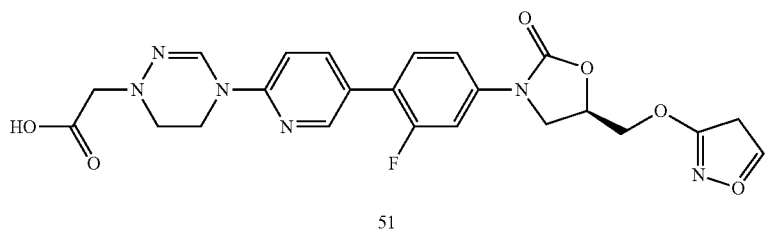

40 mg (0.08 mmol) of Compound 51 was obtained (yield: 34%) as a white solid from Compound 44 in the same manner as in Examples 9 and 10.

$^1$H NMR (600 MHz, DMSO d-$_6$) δ 12.43 (s, 1H), 8.72 (d, J=1.8 Hz, 1H), 8.46 (s, 1H), 7.94 (m, 2H), 7.65 (m, 2H), 7.46 (m, 1H), 7.19 (d, J=9.0 Hz, 1H), 6.42 (d, 1.8 Hz, 1H), 5.13 (m, 1H), 4.51 (dd, J$_1$=11.4 Hz, J$_2$=8.4 Hz, 1H), 4.48 (t, J=6.0 Hz, 1H), 4.26 (t, J=8.4 Hz, 1H), 3.99 (m, 1H), 3.87 (t, J=4.8 Hz, 2H), 3.70 (s, 3H), 3.23 (t, J=4.8 Hz, 2H)

LCMS: 498 (M+H$^+$) for C$_{23}$H$_{22}$FN$_6$O$_6$

Example 52

Preparation of Compound 52

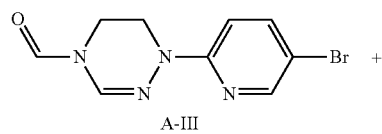

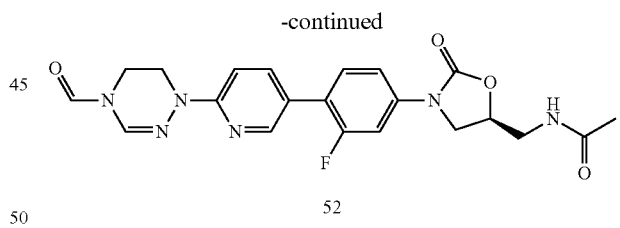

0.3 g (0.90 mmol) of Compound A-III synthesized according to Preparation Example 14 was dissolved in 5 mL of N,N-dimethylformamide, 350 mg of Compound B-VIII synthesized according to Preparation Example 37, 22 mg (0.03 mmol) of PdCl$_2$(dppf), and 0.9 mL of an aqueous 2M sodium carbonate solution were added thereto, and the resulting solution was stirred under a nitrogen atmosphere at 90° C. for 5 hours. The reaction mixture was cooled to room temperature and filtered through celite to remove a residue. The resulting mixture was extracted with 50 mL of ethylacetate and 40 mL of saturated ammonium chloride to obtain an organic layer. The organic layer was concentrated under reduced pressure. A produced solid was washed with 20 mL of ethylacetate and 20 mL of dichloromethane and then dried to obtain 75 mg (0.17 mmol) of Compound 52 as a gray solid (yield: 19%).

$^1$H NMR (600 MHz, CD$_3$OD) δ 8.57 (s, 1H), 8.32 (s, 1H), 7.85~7.81 (m, 2H), 7.61 (m, 1H), 7.50 (m, 2H), 7.35 (m, 1H), 4.18 (m, 2H), 4.11 (m, 2H), 3.91 (m, 2H), 3.87 (m, 1H), 3.57 (m, 2H), 1.97 (s, 3H)

LCMS: 441 (M+H$^+$) for C$_{21}$H$_{21}$FN$_6$O$_4$

Example 53

Preparation of Compound 53

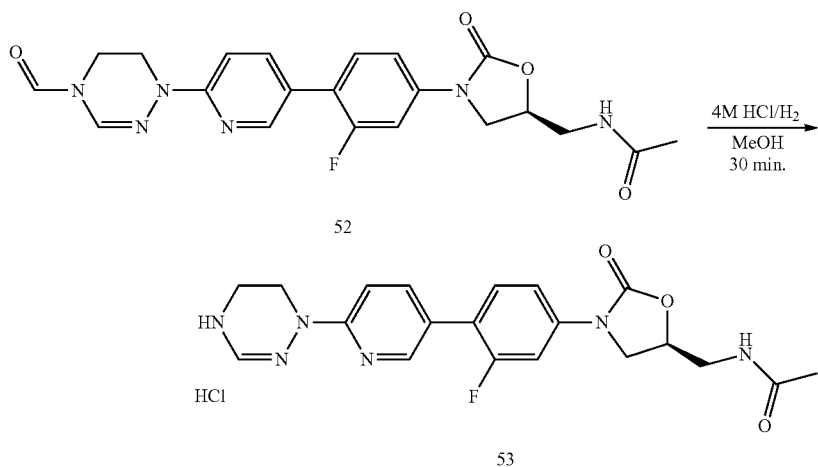

concentrated under reduced pressure to obtain 44 mg (0.10 mnol) of Compound 53 (yield: 98%).

$^1$H NMR (600 MHz, DMSO d-$_6$) δ 8.24 (s, 1H), 7.71 (d, J=9.0 Hz, 1H), 7.55 (m, 1H), 7.42 (m, 1H), 7.37 (d, J=9.0 Hz, 1H), 7.26 (d, J=9.0 Hz, 1H), 6.89 (s, 1H), 6.81 (s, 1H), 4.76 (m, 1H), 4.16 (m, 2H), 3.77 (m, 2H), 3.44~3.37 (m, 4H), 1.84 (s, 3H)

LCMS: 413 (M+H$^+$) for C$_{20}$H$_{21}$FN$_6$O$_3$

Example 54

Preparation of Compound 54

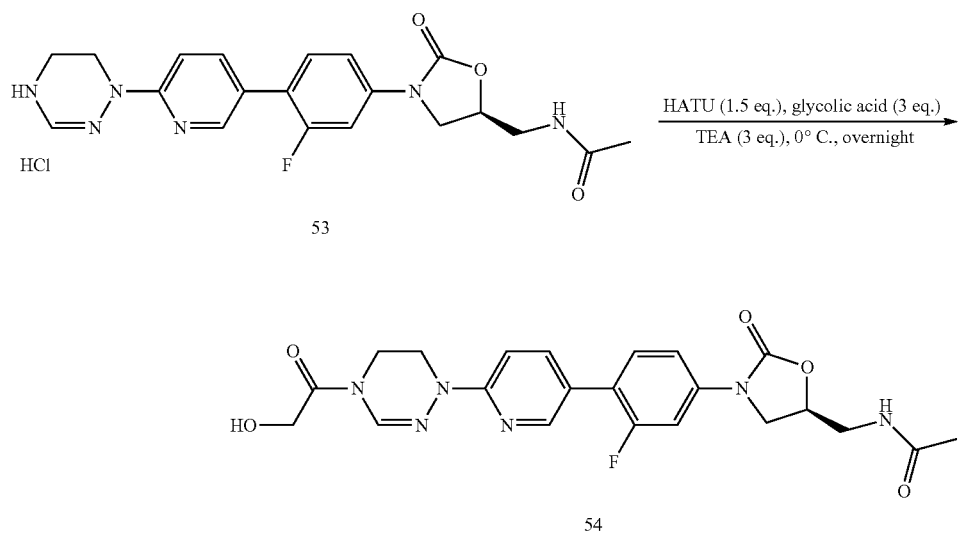

44 mg (0.1 mmol) of Compound 52 synthesized according to Example 52 was dissolved in 7 mL of methanol, 10 mg of 10% Pd/C and 1 mL of 4M hydrochloric acid dissolved in 1,4-dioxane were sequentially added thereto at 0° C., and the resulting solution was stirred under a hydrogen atmosphere for 30 minutes. The reaction mixture was filtered through celite using 30 mL of methanol and then the filtrate was 58.1 mg (0.14 mmol) of Compound 53 synthesized according to Example 53, 80.2 mg (0.21 mmol) of HATU, and 32.2 mg (0.42 mmol) of glycolic acid were dissolved in 1.5 mL of N,N-dimethylformamide, 59 μl (0.42 mmol) of triethylamine was slowly added thereto at 0° C., and the resulting solution was stirred at room temperature for 12 hours. The reaction mixture was extracted with 30 mL of ethylacetate and 30 mL of saturated ammonium chloride to obtain an organic layer. The organic layer was dehydrated using anhydrous sodium sulfate and then concentrated under reduced pressure to obtain a solid product. The solid product was washed with a mixed solution of 5 mL of ethylacetate and 5 mL of n-hexane to obtain 20 mg (0.04 mmol) of Compound 54 as a reddish brown solid (yield: 30%).

$^1$H NMR (600 MHz, DMSO d-$_6$) δ 8.35 (s, 1H), 8.26 (t, J=6.0 Hz, 1H), 7.85 (d, J=8.4 Hz, 1H), 7.61~7.57 (m, 2H), 7.44~7.39 (m, 2H), 5.32 (brs, 1H), 4.76 (m, 1H), 4.41 (brs, 1H), 4.18 (m, 1H), 4.06 (t, J=5.4 Hz, 1H), 3.84~3.76 (m, 2H), 3.42 (t, J=5.4 Hz, 1H), 3.35 (m, 2H), 1.84 (s, 3H)

LCMS: 471 (M+H$^+$) for $C_{22}H_{23}FN_6O_5$

Example 55

Preparation of Compound 55

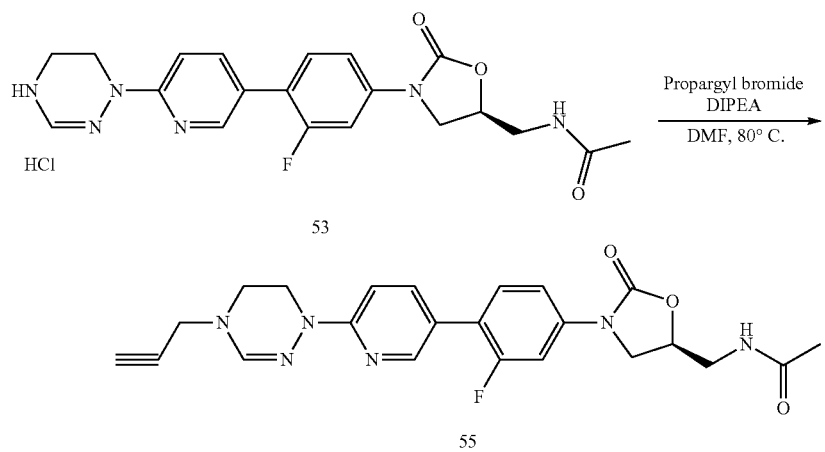

110 mg (0.24 mmol) of Compound 53 synthesized according to Example 53 was dissolved in 2 mL of N,N-dimethylformamide, 0.21 mL (1.22 mmol) of diisopropylethylamine was added thereto, 54 μl (0.36 mmol) of propargyl bromide (80% in toluene) was added dropwise thereto, and the resulting solution was stirred at 80° C. for 5 hours. The reaction mixture was cooled to room temperature and extracted with 20 mL of distilled water and 30 mL of ethylacetate to obtain an organic layer. The organic layer was dehydrated using anhydrous sodium sulfate, concentrated under reduced pressure, and then separated by column chromatography to obtain 14 mg (0.03 mmol) of Compound 55 as a gray solid (yield: 13%).

$^1$H NMR (600 MHz, CDCl$_3$) δ 8.43 (m, 2H), 7.71 (d, J=9.0 Hz, 1H), 7.54 (dd, J$_1$=12.6 Hz, J$_2$=2.4 Hz, 1H), 7.39 (t, J=8.4 Hz, 1H), 7.28 (dd, J$_1$=9 Hz, J$_2$=2.4 Hz, 1H), 6.70 (d, J=9.0 Hz, 1H), 6.00 (t, J=6.0 Hz, 1H), 4.82 (m, 1H), 4.66 (dd, J$_1$=17.4 Hz, J$_2$=2.4 Hz, 1H), 4.55 (m, 1H), 4.13 (dd, J$_1$=17.4 Hz, J$_2$=2.4 Hz, 1H), 4.09 (t, J=9.0 Hz, 1H), 3.81 (m, 1H), 3.77=3.71 (m, 2H), 3.63 (m, 1H), 2.98 (m, 1H), 2.90 (m, 1H), 2.26 (t, J=2.4 Hz, 1H), 2.04 (s, 3H)

LCMS: 451 (M+H$^+$) for $C_{23}H_{23}FN_6O_3$

Example 56

Preparation of Compound 56

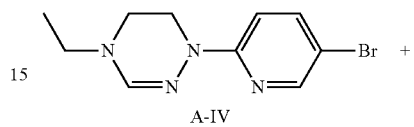

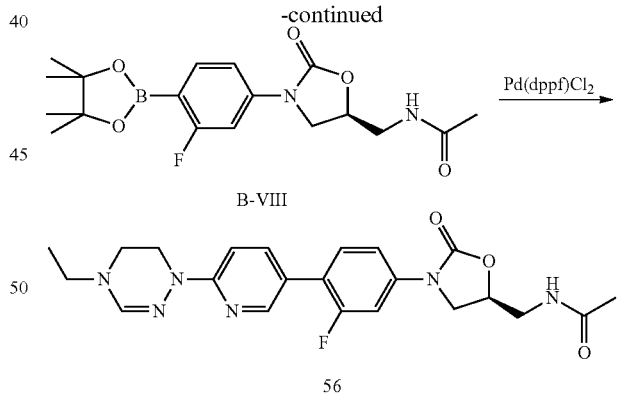

171 mg (0.63 mmol) of Compound A-IV synthesized according to Preparation Example 17 was dissolved in 4 mL of N,N-dimethylformamide, 180 mg of Compound B-VIII synthesized according to Preparation Example 37, 16 mg (0.02 mmol) of PdCl$_2$(dppf), and 0.95 mL (1.91 mmol) of a 2M aqueous sodium carbonate solution were added thereto, and the resulting solution was stirred under a nitrogen atmosphere at 85° C. for 15 hours. The reaction mixture was cooled to room temperature and filtered using celite to remove a residue. The resulting mixture was extracted with 50 mL of ethylacetate and 40 mL of saturated ammonium chloride to obtain an organic layer. The organic layer was dehydrated using anhydrous sodium sulfate, concentrated under reduced pressure, and then separated by column chromatography to obtain 19 mg (0.04 mmol) of Compound 56 as a yellow solid (yield: 7.2%).

$^1$H NMR (600 MHz, CDCl$_3$) δ 8.30 (s, 1H), 7.71 (d, J=9.0 Hz, 1H), 7.50 (d, J=12.6 Hz, 1H), 7.40 (t, J=8.4 Hz, 1H), 7.35 (d, J=8.4 Hz, 1H), 7.25 (m, 1H), 6.73 (s, 1H), 4.80 (m, 1H), 4.11~4.06 (m, 3H), 3.80 (m, 1H), 3.73 (m, 1H), 3.62 (m, 1H), 3.44 (t, J=4.8 Hz, 2H), 3.20 (q, J=7.2 Hz, 2H), 1.21 (t, J=7.2 Hz, 2H)

LCMS: 441 (M+H$^+$) for C$_{22}$H$_{25}$FN$_6$O$_3$

Example 57

Preparation of Compound 57

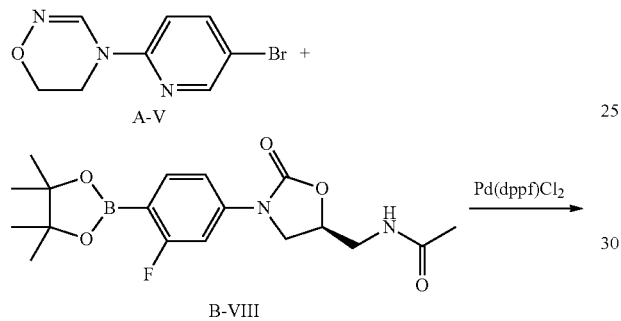

113 mg (0.27 mmol) of Compound 57 was obtained (yield: 41%) as a white solid by reacting Compound A-V and Compound B-VIII in the same manner as in Example 1.

$^1$H NMR (600 MHz, DMSO d-$_6$) δ 8.53 (s, 1H), 8.50 (s, 1H), 8.28 (t, J=5.4 Hz, 1H), 8.00 (d, J=7.8 Hz, 1H), 7.63 (m, 2H), 7.43 (d, J=9.0 Hz, 1H), 7.29 (d, J=9.0 Hz, 1H), 4.76 (m, 1H), 4.18 (t, J=9.0 Hz, 1H), 4.13 (t, J=4.8 Hz, 2H), 3.88 (t, J=4.8 Hz, 2H), 3.79 (m, 1H), 3.44 (t, J=4.8 Hz, 2H), 1.84 (s, 3H)

LCMS: 414 (M+H$^+$) for C$_{20}$H$_{20}$FN$_5$O$_4$

Example 58

Preparation of Compound 58

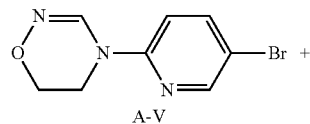

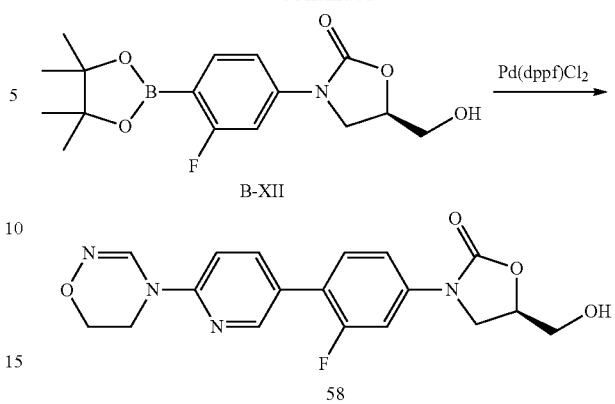

130 mg (0.35 mmol) of Compound 58 was obtained (yield: 20%) as a white solid by reacting Compound A-V and Compound B-XII in the same manner as in Example 1.

$^1$H NMR (600 MHz, DMSO d-$_6$) δ 8.52 (s, 1H), 7.99 (t, J=9.6 Hz, 1H), 7.64 (m, 2H), 7.47 (m, 2H), 7.29 (d, J=9.0 Hz, 1H), 5.28 (t, J=6.0 Hz, 1H), 4.75 (m, 1H), 4.22 (m, 1H), 4.14 (m, 3H), 3.89 (m, 2H), 3.70 (m, 1H), 3.57 (m, 1H)

LCMS: 373 (M+H$^+$) for C$_{18}$H$_{17}$FN$_4$O$_4$

Example 59

Preparation of Compound 59

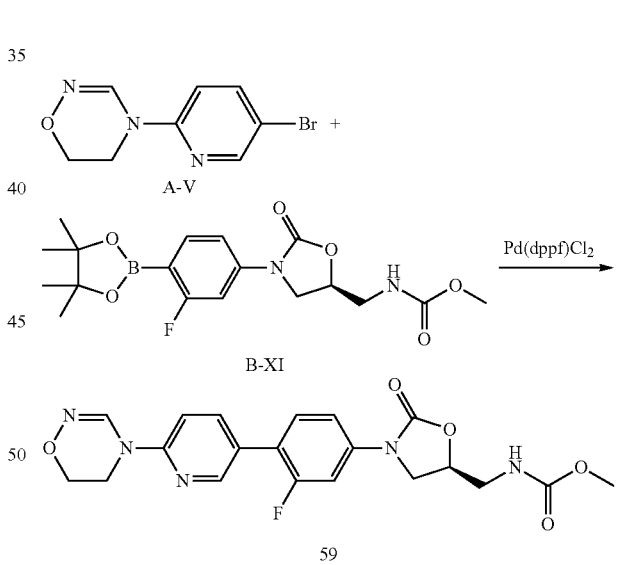

115 mg (0.27 mmol) of Compound 59 was obtained (yield: 19%) as a white solid by reacting Compound A-V and Compound B-XI in the same manner as in Example 1.

$^1$H NMR (600 MHz, DMSO d-$_6$) δ 8.52 (s, 1H), 8.50 (s, 1H), 8.00 (dd, J$_1$=9.0 Hz, J$_2$=1.8 Hz, 1H), 7.64 (t, J=9.0 Hz, 1H), 7.62 (dd, J$_1$=13.2 Hz, J$_2$=2.4 Hz, 1H), 7.55 (t, J=5.4 Hz, 1H), 7.43 (dd, J$_1$=8.4 Hz, J$_2$=1.8 Hz, 1H), 7.29 (d, J=8.4 Hz, 1H), 4.77 (m, 1H), 4.18 (t, J=9.0 Hz, 1H), 4.11 (t, J=4.2 Hz, 2H), 3.88 (m, 2H), 3.81 (m, 1H), 3.54 (s, 3H), 3.33 (m, 2H)

LCMS: 430 (M+H$^+$) for C$_{20}$H$_{20}$FN$_5$O$_5$

Example 60

Preparation of Compound 60

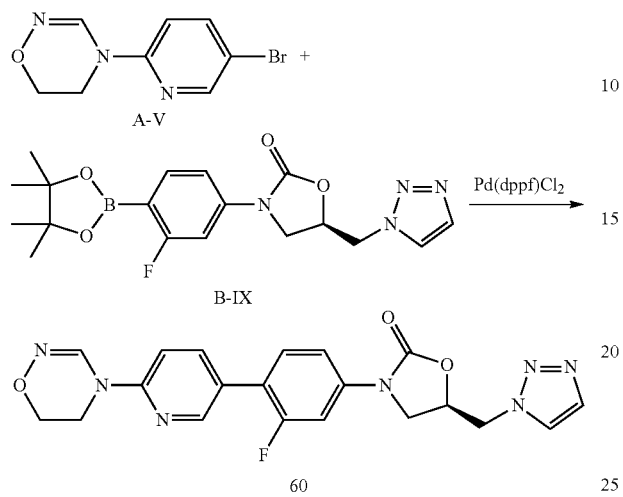

36 mg (0.08 mmol) of Compound 60 was obtained (yield: 35%) as a white solid by reacting Compound A-V and Compound B-IX in the same manner as in Example 1.

$^1$H NMR (600 MHz, DMSO d-$_6$) δ 8.52 (s, 1H), 8.49 (s, 1H), 8.19 (s, 1H), 7.99 (d, J=8.4 Hz, 1H), 7.78 (s, 1H), 7.62 (t, J=8.4 Hz, 1H), 7.55 (dd, J$_1$=13.2 Hz, J$_2$=2.4 Hz, 1H), 7.38 (dd, J$_1$=8.4 Hz, J$_2$=2.4 Hz, 1H), 7.29 (d, J=8.4 Hz, 1H), 5.18 (m, 1H), 4.86 (m, 1H), 4.29 (t, J=9.0 Hz, 1H), 4.11 (t, J=4.8 Hz, 2H), 3.95 (m, 1H), 3.88 (t, J=4.8 Hz, 2H)

LCMS: 424 (M+H$^+$) for C$_{20}$H$_{18}$FN$_7$O$_3$

Example 61

Preparation of Compound 61

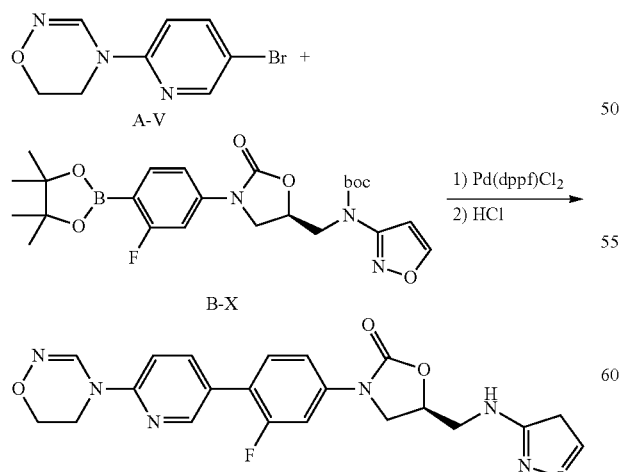

81 mg (0.18 mmol) of Compound 61 was obtained (yield: 75%) as a white solid by reacting Compound A-V and Compound B-X in the same manner as in Examples 1 and 2.

$^1$H NMR (600 MHz, DMSO) δ 8.55 (s, 1H), 8.50 (s, 1H), 8.39 (d, J=1.8 Hz, 1H), 8.00 (d, J=10.2 Hz, 1H), 7.63 (m, 2H), 7.44 (dd, J$_1$=9.0 Hz, J$_2$=2.4 Hz, 1H), 7.29 (d, J=8.4 Hz, 1H), 6.01 (d, J=1.8 Hz, 1H), 4.92 (m, 1H), 4.21 (dd, J$_1$=8.4 Hz, J$_2$=8.4 Hz, 1H), 4.12 (t, J=7.2 Hz, 2H), 3.88 (m, 3H), 3.47 (m, 2H)

LCMS: 439 (M+H$^+$) for C$_{21}$H$_{19}$FN$_6$O$_4$

Example 62

Preparation of Compound 62

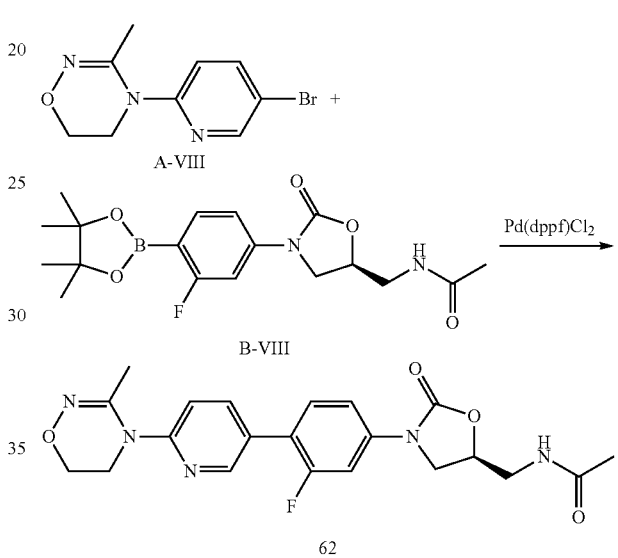

30 mg (0.07 mmol) of Compound 62 was obtained (yield: 68%) as a white solid by reacting Compound A-VIII and Compound B-VIII in the same manner as in Example 1.

$^1$H NMR (600 MHz, CDCl$_3$) δ 8.72 (m, 1H), 7.88 (dd, J$_1$=8.4 Hz, J$_2$=3.6 Hz, 1H), 7.59 (dd, J$_1$=12.6 Hz, J$_2$=2.4 Hz, 1H), 7.44 (dd, J$_1$=8.4 Hz, J$_2$=8.4 Hz, 1H), 7.33 (dd, J$_1$=8.4 Hz, J$_2$=2.4 Hz, 1H), 7.08 (d, J=8.4 Hz, 1H), 6.12 (t, J=6 Hz, 1H), 4.83 (m, 1H), 4.21 (t, J=4.8 Hz, 2H), 4.10 (dd, J=9.0 Hz, 1H), 3.93 (t, J=3.6 Hz, 2H), 3.85 (dd, J=6.6 Hz, 1H), 3.75~3.65 (m, J=6.6 Hz, 2H)

LCMS: 428 (M+H$^+$) for C$_{21}$H$_{22}$FN$_5$O$_4$

Example 63

Preparation of Compound 63

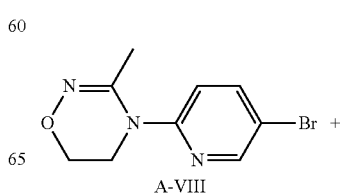

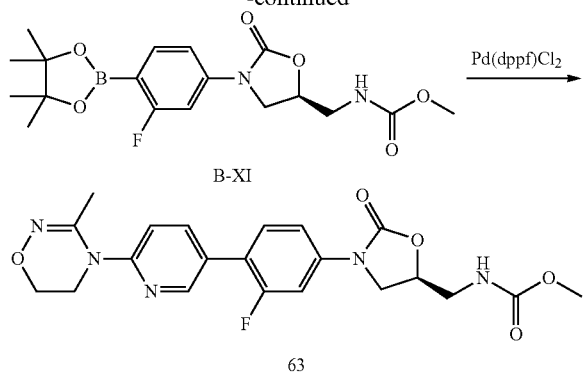

326 mg (0.73 mmol) of Compound 63 was obtained (yield: 51%) as a white solid by reacting Compound A-VIII and Compound B-XI in the same manner as in Example 1.

$^1$H NMR (600 MHz, DMSO d-$_6$) δ 8.55 (s, 1H), 7.86 (m, 1H), 7.56 (dd, $J_1$=12.6 Hz, $J_2$=1.8 Hz, 1H), 7.43 (t, J=8.4 Hz, 1H), 7.33 (dd, $J_1$=8.4 Hz, $J_2$=1.8 Hz, 1H), 7.05 (d, J=8.4 Hz, 1H), 5.13 (m, 1H), 4.79 (m, 1H), 4.18 (t, J=4.8 Hz, 2H), 4.08 (t, J=9.0 Hz, 1H), 3.90 (t, J=4.8 Hz, 2H), 3.85 (t, J=7.8 Hz, 1H), 3.67 (s, 3H), 3.63 (m, 1H), 3.55 (m, 1H), 2.10 (s, 3H)

LCMS: 444 (M+H$^+$) for $C_{21}H_{22}FN_5O_5$

Example 64

Preparation of Compound 64

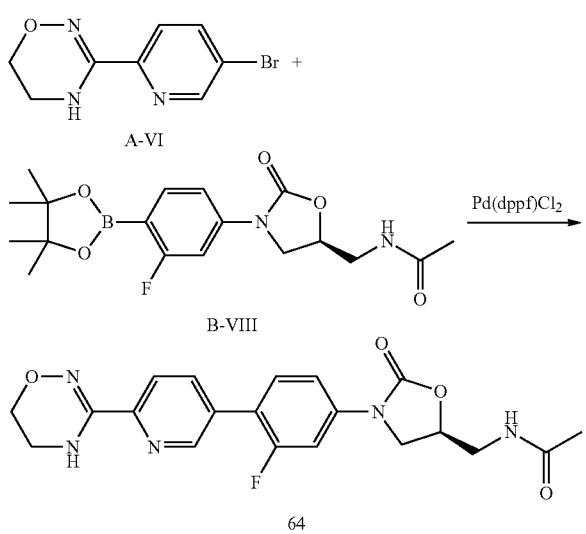

168 mg (0.41 mmol) of Compound 64 was obtained (yield: 56%) as a white solid by reacting Compound A-VI and Compound B-VIII in the same manner as in Example 1.

$^1$H NMR (600 MHz, DMSO d-$_6$) δ 8.77 (s, 1H), 8.27 (t, J=6.0 Hz, 1H), 8.04 (dd, $J_1$=7.2 Hz, $J_2$=1.8 Hz, 1H), 7.96 (d, J=9.0 Hz, 1H), 7.71 (t, J=8.4 Hz, 1H), 7.66 (dd, $J_1$=13.2 Hz, $J_2$=2.4 Hz, 1H), 7.47 (dd, $J_1$=8.4 Hz, $J_2$=2.4 Hz, 1H), 7.40 (t, J=3.6 Hz, 1H), 4.78 (m, 1H), 4.19 (t, J=8.4 Hz, 1H), 3.88 (t, J=4.8 Hz, 2H), 3.80 (dd, $J_1$=9.0 Hz, $J_2$=6.0 Hz, 1H), 3.47 (dd, $J_1$=8.4 Hz, $J_2$=3.6 Hz, 2H), 3.44 (t, J=4.8 Hz, 2H), 1.84 (s, 3H)

LCMS: 414 (M+H$^+$) for $C_{20}H_{20}FN_5O_4$

Example 65

Preparation of Compound 65

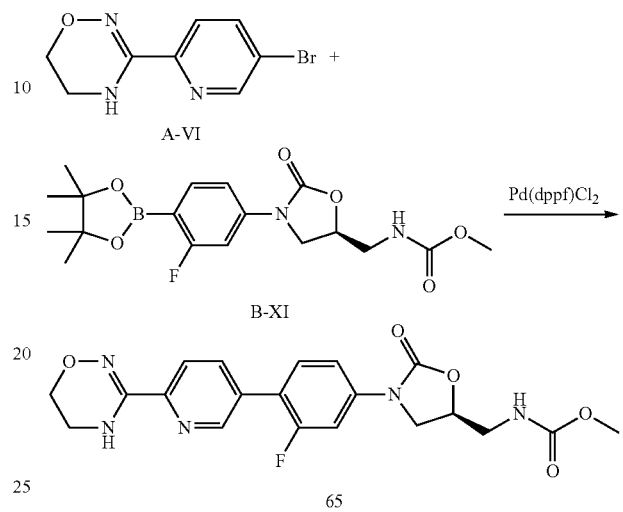

391 mg (0.91 mmol) of Compound 65 was obtained (yield: 78%) as a white solid by reacting Compound A-VI and Compound B-XI in the same manner as in Example 1.

$^1$H NMR (400 MHz, DMSO d-$_6$) δ 8.77 (s, 1H), 8.05 (d, J=8.4 Hz, 1H), 7.96 (d, J=8.0 Hz, 1H), 7.72 (t, J=8.8 Hz, 1H), 7.66 (dd, $J_1$=13.6 Hz, $J_2$=2.0 Hz, 1H), 7.56 (t, J=5.6 Hz, 1H), 7.47 (dd, $J_1$=8.4 Hz, $J_2$=2.0 Hz, 1H), 7.40 (m, 1H), 4.78 (m, 1H), 4.19 (t, J=9.0 Hz, 1H), 3.88 (t, J=4.6 Hz, 2H), 3.84 (dd, $J_1$=8.8 Hz, $J_2$=6.0 Hz, 1H), 3.55 (s, 3H), 3.48 (m, 4H)

LCMS: 430 (M+H$^+$) for $C_{20}H_{20}FN_5O_5$

Example 66

Preparation of Compound 66

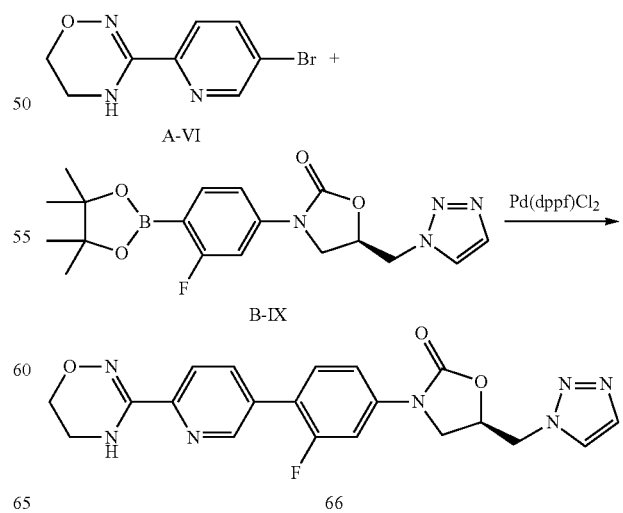

78 mg (0.18 mmol) of Compound 66 was obtained (yield: 75%) as a pale pink solid by reacting Compound A-VI and Compound B-IX in the same manner as in Example 1.

$^1$H NMR (600 MHz, DMSO d-$_6$) δ 8.77 (s, 1H), 8.19 (s, 1H), 8.04 (d, J=8.4 Hz, 1H), 7.95 (d, J=8.4 Hz, 1H), 7.78 (s, 1H), 7.70 (t, J=9.0 Hz, 1H), 7.60 (dd, J$_1$=13.8 Hz, J$_2$=2.4 Hz, 1H), 7.42 (dd, J$_1$=8.4 Hz, J$_2$=2.4 Hz, 1H), 7.40 (t, J=2.4 Hz, 1H), 5.19 (m, 1H), 4.87 (m, 1H), 4.31 (t, J=9.0 Hz, 1H), 3.97 (m, 1H), 3.88 (t, J=4.8 Hz, 2H), 3.47 (m, 2H)

LCMS: 424 (M+H$^+$) for C$_{20}$H$_{18}$FN$_7$O$_3$

Example 67

Preparation of Compound 67

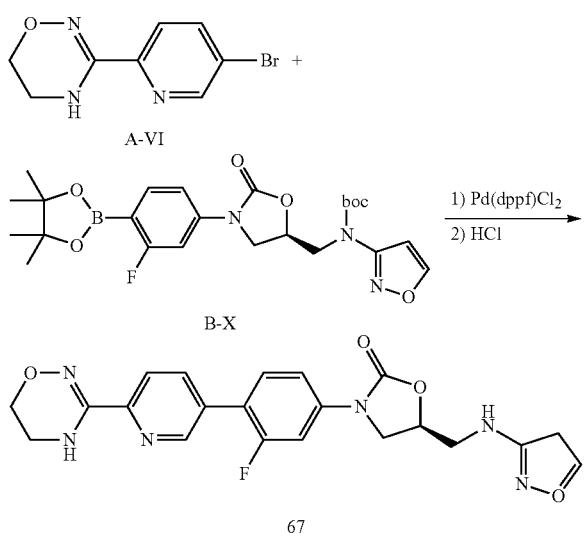

88 mg (0.20 mmol) of Compound 67 was obtained (yield: 68%) as a pale yellow solid by reacting Compound A-VI and Compound B-X in the same manner as in Examples 1 and 2.

$^1$H NMR (600 MHz, DMSO) δ 9.08 (s, 1H), 8.89 (s, 1H), 8.40 (d, J=1.8 Hz, 1H), 8.20 (dd, J$_1$=8.4 Hz, J$_2$=1.2 Hz, 1H), 8.13 (d, J=8.4 Hz, 1H), 7.75 (dd, J$_1$=8.4 Hz, J$_2$=8.4 Hz, 1H), 7.69 (dd, J$_1$=13.8 Hz, J$_2$=2.4 Hz, 1H), 7.50 (dd, J$_1$=8.4 Hz, J$_2$=1.8 Hz, 1H), 6.01 (d, J=1.8 Hz, 1H), 4.94 (m, 1H), 4.23 (dd, J$_1$=9.0 Hz, J$_2$=9.0 Hz, 1H), 4.13 (t, J=4.2 Hz, 2H), 3.90 (dd, J$_1$=9.0 Hz, J$_2$=6.6 Hz, 1H), 3.60 (t, J=4.2 Hz, 2H), 3.47 (m, 2H)

LCMS: 439 (M+H$^+$) for C$_{21}$H$_{19}$FN$_6$O$_4$

Example 68

Preparation of Compound 68

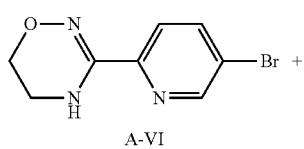

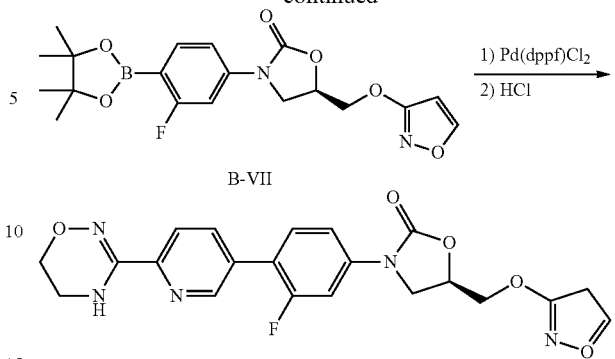

111 mg (0.25 mmol) of Compound 68 was obtained (yield: 62%) as a white solid by reacting Compound A-VI and Compound B-VII in the same manner as in Example 1.

$^1$H NMR (600 MHz, DMSO d-$_6$) δ 8.78 (s, 1H), 8.72 (d, J=1.8 Hz, 1H), 8.05 (d, J=8.4 Hz, 1H), 7.74 (d, J=8.4 Hz, 1H), 7.70 (dd, J$_1$=15.6 Hz, J$_2$=2.4 Hz, 1H), 7.52 (dd, J$_1$=9.0 Hz, J$_2$=2.4 Hz, 1H), 7.43 (m, 1H), 6.42 (d, J=1.8 Hz, 1H), 5.14 (m, 1H), 4.50 (m, 2H), 4.27 (t, J=9.0 Hz, 1H), 4.00 (dd, J$_1$=9.6 Hz, J$_2$=6.0 Hz, 1H), 3.88 (t, J=4.8 Hz, 2H), 3.47 (m, 2H)

LCMS: 441 (M+H$^+$) for C$_{21}$H$_{19}$FN$_5$O$_5$

Example 69

Preparation of Compound 69

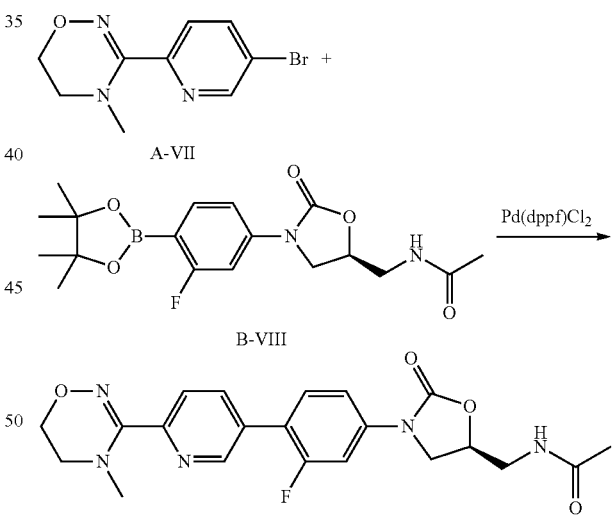

120 mg (0.28 mmol) of Compound 69 was obtained (yield: 53%) as a white solid by reacting Compound A-WI and Compound B-VIII in the same manner as in Example 1.

$^1$H NMR (600 MHz, CDCl$_3$) δ 8.80 (s, 1H), 7.93 (d, J=8.4 Hz, 1H), 7.72 (d, J=7.8 Hz, 1H), 7.61 (dd, J$_1$=12.6 Hz, J$_2$=2.4 Hz, 1H), 7.47 (t, J=9.0 Hz, 1H), 7.33 (dd, J$_1$=9.0 Hz, J$_2$=2.4 Hz, 1H), 6.03 (m, 1H), 4.83 (m, 1H), 4.18 (t, J=9.0 Hz, 1H), 4.10 (t, J=9.0 Hz, 1H), 3.84 (dd, J$_1$=8.4 Hz, J$_2$=6.6 Hz, 1H), 3.74 (m, 1H), 3.68 (m, 3H), 3.52 (t, J=4.8 Hz, 2H), 2.94 (s, 3H), 2.04 (s, 3H)

LCMS: 428 (M+H$^+$) for C$_{21}$H$_{22}$FN$_5$O$_4$

Example 70

Preparation of Compound 70

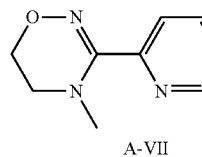

A-VII

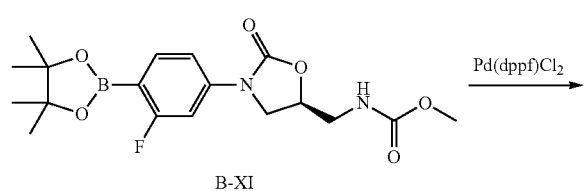

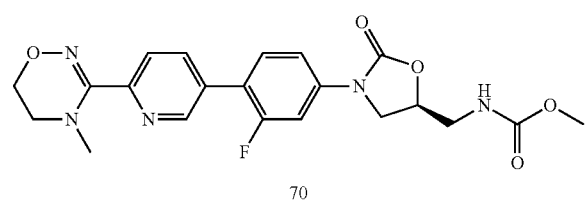

70

437 mg (0.98 mmol) of Compound 70 was obtained (yield: 84%) as a white solid by reacting Compound A-VII and Compound B-XI in the same manner as in Example 1.

$^1$H NMR (600 MHz, CDCl$_3$) δ 8.81 (s, 1H), 7.93 (d, J=7.8 Hz, 1H), 7.72 (d, J=7.8 Hz, 1H), 7.60 (dd, J$_1$=13.2 Hz, J$_2$=1.8 Hz, 1H), 7.47 (t, J=8.4 Hz, 1H), 7.35 (dd, J$_1$=9.0 Hz, J$_2$=2.4 Hz, 1H), 5.13 (m, 1H), 4.82 (m, 1H), 4.17 (t, J=4.8 Hz, 2H), 4.11 (t, J=9.0 Hz, 1H), 3.87 (t, J=7.8 Hz, 1H), 3.70 (s, 3H), 3.65 (m, 1H), 3.60 (m, 1H), 3.51 (t, J=7.8 Hz, 2H), 2.94 (s, 3H)

LCMS: 444 (M+H$^+$) for C$_{21}$H$_{22}$FN$_5$O$_5$

Example 71

Preparation of Compound 71

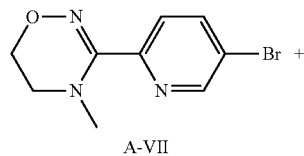

A-VII

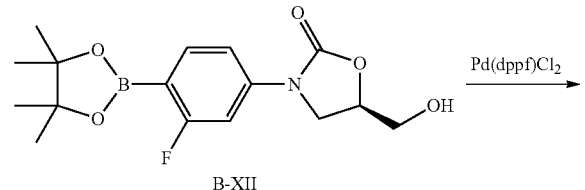

B-XII

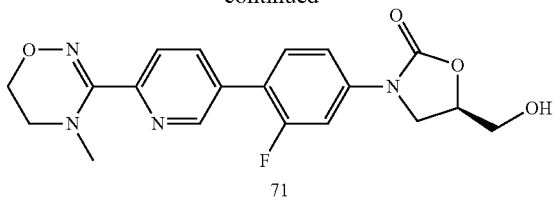

71

71 mg (0.16 mmol) of Compound 71 was obtained (yield: 20%) as a white solid by reacting Compound A-VII and Compound B-XII in the same manner as in Example 1.

$^1$H NMR (400 MHz, DMSO d-$_6$) δ 8.82 (s, 1H), 8.06 (d, J=8.4 Hz, 1H), 7.69 (m, 1H), 7.63 (d, J=8.4 Hz, 1H), 7.51 (m, 2H), 5.27 (t, J=6.0 Hz, 1H), 4.76 (m 1H), 4.15 (t, J=9.2 Hz, 1H), 4.00 (t, J=4.8 Hz, 2H), 3.90 (dd, J$_1$=8.8 Hz, J$_2$=6.1 Hz, 1H), 3.70 (m, 1H), 3.59 (m, 1H), 3.42 (t, J=4.4 Hz, 2H), 2.80 (s, 1H)

LCMS: 444 (M+H$^+$) for C$_{19}$H$_{19}$FN$_4$O$_4$

Experimental Example 1

Measurement of In Vitro Antibacterial Activity

To evaluate antibacterial activities of the oxazolidinone derivatives synthesized according to Examples 1 to 71, an in vitro activity test was performed using the following method.

The in vitro antibacterial activities of the oxazolidinone derivatives of Examples 1 to 71 were evaluated by measuring 90% minimum inhibitory concentration (MIC$_{90}$, μg/mL) which is a minimum concentration of an antibiotic that inhibits the growth of bacteria up to 90%, as compared with bacterial growth in a non-treated control which was measured by photospectroscopy. MIC$_{90}$ was measured by broth microdilution method based on CLSI standards [reference: Clinical and Laboratory Standards Institute Document. (2000) Methods for Dilution Antimicrobial Susceptibility Test for Bacteria that Grow Aerobically-Fifth Edition: M7-A5. CLSI, Villanova, Pa.].

1) Test Strains

Activities of 12 strains including *Staphylococcus aureus*, Methicillin Resistant *Staphylococcus aureus*, *Staphylococcus epidermidis*, Methicillin Resistant *Staphylococcus epidermidis*, *Enterococcus faecalis*, Vancomycin Resistant *Enterococcus faecalis*, Linezolid and Vancomycin Resistant *Enterococcus faecalis*, *Enterococcus faecium*, Vancomycin Resistant *Enterococcus faecium*, Linezolid and Vancomycin Resistant *Enterococcus faecium*, and *Moraxella catarrhalis*, were measured, and results are shown in Table 1 below.

2) Preparation Method of Test Material 10240 ug/mL of test materials (i.e., the oxazolidinone derivatives of Examples 1 to 71) were each dissolved in DMSO, and each resulting solution was subjected to two-fold serial dilution and then diluted 20-fold with sterile triple distilled water. The final concentration of test material in the antibacterial test was from 0.063 μg/mL (minimum) to 128 μg/mL (maximum), and the final concentration of DMSO used as an excipient was 2.5% (V/V). Linezolid represented by Formula B below (manufactured by Pfizer) was used as a control and bacterial activity thereof was compared with those of the test materials. Results are shown in Table 1 below.

[Formula B]

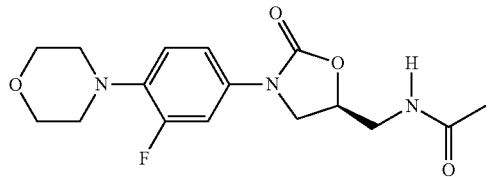

TABLE 1

Antibacterial Activities of Compounds of Formula 1 (MIC$_{90}$, ug/mL)

| Strains used | LZD | 1 | 2 | 3 | 4 | 5 | 6 | 7 | 8 | 9 | 10 | 11 | 12 | 13 | 16 | 17 | 19 | 20 | 21 | 24 | 25 | 26 | 27 | 29 | 30 | 31 | 32 | 33 | 34 | 37 | 38 | 39 | 40 | 41 | 42 | 43 | 44 | 45 | 46 | 48 | 50 | 51 | 52 | 53 | 54 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1 S. aureus | 1 | 0.5 | 0.5 | 0.063 | 0.5 | 0.5 | 0.5 | 0.5 | 0.25 | 1 | 1 | 0.063 | 0.125 | 1 | 0.25 | 0.125 | 0.25 | 2 | 0.25 | 0.5 | 0.063 | 0.25 | 0.5 | 8 | 0.25 | 0.25 | 0.25 | 0.25 | 0.25 | 0.5 | 0.125 | 0.25 | 0.25 | 0.25 | 0.25 | 0.25 | 0.5 | 0.5 | 0.25 | 0.5 | 0.5 | 0.5 | 0.25 | 1 | 0.25 |
| 2 S. aureus$^{MR}$ | 2 | 1 | 1 | 0.5 | 1 | 1 | 1 | 1 | 1 | 4 | 2 | 0.25 | 0.25 | 2 | 1 | 0.5 | 0.5 | 8 | 1 | 1 | 0.5 | 1 | 2 | 8 | 1 | 1 | 1 | 1 | 0.5 | 1 | 0.5 | 0.5 | 0.25 | 0.25 | 0.5 | 0.5 | 1 | 1 | 0.5 | 1 | 1 | 1 | 0.5 | 2 | 0.5 |
| 3 S. epidermidis | 1 | 0.25 | 0.5 | 0.125 | 0.5 | 0.5 | 0.5 | 0.5 | 0.5 | 1 | 1 | 0.063 | 0.125 | 1 | 0.25 | 0.25 | 0.25 | 4 | 0.5 | 0.5 | 0.25 | 0.5 | 1 | 4 | 0.5 | 0.25 | 0.25 | 0.25 | 0.5 | 1 | 0.5 | 1 | 0.5 | 0.5 | 0.5 | 1 | 1 | 1 | 0.5 | 1 | 1 | 1 | 0.25 | 1 | 0.125 |
| 4 S. epidermidis$^{MR}$ | 2 | 1 | 1 | 0.5 | 1 | 1 | 1 | 1 | 1 | 4 | 2 | 0.25 | 0.25 | 2 | 1 | 0.5 | 0.5 | 4 | 1 | 2 | 1 | 1 | 2 | 8 | 2 | 1 | 1 | 1 | 1 | 2 | 0.5 | 2 | 2 | 2 | 2 | 2 | 4 | 4 | 32 | 4 | 4 | 4 | 0.5 | 2 | 0.5 |
| 5 E. faecalis | 2 | 0.5 | 0.5 | 0.25 | 0.5 | 0.5 | 0.5 | 0.5 | 0.5 | 1 | 1 | 0.125 | 0.125 | 1 | 0.25 | 0.25 | 0.5 | 2 | 1 | 1 | 0.5 | 0.5 | 0.5 | 16 | 0.5 | 0.5 | 0.5 | 0.25 | 0.5 | 1 | 0.25 | 0.5 | 0.5 | 0.5 | 0.5 | 0.5 | 4 | 2 | 2 | 4 | 2 | 4 | 0.5 | 1 | 0.063 |
| 6 E. faecalis$^{VanA}$ | 2 | 0.5 | 0.5 | 0.125 | 0.5 | 0.5 | 0.5 | 1 | 1 | 2 | 2 | 0.125 | 0.25 | 1 | 0.5 | 0.25 | 0.5 | 2 | 1 | 1 | 0.5 | 0.5 | 0.5 | 16 | 1 | 0.5 | 0.5 | 0.25 | 0.5 | 1 | 0.5 | 1 | 1 | 1 | 1 | 1 | 4 | 4 | 4 | 4 | 4 | 4 | 0.5 | 1 | 0.063 |
| 7 E. faecalis$^{VanA}$ LR | 32 | 2 | 2 | 0.5 | 2 | 2 | 2 | 4 | 4 | 8 | 8 | 0.5 | 1 | 2 | 1 | 1 | 2 | 8 | 2 | 4 | 4 | 4 | 4 | 64 | 4 | 2 | 2 | 2 | 2 | 8 | 4 | 4 | 2 | 2 | 2 | 2 | | | | | | | | | |
| 8 E. faecium | 1 | 0.5 | 0.5 | 0.063 | 0.5 | 0.5 | 0.5 | 1 | 1 | 2 | 1 | 0.063 | 0.063 | 2 | 0.5 | 0.25 | 0.25 | 2 | 0.5 | 0.5 | 0.25 | 0.25 | 0.25 | 8 | 0.25 | 0.25 | 0.25 | 0.125 | 0.25 | 1 | 0.25 | 0.25 | 0.125 | 0.125 | 0.125 | 0.25 | | | | | | | | | |
| 9 E. faecium$^{VanA}$ | 2 | 0.5 | 0.5 | 0.125 | 0.5 | 0.5 | 0.5 | 1 | 0.5 | 2 | 2 | 0.125 | 0.25 | 1 | 0.5 | 0.25 | 0.5 | 2 | 0.5 | 0.5 | 0.5 | 0.5 | 0.5 | 8 | 0.5 | 0.25 | 0.5 | 0.25 | 0.5 | 1 | 0.5 | 1 | 0.5 | 0.5 | 0.5 | 0.5 | | | | | | | | | |
| 10 E. faecium$^{VanA}$LR | 32 | 2 | 2 | 0.5 | 2 | 2 | 2 | 4 | 4 | 8 | 8 | 0.5 | 1 | 2 | 2 | 2 | 2 | 8 | 2 | 4 | 4 | 4 | 2 | 64 | 4 | 1 | 2 | 2 | 2 | 8 | 4 | 4 | 4 | 4 | 4 | 4 | | | | | | | | | |
| 11 E. faecium$^{VanA}$LR | 64 | 2 | 2 | 0.5 | 2 | 2 | 2 | 4 | 4 | 8 | 8 | 1 | 1 | 2 | 2 | 2 | 2 | 8 | 4 | 8 | 2 | 2 | 2 | 64 | 2 | 2 | 2 | 2 | 4 | 8 | 4 | 4 | 4 | 4 | 4 | 4 | | | | | | | | | |
| 12 M. catarrhalis | 8 | 2 | 4 | 0.25 | 2 | N/A | N/A | 2 | 2 | N/A | N/A | 1 | 0.5 | 2 | 2 | 2 | 1 | 8 | 4 | 4 | 4 | 4 | 4 | 32 | 4 | 2 | 2 | 2 | 2 | 8 | 2 | 2 | 2 | 2 | 2 | 2 | | | | | | | | | |

TABLE 1-continued

Antibacterial Activities of Compounds of Formula 1 (MIC$_{90}$, ug/mL)

| | | | | | | | | | | |
|---|---|---|---|---|---|---|---|---|---|---|
| 7 | E. faecalis$^{VanA}$ LR | 16 | >128 | 128 | 32 | 16 | 16 | 1 | 4 | 0.5 |
| 8 | E. faecium | 1 | 0.5 | 0.5 | 1 | 0.5 | 1 | 0.5 | 1 | 0.25 |
| 9 | E. faecium$^{VanA}$ | 2 | 2 | 2 | 2 | 2 | 4 | 0.5 | 1 | 0.063 |
| 10 | E. faecium$^{VanA}$LR | 16 | >128 | 128 | 16 | 16 | 32 | 1 | 4 | 0.5 |
| 11 | E. faecium$^{VanA}$LR | 16 | >128 | >128 | 32 | 32 | 32 | 1 | 4 | 0.5 |
| 12 | M. catarrhalis | >128 | >128 | >128 | 32 | >128 | >128 | 4 | 4 | 1 |

| | Strains used | Oxazolidinone derivatives of the present invention | | | | | | | | |
|---|---|---|---|---|---|---|---|---|---|---|
| | | 55 | 56 | 57 | 58 | 59 | 60 | 61 | 62 | 63 |
| 1 | S. aureus | 1 | 1 | 0.25 | 0.5 | 0.25 | 0.125 | 0.063 | 0.5 | 2 |
| 2 | S. aureus$^{MR}$ | 4 | 4 | 0.5 | 1 | 0.5 | 0.25 | 0.25 | 2 | 2 |
| 3 | S. epidermidis | 2 | 1 | 0.25 | 0.5 | 0.25 | 0.25 | 0.25 | 0.5 | 1 |
| 4 | S. epidermidis$^{MR}$ | 4 | 2 | 0.5 | 1 | 1 | 0.25 | 0.5 | 4 | 4 |
| 5 | E. faecalis | 1 | 1 | 0.25 | 1 | 0.5 | 0.25 | 0.5 | 1 | 2 |
| 6 | E. faecalis$^{VanA}$ | 2 | 2 | 0.25 | 0.5 | 0.5 | 0.25 | 0.5 | 1 | 2 |
| 7 | E. faecalis$^{VanA}$ LR | 4 | 4 | 1 | 8 | 4 | 1 | 2 | 4 | 16 |
| 8 | E. faecium | 2 | 1 | 0.125 | 0.5 | 0.25 | 0.125 | 0.25 | 0.5 | 1 |
| 9 | E. faecium$^{VanA}$ | 2 | 1 | 0.125 | 1 | 0.25 | 0.125 | 0.5 | 1 | 2 |
| 10 | E. faecium$^{VanA}$LR | 4 | 4 | 1 | 4 | 4 | 1 | 2 | 8 | 16 |
| 11 | E. faecium$^{VanA}$LR | 4 | 4 | 2 | 8 | 4 | 2 | 2 | 4 | 16 |
| 12 | M. catarrhalis | N/A | 2 | 2 | 8 | 2 | 1 | 2 | 4 | 8 |

| | Strains used | Oxazolidinone derivatives of the present invention | | | | | | | |
|---|---|---|---|---|---|---|---|---|---|
| | | 64 | 65 | 66 | 67 | 68 | 69 | 70 | 71 |
| 1 | S. aureus | 0.25 | 0.5 | 0.125 | 0.25 | 0.5 | 0.5 | 1 | 2 |
| 2 | S. aureus$^{MR}$ | 0.5 | 0.5 | 0.5 | 0.5 | 1 | 2 | 2 | 4 |
| 3 | S. epidermidis | 0.25 | 0.5 | 0.25 | 0.25 | 1 | 0.5 | 1 | 2 |
| 4 | S. epidermidis$^{MR}$ | 0.5 | 1 | 0.5 | 0.5 | 2 | 2 | 4 | 4 |
| 5 | E. faecalis | 0.25 | 0.5 | 0.25 | 0.5 | 1 | 1 | 2 | 4 |
| 6 | E. faecalis$^{VanA}$ | 0.25 | 0.5 | 0.25 | 0.5 | 2 | 1 | 2 | 2 |
| 7 | E. faecalis$^{VanA}$ LR | 1 | 4 | 1 | 2 | >128 | 2 | 8 | 16 |
| 8 | E. faecium | 0.25 | 0.5 | 0.125 | 0.25 | 0.25 | 1 | 1 | 2 |
| 9 | E. faecium$^{VanA}$ | 0.25 | 0.5 | 0.25 | 0.5 | 1 | 1 | 1 | 2 |
| 10 | E. faecium$^{VanA}$LR | 1 | 4 | 1 | 2 | >128 | 4 | 8 | 8 |
| 11 | E. faecium$^{VanA}$LR | 2 | 4 | 2 | 2 | >128 | 4 | 8 | 16 |
| 12 | M. catarrhalis | 2 | 2 | 1 | 1 | >128 | 8 | 4 | 8 |

1. *Staphylococcus aureus*
2. Methicillin Resistant *Staphylococcus aureus*
3. *Staphylococcus epidermidis*
4. Methicillin Resistant *Staphylococcus epidermidis*
5. *Enterococcus faecalis*
6. Vancomycin Resistant *Enterococcus faecalis*
7. Linezolid and Vancomycin Resistant *Enterococcus faecalis*
8. *Enterococcus faecium*
9. Vancomycin Resistant *Enterococcus faecium*
10, 11. Linezolid and Vancomycin Resistant *Enterococcus faecium*
12. *Moraxella catarrhalis*

As shown in Table 1, it can be confirmed that the oxazolidinone derivatives of the present invention were more effective against Gram-positive bacteria (e.g., MRSA, VRE, and the like) resistant to existing antibiotics at much lower concentration when compared to linezolid as a control and, in particular, the oxazolidinone derivatives were very effective against linezolid-resistant bacteria. In particular, Compounds 3, 11 and 54 have very high antibacterial activity against *Enterococcus faecalis* and *Enterococcus faecium* which are resistant to linezolid, which indicates that the compounds may be effectively used against linezolid-resistant bacteria that have recently emerged and may cause major problems in future.

Therefore, the oxazolidinone derivatives of the present invention may be effectively used as antibiotics having broad spectrum against Gram-positive bacteria and as therapeutic agents to treat infection with resistant strains such as MRSA and VRE, in particular linezolid-resistant bacteria.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the novel oxazolidinone derivatives of the present invention have a broad antibacterial spectrum against resistant bacteria including MRSA and VRE. In particular, the oxazolidinone derivatives have high activity against linezolid-resistant bacteria and thus may be effectively used as second-generation oxazolidinone-based antibiotics. In addition, the compounds of the present invention have a cyclic amidoxime or cyclic amidrazone group and thus can form a salt. Accordingly, the compounds have higher solubility with respect to water than existing compounds and thus the compounds may be easily developed as an oral formulation or an injection.

The invention claimed is:

1. An oxazolidinone derivative represented by Formula 1 below, a prodrug thereof, a hydrate thereof, a solvate thereof, an isomer thereof, or a pharmaceutically acceptable salt thereof:

(1)

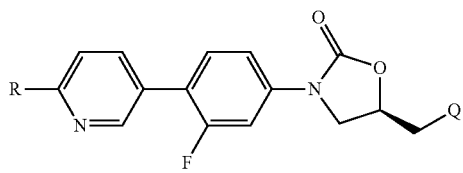

wherein R is a heterocyclic group selected from the following groups:

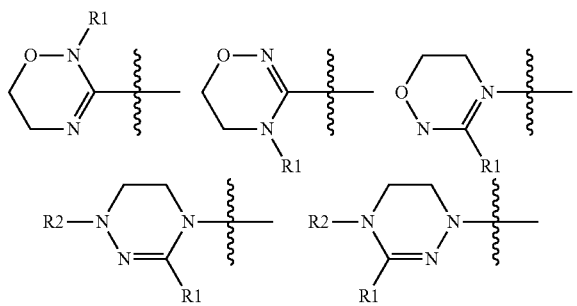

$R_1$ is hydrogen, $C_1$-$C_6$ alkyl, or $C_3$-$C_6$ cycloalkyl;
$R_2$ is hydrogen, $C_1$-$C_6$ alkyl, or $(CH_2)_m C(=O)R_{21}$, wherein $R_{21}$ is hydrogen, $(CH_2)_n NHR_{211}$, wherein $R_{211}$ is hydrogen or $C_1$-$C_6$ alkyl, $CH_2OH$, or $CH(OH)CH_2OH$ and m and n are each independently an integer of 0 to 3; and
Q is $OR_3$, $NHR_3$, or

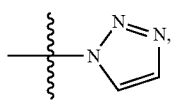

wherein $R_3$ is hydrogen, $C_1$-$C_6$ alkyl, —$C(=O)R_{31}$, wherein $R_{31}$ is hydrogen, $C_1$-$C_6$ alkyl, $C_3$-$C_6$ cycloalkyl, or $O$—($C_1$-$C_6$) alkyl, or a hetero aromatic ring group selected from the following groups;

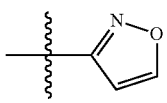 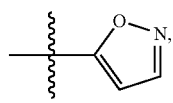

wherein the prodrug is an in vivo hydrolysable ester of the oxazolidinone derivative.

2. The oxazolidinone derivative, the prodrug thereof, the hydrate thereof, the solvate thereof, the isomer thereof, or the pharmaceutically acceptable salt thereof according to claim 1, wherein the oxazolidinone derivative is represented by one selected from Formulas 2 to 4 below:

(2)

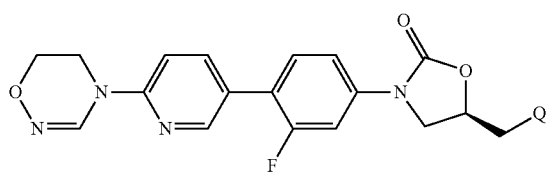

(3)

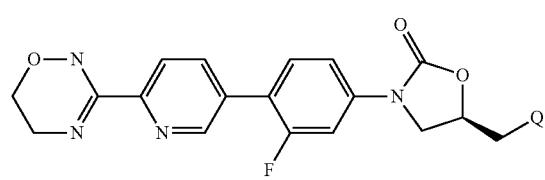

(4)

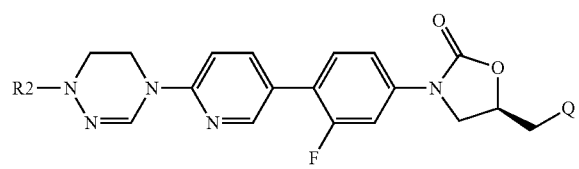

wherein $R_2$ and Q are the same as defined in claim 1.

3. The oxazolidinone derivative, the prodrug thereof, the hydrate thereof, the solvate thereof, the isomer thereof, or the pharmaceutically acceptable salt thereof according to claim 2, wherein Q is $NHC(=O)CH_3$, $NHC(=O)OCH_3$,

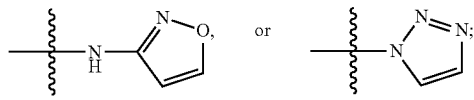 [SMILES: *Nc1ccon1 ; *n1ccnn1]

and $R_2$ is methyl, $C(=O)CH_2OH$, $C(=O)CH_2NH_2$, or $C(=O)CH(OH)CH_2OH$.

4. The oxazolidinone derivative, the prodrug thereof, the hydrate thereof, the solvate thereof, the isomer thereof, or the pharmaceutically acceptable salt thereof according to claim 2, wherein the oxazolidinone derivative is represented by one selected from Formulas 5 to 7 below:

(5)

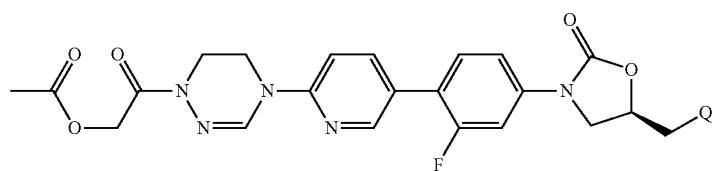

-continued (6)

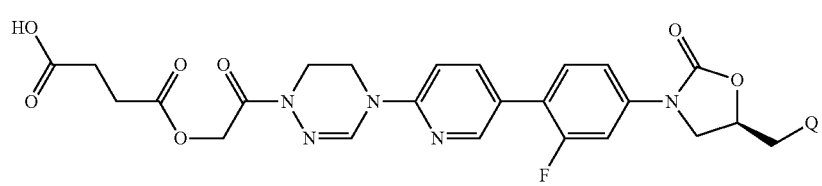

(7)

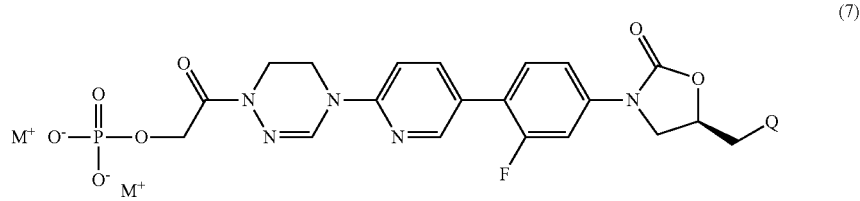

wherein Q is the same as defined in claims 1; and M⁺ is an alkali metal such as Na⁺ or K⁺ or an ammonium ion.

5. The oxazolidinone derivative, the prodrug thereof, the hydrate thereof, the solvate thereof, the isomer thereof, or the pharmaceutically acceptable salt thereof according to claim 1, wherein the oxazolidinone derivative is one selected from the following compounds:

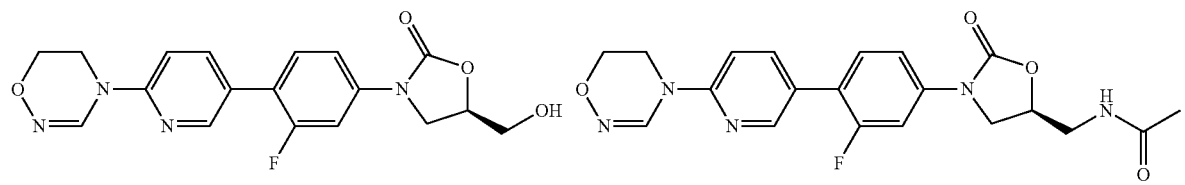

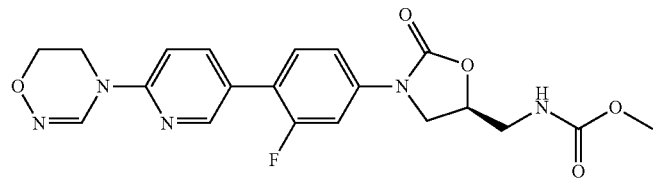

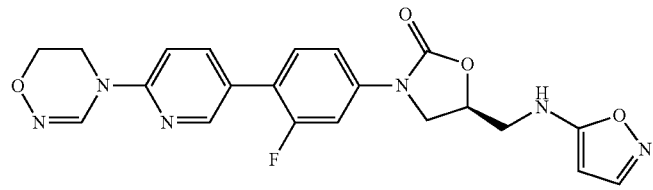

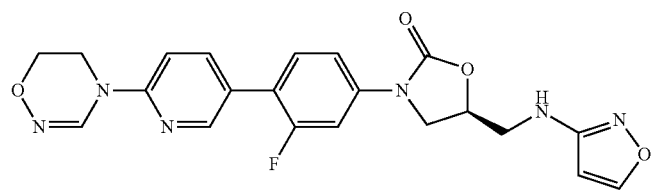

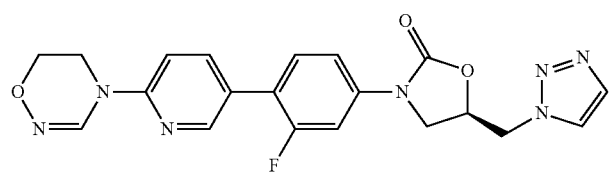

-continued
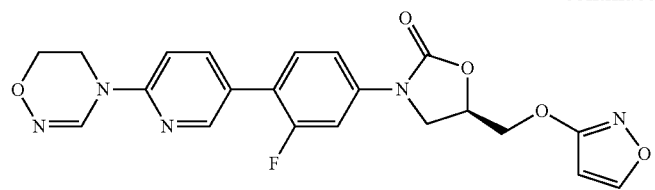
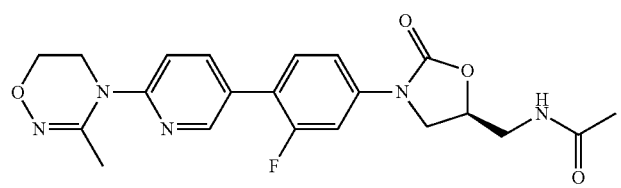
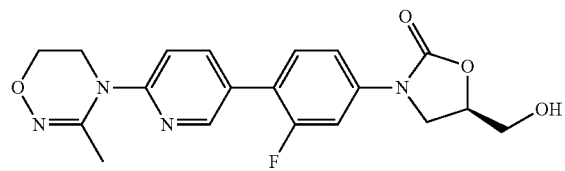
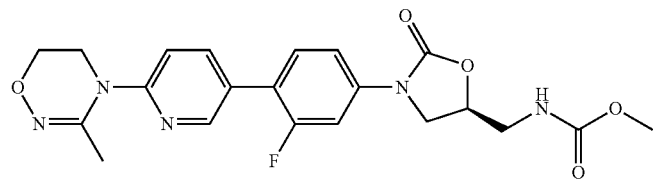
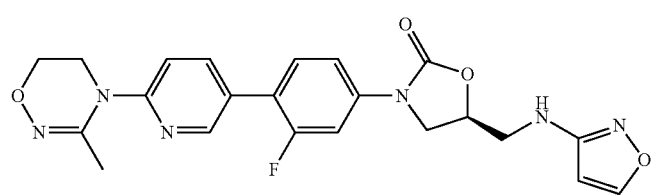
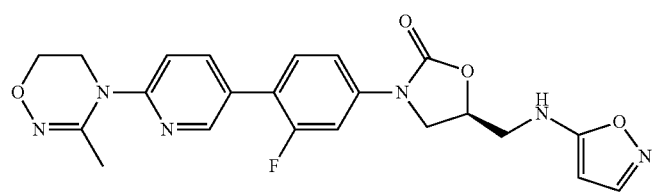
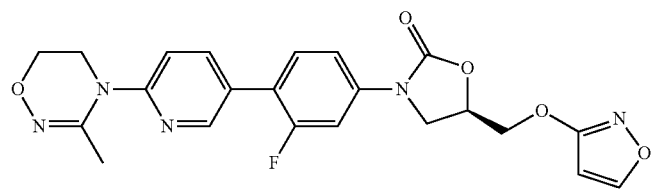
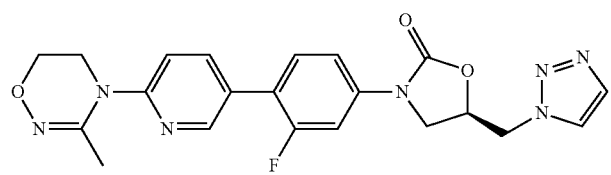
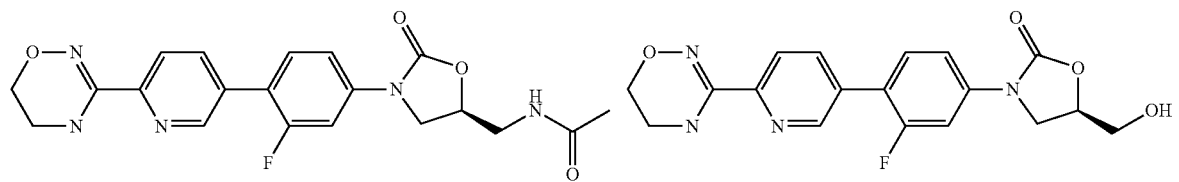

-continued
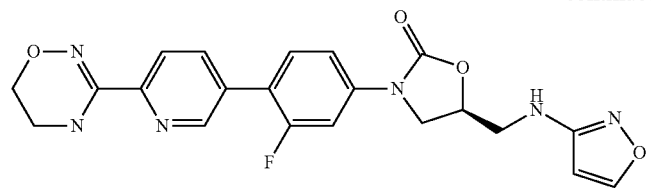
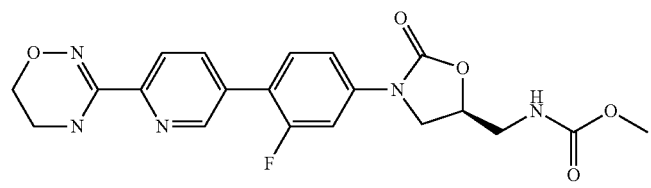
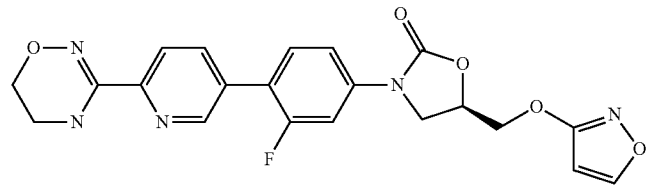
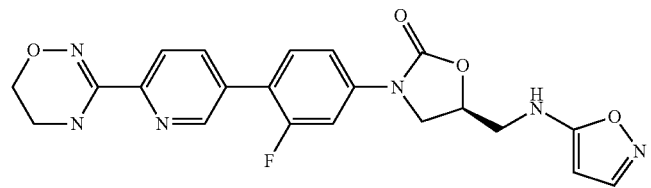
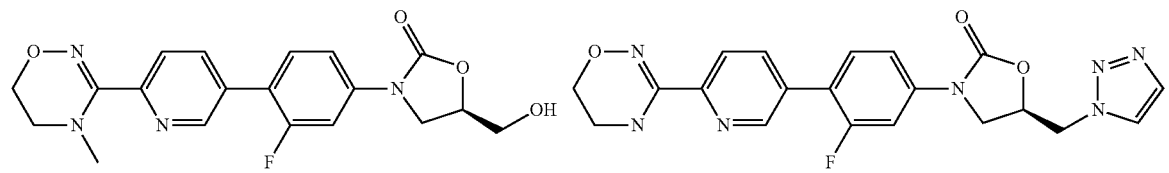
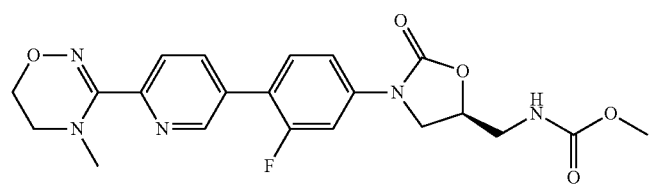
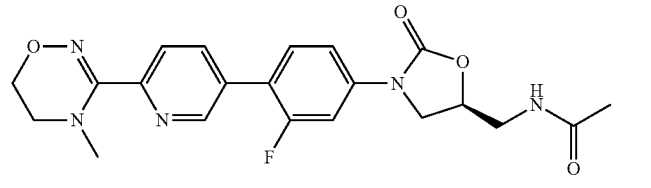
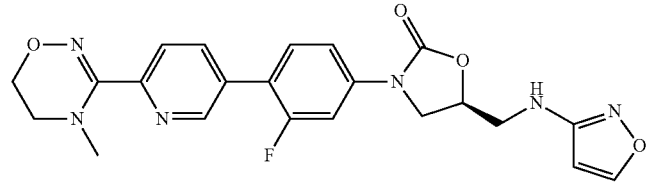
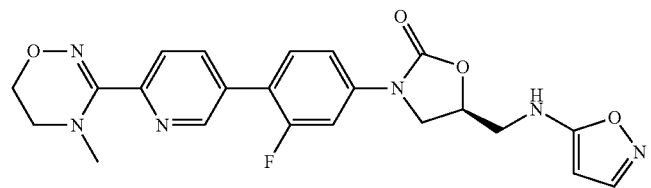

-continued
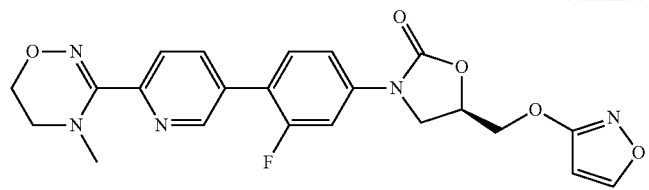
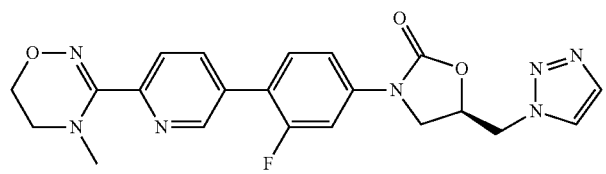
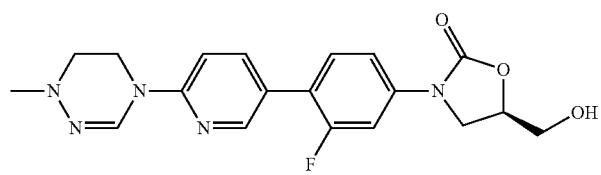
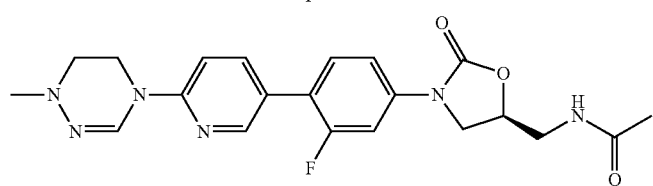
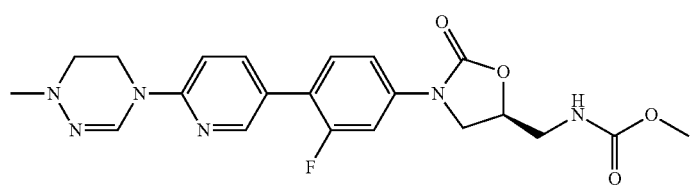
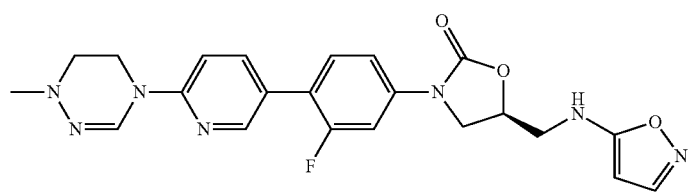
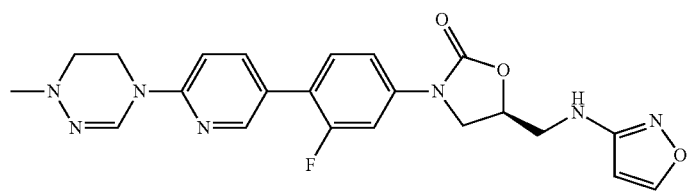
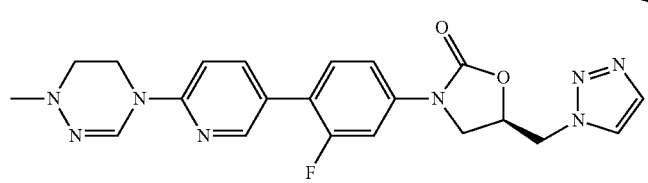
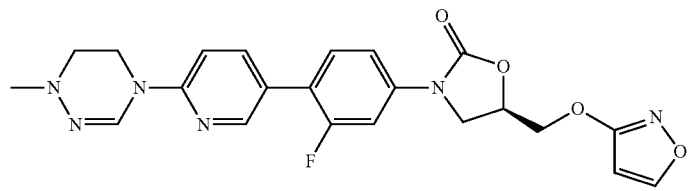

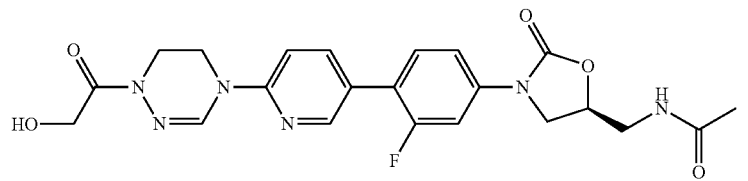
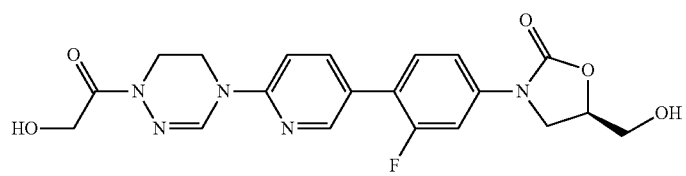
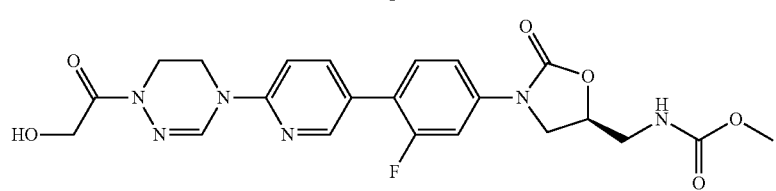
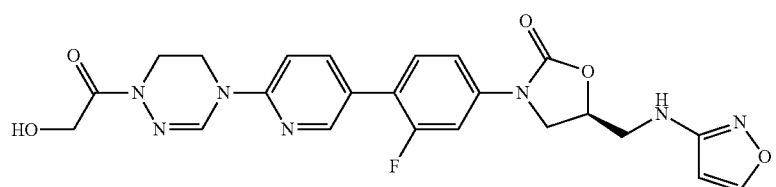
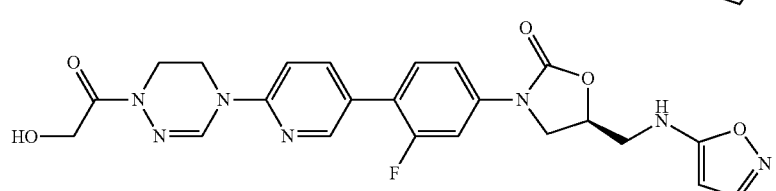
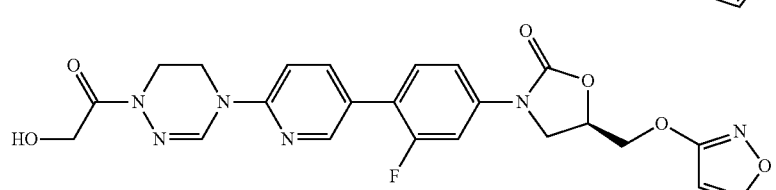
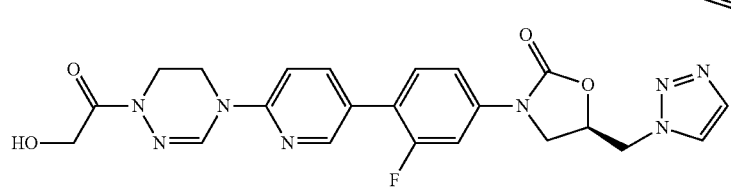
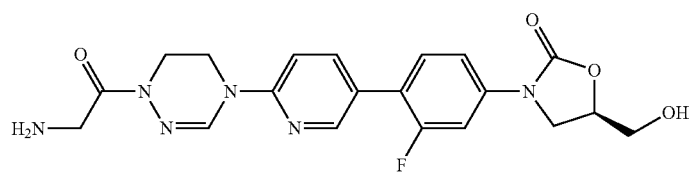
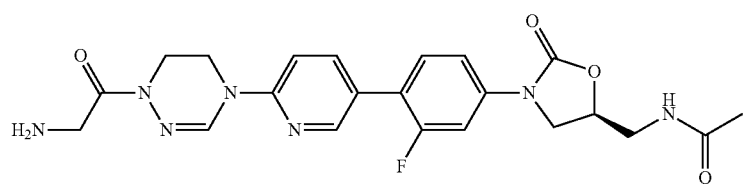

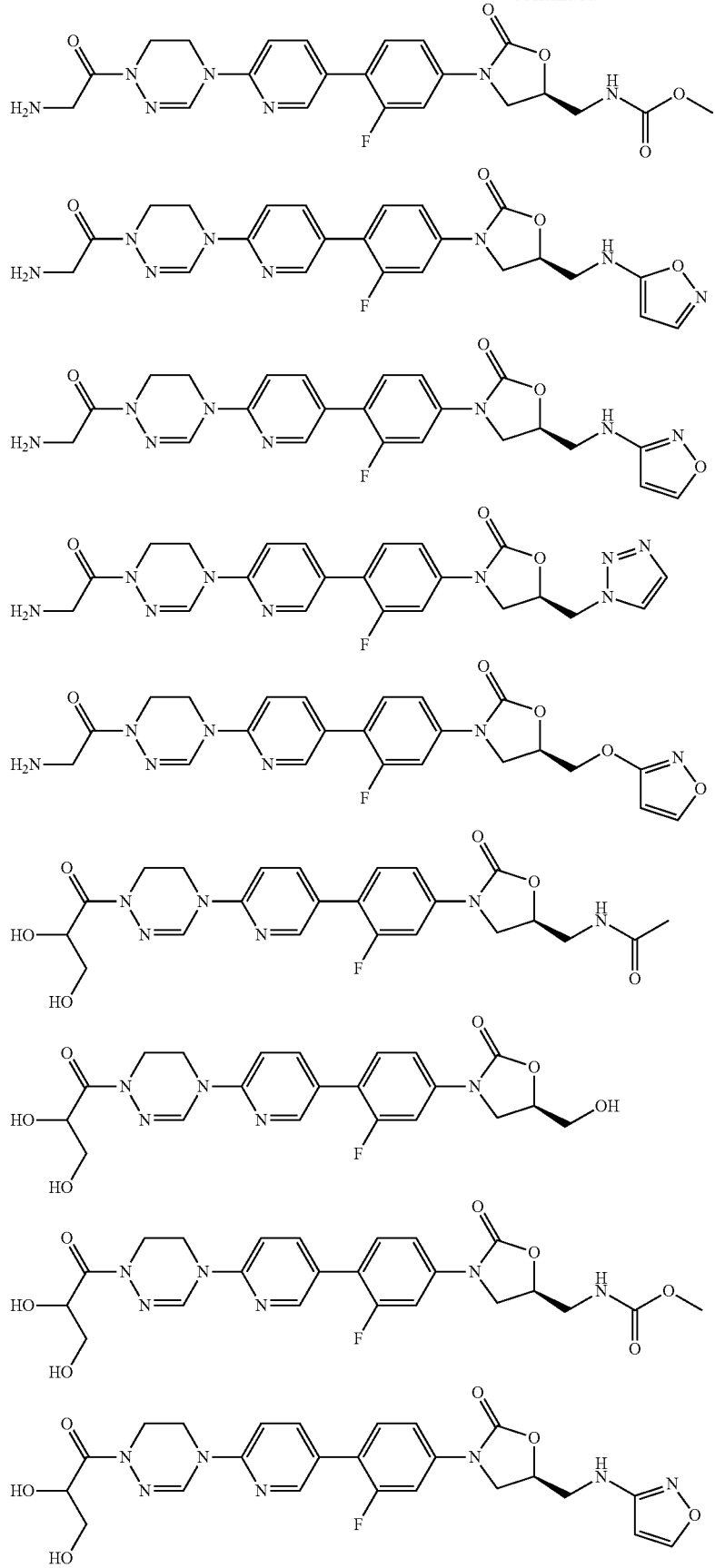

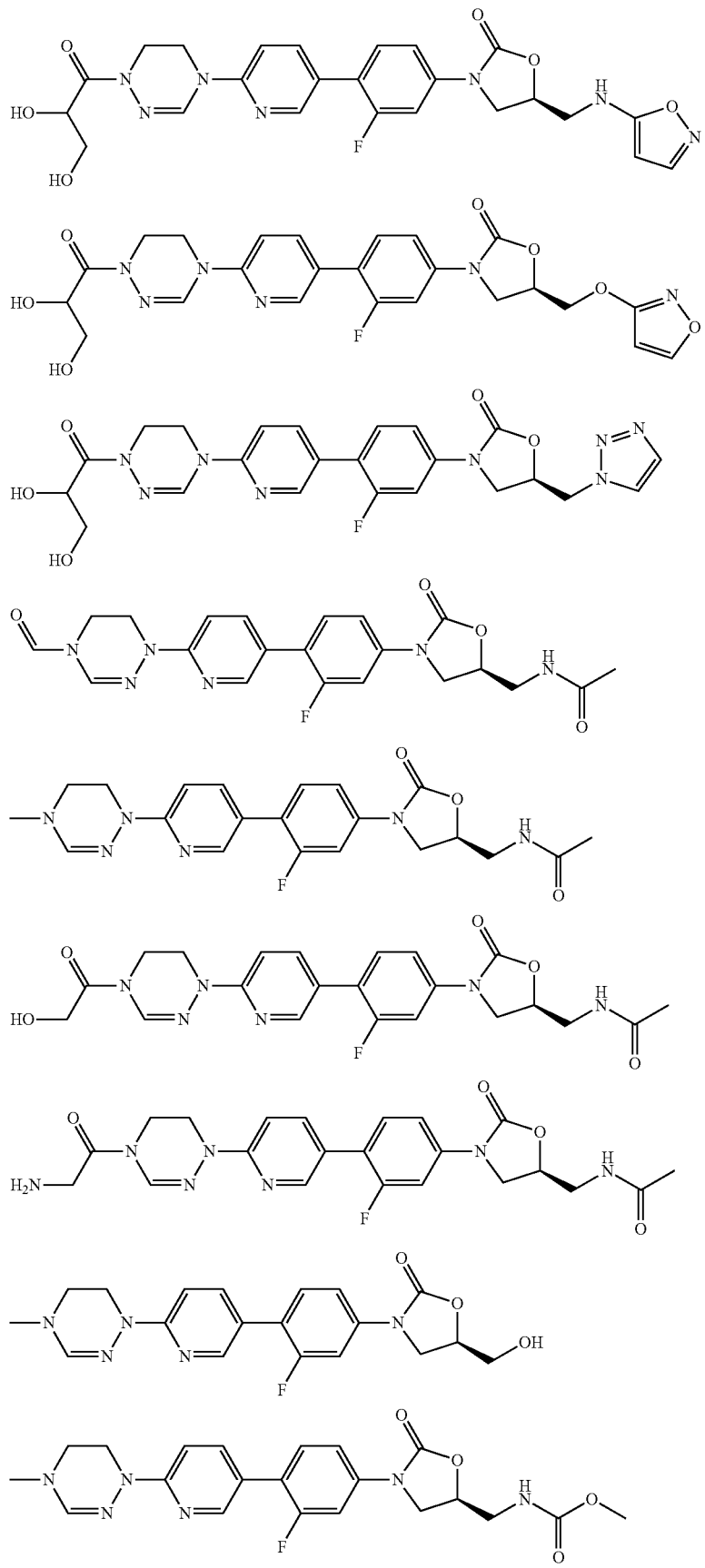

-continued
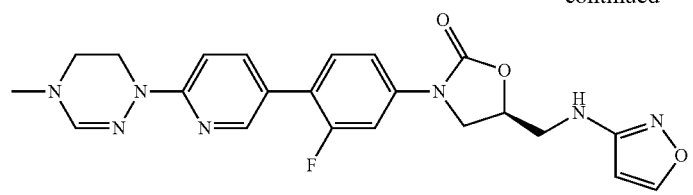
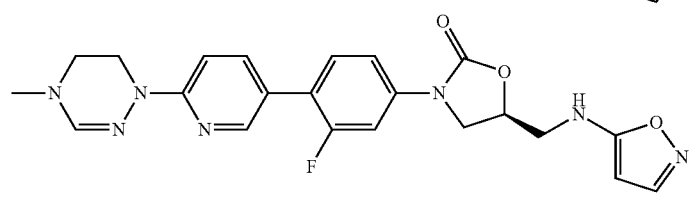
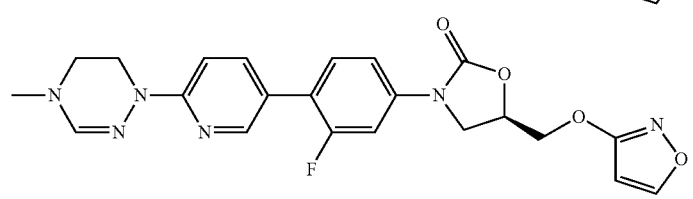
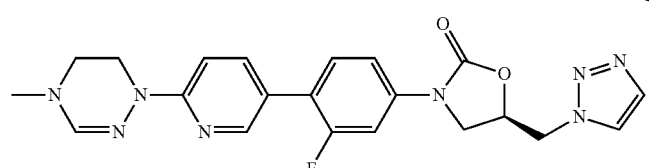
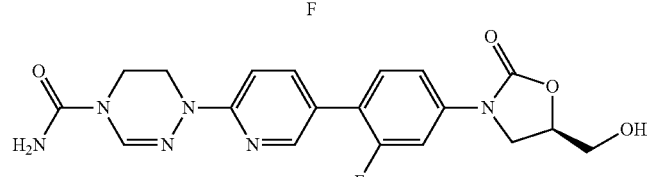
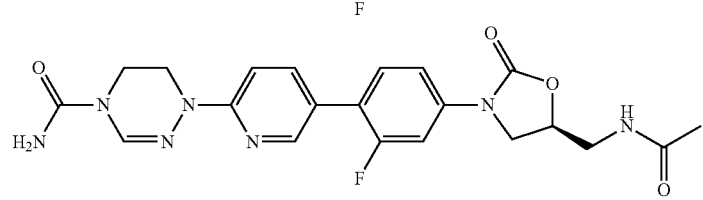
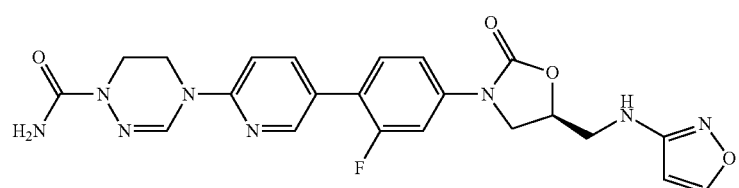
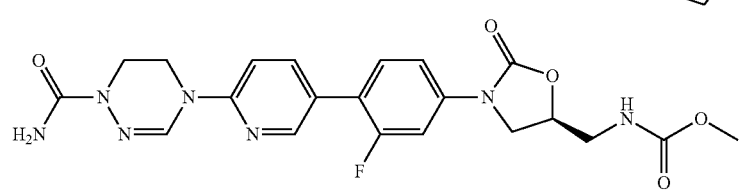
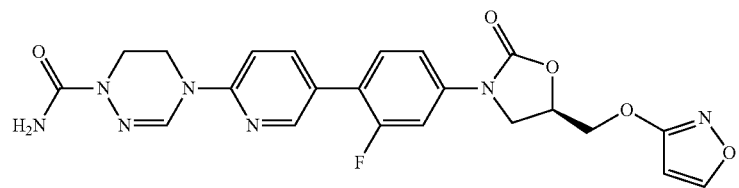

-continued
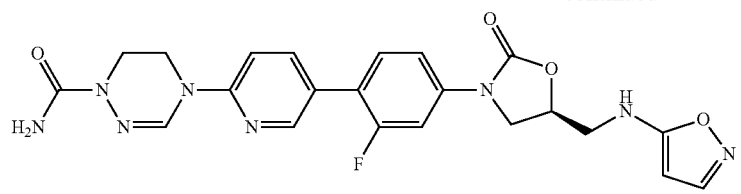
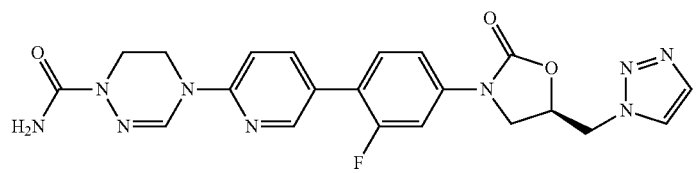
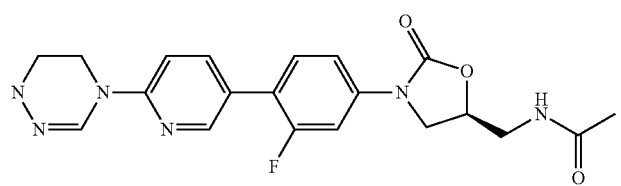
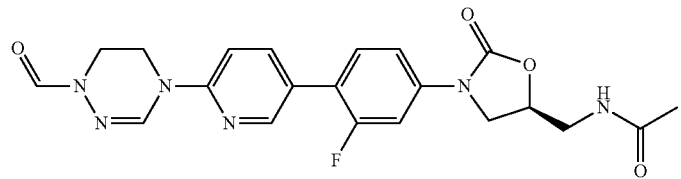
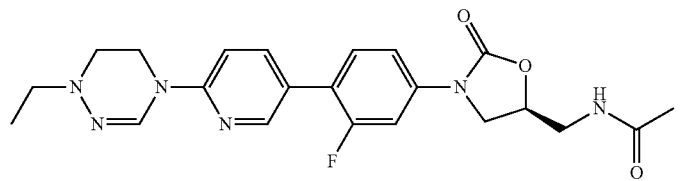
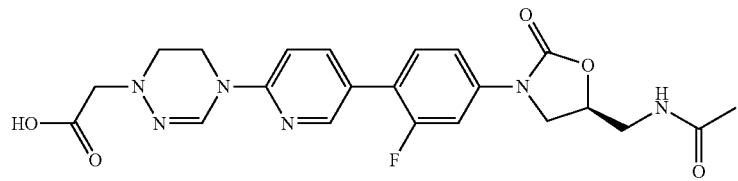
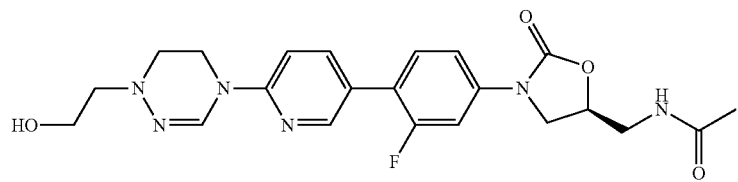
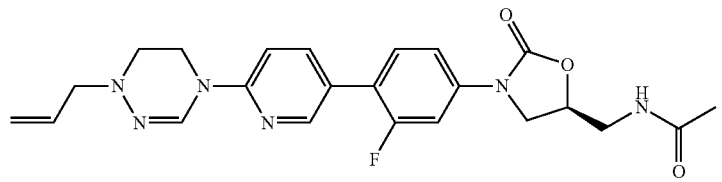
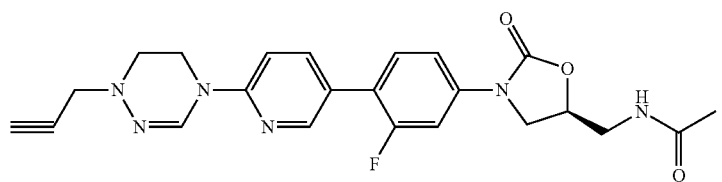

-continued

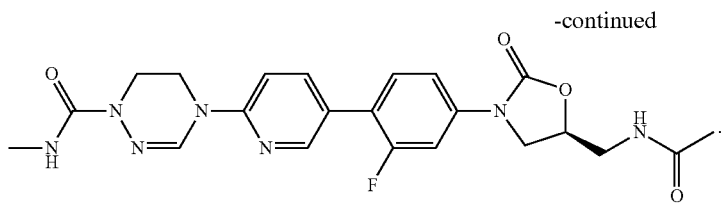

6. A pharmaceutical composition for an antibiotic, the pharmaceutical composition comprising: (a) a therapeutically effective amount of the oxazolidinone derivative, a prodrug thereof, a hydrate thereof, a solvate thereof, an isomer thereof, or a pharmaceutically acceptable salt thereof according to claim 1; and (b) a pharmaceutically acceptable carrier, a diluent, an excipient, or a combination thereof.

7. A method for treating a bacterial infection, comprising:
administering an effective amount of the oxazolidinone derivative represented by Formula 1, a prodrug thereof, a hydrate thereof, a solvate thereof, an isomer thereof, or a pharmaceutically acceptable salt thereof according to claim 1 to a patient in need thereof.

8. A pharmaceutical composition for an antibiotic, the pharmaceutical composition comprising: (a) a therapeutically effective amount of the oxazolidinone derivative, a prodrug thereof, a hydrate thereof, a solvate thereof, an isomer thereof, or a pharmaceutically acceptable salt thereof according claim 2; and (b) a pharmaceutically acceptable carrier, a diluent, and excipient, or a combination thereof.

9. A pharmaceutical composition for an antibiotic, the pharmaceutical composition comprising: (a) a therapeutically effective amount of the oxazolidinone derivative, a prodrug thereof, a hydrate thereof, a solvate thereof, an isomer thereof, or a pharmaceutically acceptable salt thereof according claim 3; and (b) a pharmaceutically acceptable carrier, a diluent, and excipient, or a combination thereof.

10. A pharmaceutical composition for an antibiotic, the pharmaceutical composition comprising: (a) a therapeutically effective amount of the oxazolidinone derivative, a prodrug thereof, a hydrate thereof, a solvate thereof, an isomer thereof, or a pharmaceutically acceptable salt thereof according claim 4; and (b) a pharmaceutically acceptable carrier, a diluent, and excipient, or a combination thereof.

11. A pharmaceutical composition for an antibiotic, the pharmaceutical composition comprising: (a) a therapeutically effective amount of the oxazolidinone derivative, a prodrug thereof, a hydrate thereof, a solvate thereof, an isomer thereof, or a pharmaceutically acceptable salt thereof according claim 5; and (b) a pharmaceutically acceptable carrier, a diluent, and excipient, or a combination thereof.

12. The method according to claim 7, wherein said method is for treating a linezolid-resistant bacterial infection.

* * * * *